US010525021B2

(12) United States Patent
Jin et al.

(10) Patent No.: US 10,525,021 B2
(45) **Date of Patent: *Jan. 7, 2020**

(54) MITOCHONDRIAL UNCOUPLERS FOR TREATMENT OF METABOLIC DISEASES AND CANCER

(71) Applicant: RUTGERS, THE STATE UNIVERSITY OF NEW JERSEY, New Brunswick, NJ (US)

(72) Inventors: Shengkan Jin, Belle Mead, NJ (US); David J. Augeri, Princeton, NJ (US); S. David Kimball, East Windsor, NJ (US); Peng Liu, Piscataway, NJ (US); Hanlin Tao, Branchburg, NJ (US); Xiangang Zeng, Princeton, NJ (US)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/527,808

(22) PCT Filed: Nov. 18, 2015

(86) PCT No.: PCT/US2015/061342

§ 371 (c)(1),
(2) Date: May 18, 2017

(87) PCT Pub. No.: WO2016/081599

PCT Pub. Date: May 26, 2016

(65) Prior Publication Data

US 2017/0319516 A1 Nov. 9, 2017

Related U.S. Application Data

(60) Provisional application No. 62/081,412, filed on Nov. 18, 2014.

(51) Int. Cl.

| | |
|---|---|
| ***A61K 31/166*** | (2006.01) |
| ***C07D 215/42*** | (2006.01) |
| ***C07D 219/04*** | (2006.01) |
| ***C07D 237/20*** | (2006.01) |
| ***C07D 239/42*** | (2006.01) |
| ***C07D 239/557*** | (2006.01) |
| ***C07D 277/56*** | (2006.01) |
| ***C07D 277/62*** | (2006.01) |
| ***C07D 241/24*** | (2006.01) |
| ***C07D 213/78*** | (2006.01) |
| ***C07D 277/68*** | (2006.01) |
| ***A61K 31/155*** | (2006.01) |
| ***A61K 31/50*** | (2006.01) |
| ***A61K 31/497*** | (2006.01) |
| ***A61K 31/4965*** | (2006.01) |
| ***A61K 31/428*** | (2006.01) |
| ***A61K 31/47*** | (2006.01) |
| ***A61K 31/498*** | (2006.01) |
| ***A61K 45/06*** | (2006.01) |
| ***A61K 31/505*** | (2006.01) |
| ***A61K 31/437*** | (2006.01) |

(52) U.S. Cl.

CPC .......... *A61K 31/166* (2013.01); *A61K 31/155* (2013.01); *A61K 31/428* (2013.01); *A61K 31/437* (2013.01); *A61K 31/47* (2013.01); *A61K 31/497* (2013.01); *A61K 31/498* (2013.01); *A61K 31/4965* (2013.01); *A61K 31/50* (2013.01); *A61K 31/505* (2013.01); *A61K 45/06* (2013.01); *C07D 213/78* (2013.01); *C07D 215/42* (2013.01); *C07D 219/04* (2013.01); *C07D 237/20* (2013.01); *C07D 239/42* (2013.01); *C07D 239/557* (2013.01); *C07D 241/24* (2013.01); *C07D 277/56* (2013.01); *C07D 277/62* (2013.01); *C07D 277/68* (2013.01)

(58) Field of Classification Search

None

See application file for complete search history.

(56) References Cited

U.S. PATENT DOCUMENTS

| | | | |
|---|---|---|---|
| 3,113,067 | A | 12/1963 | Reimer et al. |
| 3,147,300 | A | 9/1964 | Ernst et al. |
| 3,909,816 | A | 9/1975 | Teeters |
| 4,120,811 | A | 10/1978 | Yagi et al. |
| 4,405,616 | A | 9/1983 | Rajadhyaksha |
| 4,659,738 | A | 4/1987 | Miller et al. |
| 4,801,586 | A | 1/1989 | Minaskanian et al. |
| 4,861,764 | A | 8/1989 | Samour et al. |
| 4,886,783 | A | 12/1989 | Minaskanian et al. |

(Continued)

FOREIGN PATENT DOCUMENTS

| | | | |
|---|---|---|---|
| CN | 1658855 | A | 8/2005 |
| EP | 1510207 | A1 | 3/2005 |

(Continued)

OTHER PUBLICATIONS

Kang, Sunghyun. Discovery of novel 2-hydroxydiarylamide derivatives as TMPRSS4 inhibitors. Bioorganic and Medicinal Chemistry Letters. 23 (2013) 1748-1751.*

Coburn, Robert A. Potential Salicylamide Antiplaque Agents: In Vitro Antibacterial Activity against Actinomyces viscosus. J. Med. Chem. 24 (1981) 1245-1249.*

Pilyugin, V.S. 13C NMR Spectra and Biological Activity of N-(1H-Benzimidazol-2-yl)benzamides. Russian Journal of General Chemistry. 76(10), 2006, 1653-1659.*

(Continued)

*Primary Examiner* — Samantha L Shterengarts

(74) *Attorney, Agent, or Firm* — Pepper Hamilton LLP

(57) ABSTRACT

2-hydroxy-benzoic anilide compounds and derivatives, compositions thereof, and methods for treating metabolic diseases and cancer through uncoupling mitochondria.

7 Claims, No Drawings

(56) References Cited

U.S. PATENT DOCUMENTS

| | | | |
|---|---|---|---|
| 4,983,396 | A | 1/1991 | Bodor et al. |
| 5,118,845 | A | 6/1992 | Peck et al. |
| 5,196,410 | A | 3/1993 | Francoeur et al. |
| 8,486,374 | B2 | 7/2013 | Tamarkin et al. |
| 8,741,265 | B2 | 6/2014 | Tamarkin et al. |
| 10,227,315 | B2 | 3/2019 | Jin et al. |
| 2004/0138301 | A1 | 7/2004 | Hansen et al. |
| 2005/0282862 | A1 | 12/2005 | Beight et al. |
| 2006/0089395 | A1 | 4/2006 | Muto et al. |
| 2006/0292146 | A1 | 12/2006 | Dixon et al. |
| 2007/0299111 | A1 | 12/2007 | Powers et al. |
| 2008/0039629 | A1 | 2/2008 | Ramesh et al. |
| 2009/0062396 | A1 | 3/2009 | Olesen et al. |
| 2009/0239919 | A1 | 9/2009 | Wood et al. |
| 2010/0113770 | A1 | 5/2010 | Muto et al. |
| 2010/0190832 | A1 | 7/2010 | Surolia |
| 2013/0150399 | A1 | 6/2013 | Koong et al. |
| 2013/0324555 | A1 | 12/2013 | Wood et al. |
| 2014/0221411 | A1 | 8/2014 | Kim et al. |
| 2016/0046560 | A1 | 2/2016 | Sexton et al. |

FOREIGN PATENT DOCUMENTS

| | | | |
|---|---|---|---|
| EP | 1512397 | A1 | 3/2005 |
| JP | S60195158 | A | 10/1985 |
| WO | 2000006143 | A1 | 2/2000 |
| WO | 2004006906 | A2 | 1/2004 |
| WO | 2007019251 | A2 | 2/2007 |
| WO | 2009032749 | B1 | 3/2009 |
| WO | 2009047584 | A1 | 4/2009 |
| WO | 2012025638 | A1 | 3/2012 |
| WO | 2012040223 | B2 | 3/2012 |
| WO | 2012068274 | A1 | 5/2012 |
| WO | 2013164769 | A1 | 11/2013 |
| WO | 2013169939 | A2 | 11/2013 |
| WO | 2015154169 | A1 | 10/2015 |
| WO | 2016004513 | A1 | 1/2016 |
| WO | 2016081599 | A1 | 5/2016 |

OTHER PUBLICATIONS

Database Registry Chemical Abstracts Service, Columbus, Ohio, Accession No. RN 1040060-74-9, Entered STN: Aug. 11, 2008.*

Database Registry Chemical Abstracts Service, Columbus, Ohio, Accession No. RN 1041591-75-6, Entered STN: Aug. 17, 2008.*

Diadone et al., Salicylanilide and its heterocyclic analogs. A Comparative study of their antimicrobial activity, Die Pharmazie: An Internatioanl Journal of Pharmaceutical Sciences (Jan. 1, 1990), 45(6):441-442.

Kang et al., Discovery of Novel 2-hydroxydiarylamide derivatives as TMPRSS4 inhibitors, Bioorganic & Medical Chemistry Letters (2013), 23(6):1748-1751.

Vinsova et al., Salicylanilide diethyl phophates: Synthesis, antimicrobial activity and cytotoxicity, Bioorganic & Medicinal Chemistry (Dec. 12, 2013), 22(2):728-737.

Extended European Search Report for PCT/US2015/061342, dated May 24, 2018.

Wallace et al. Mitochondrial Targets of Drug Toxicity, Annu. Rev. Pharmacol. Toxicol., 2000, vol. 40, pp. 353-388.

Stumvall et al. Type 2 diabetes: principles of pathogenesis and therapy, Lancet, 2005, vol. 365, pp. 1333-1346.

Andrews et al., The Biology and Toxicology of Molluscicides, Bayluscide, Pharmac. Ther., 19:245-295 (1983).

Kenwood et al., Structure-activity relationships of furazano[3,4-b]pyrazines as mitochondrial uncouplers, Bioorganic & Medicinal Chemistry Letters 25 (2015), 4858-4861.

International Search Report and Written Opinion of the International Searching Authority, for PCT/US2011/061028, dated Apr. 2, 2012.

Extended European Search Report for PCT/US2011/061028, dated Mar. 21, 2014.

Curnock, Adam P., et al., Inhibition of stimulated Jurkat cell adenosine 3', 5'-cyclic monophosphate synthesis by the immunomodulatory compound HR325, Biochemical Pharmacology, vol. 61, No. 2, Jan. 1, 2001, pp. 227-235; XP055107261, ISSN: 0006-2952, DOI: 10.016/50006-2952(00)00552-9.

Samuel V.T., et al., Lancet, 2010, 375:2267-77.

Terada, H., Environ. Health Perspect. 1990, 87:213-218.

Design of Prodrugs, Notari, Robert E., edited by H. Bundgaard (Elsevier, 1985), and Methods in Enzymology, vol. 112, at pp. 309-396, edited by K. Widder et al. (Academic Press, 1985).

A textbook of Drug Design and Development, edited by Krosgaard-Larsen and H. Bundgaard, Chapter 5, Design and Application of Prodrugs, by H. Bundgaard, at pp. 113-191 (1991).

Tao H., et al. Niclosamide ethanolamine improves blood glycemic control and reduces hepatic steatosis in mice, Nat. Med. Nov. 2014:20(11): 1263-1269.

International Search Report and Written Opinion of the International Searching Authority, for PCT/US2015/061342, dated Jan. 28, 2016.

Reddy, PVG et al. Synthesis of novel benzothiazole compounds with an extended conjugated system. ARKIVOC, vol. xvi, 2007, pp. 113-112.

Perry RJ, Zhang D, Zhang XM, Boyer JL, Shulman GL, Science Mar. 13, 2015;347(6227):1253-6.

Vander Heiden MG, Cantley LC, Thompson CB. Science. May 22, 2009;324(5930):1029-33.

J. March, Advanced Organic Chemistry: Reactions, Mechanisms and Structure, 4th Ed. (New York: Wiley-Interscience, 1992.

Medicinal Chemistry: Principles and Practice, F.D. King, ed., The Royal Society of Chemistry, Cambridge, UK, 1994.

Hydrolysis in Drug and Prodrug Metabolism. Chemistry, Biochemistry and Enzymology, B. Testa, J. M. Mayer, VCHA and Wiley-VCH, Zurich, Switzerland, 2003.

The Practice of Medicinal Chemistry, C. G. Wermuth, 2nd ed., Academic Press, San Diego, CA, 1999.

Remington's Pharmaceutical Sciences, 18 Edition, Mack Publishing Company, Easton, PA, 1990.

Farmaco, 2005, vol. 60, # 5 p. 399-408.

Bioorganic and Medicinal Chemistry Letters, 2013, 23(6), 1748-1751.

The Merck Index, Thirteenth Edition, Budavari et al., Eds., Merck & Co., Inc., Rahway, N.J. (2001).

CTFA (Cosmetic, Toiletry, and Fragrance Association) International Cosmetic Ingredient Dictionary and Handbook, Tenth Edition (2004).

Inactive Ingredient Guide, U.S. Food and Drug Administration (FDA) Center for Drug Evaluation and Research (CDER) Office of Management, http://www.accessdata.fda.gov/scripts/cder/iig/index.cfm.

Goodman and Gillman's: The Pharmacological Bases of Therapeutics, 8th Ed., Gilman et al. Eds. Pergamon Press (1990).

Chemical Abstracts Registry No. 78417-51-3, indexed in the Registry file on STN CAS ONLINE on Nov. 16, 1984.

Chemical Abstracts Registry No. 1040017-73-5, indexed in the Registry file on STN CAS ONLINE on Aug. 10, 2008.

Chemical Abstracts Registry No. 1042515-02-5, indexed in the Registry file on STN CAS ONLINE on Aug. 21, 2008.

Chemical Abstracts Registry No. 78417-52-4, indexed in the Registry file on STN CAS ONLINE on Nov. 16, 1984.

Chemical Abstracts Registry No. 1036494-79-7, indexed in the Registry file on STN CAS ONLINE on Jul. 27, 2008.

Chemical Abstracts Registry No. 1350060-36-4, indexed in the Registry file on STN CAS ONLINE on Dec. 7 2011.

Matyk et al., Farmaco (2005), 60(5) pp. 399-408.

Chemical Abstracts Registry No. 1187819-29-9, indexed in the Registry file on STN CAS ONLINE on Oct. 11, 2009.

Chemical Abstracts Registry No. 1426396-74-8, indexed in the Registry file on STN CAS ONLINE on Mar. 27, 2013.

Chemical Abstracts Registry No. 1482295-68-0, indexed in the Registry file on STN CAS ONLINE on Nov. 27, 2013.

Chemical Abstracts Registry No. 634185-54-9, indexed in the Registry file on STN CAS ONLINE on Jan. 5, 2004.

(56) References Cited

OTHER PUBLICATIONS

Chemical Abstracts Registry No. 677729-40-7, indexed in the Registry file on STN CAS ONLINE on Apr. 29, 2004.

* cited by examiner

MITOCHONDRIAL UNCOUPLERS FOR TREATMENT OF METABOLIC DISEASES AND CANCER

CROSS-REFERENCE TO RELATED APPLICATIONS

This application is a U.S. national stage filing under 35 U.S.C. § 371 of International Application No. PCT/US2015/061342 filed Nov. 18, 2015, which claims priority under 35 U.S.C. § 119(e) of U.S. Provisional Application Ser. No. 62/081,412, filed Nov. 18, 2014, the disclosures of which are herein incorporated by reference in their entireties.

BACKGROUND

Mitochondria are central to cellular metabolism, which provides both energy to sustain biological activities and metabolic intermediates for biosynthesis. Glucose as well as lipids such as triglyceride are the most important fuels of cells. Glucose first metabolizes to pyruvate through glycolysis. In turn, pyruvate enters mitochondria, where it converts to acetyl-CoA. Similarly, triglyceride is first hydrolyzed to glycerol and fatty acid, which enter mitochondria, where they are oxidized to acetyl-CoA. In mitochondrial matrix, acetyl-CoA from glucose metabolism as well as lipid metabolism is then oxidized through TCA cycle. The energy released from the oxidation reactions is stored in the form of high energy electrons in the molecules of NADH and $FADH_2$. Electrons from NADH and $FADH_2$ are in turn fed into the mitochondrial electron transporter chain, which are localized on the inner membrane of mitochondria. As the electrons travel through the electron transporter chain and reach the electron receptor, oxygen molecule, energy is released and used for pumping protons from mitochondrial matrix across the mitochondrial inner membrane, establishing a proton gradient across the membrane. Finally, protons travel across the mitochondrial inner membrane through the $F_oF_1$-ATP synthase and drive the synthesis of ATP, the energy molecule that can be directly used by the various cellular machineries. Under normal conditions, mitochondrial oxidation provides more than 90% of cellular ATP. In addition, mitochondrial oxidation provides and regulates the availability of metabolic intermediates required for biosynthesis of macromolecules such as RNA, DNA, lipids.

Generally, mitochondrial oxidation of acetyl-CoA and ATP synthesis are coupled in response to cellular energy needs. However, mitochondrial oxidation can be decoupled from ATP synthesis by mitochondrial uncouplers. Mitochondrial uncouplers facilitate the inward translocation of protons across mitochondrial inner membrane (not through the $F_oF_1$-ATP synthase), thus dissipate or reduce the proton gradient without generating ATP. Mitochondrial uncoupling could be mediated by protein mitochondrial uncouplers such as UCP1 protein, or chemical uncouplers such as DNP (dinitrophenol). As a result, mitochondrial uncouplers usually lead to the following effects: (1). reduction of mitochondrial energy efficiency, (2). increase of lipid and glucose oxidation, (3). activation of AMPK enzyme, (4). alteration of availability of metabolic intermediates for biomass biosynthesis required for cell proliferation.

Although chemical uncouplers of mitochondria have been reported in literature, there remains a need for the discovery of new types of chemical mitochondrial uncouplers with a combination of favorable pharmacokinetic and pharmacodynamic properties.

SUMMARY

Various embodiments provide compounds, compositions, and methods for prevention and treatment of metabolic diseases and cancer. Compounds described herein exhibit activities of mitochondrial uncoupling, activation of AMPK, and inhibition of cell proliferation.

In one aspect there is provided a compound of formula (I) having the structure:

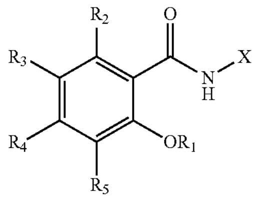

or a pharmaceutically acceptable salt, solvate, or prodrug thereof, wherein:

$R_1$ is selected from the group consisting of H, M, $PO(OH)_2$, $PO_2(OH)M$, $PO_3M_2$, $PO(OH)R_a$, $PO(OM)R_a$, $PO(R_a)_2$, and $C(O)R_a$, wherein M is a metal cation or an organic amine;

$R_2$, $R_3$, $R_4$, and $R_5$ are each independently selected from the group consisting of H, halogen, $CF_3$, $SF_3$, CN, $NO_2$, alkyl, haloalkyl, aryl, COOH, $COOR_a$, and $CONHR_a$;

X is a 9-membered ring having the structure:

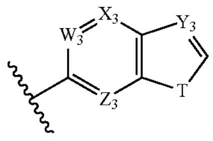

or

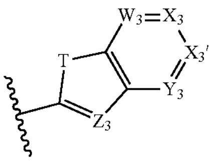

wherein T is O, S, or $NR_a$; $W_3$, $X_3$, $X_3'$, $Y_3$, and $Z_3$ are each independently $CR_b$ or N;

each $R_a$ is independently selected from the group consisting of H, alkyl, aryl, alkoxy, aryloxy, alkoxyalkyl, amino, alkylamino, and alkyl-carbonyloxy-alkyl;

each $R_b$ is independently selected from the group consisting of H, halogen, CN, $NO_2$, $CO_2H$, $CO_2R_a$, $CF_3$, $OCF_3$, $SF_3$, $C_{6-10}$aryl, alkyl, haloalkyl, $CONHR_a$, and $C'NR_c(N(R_d)_2)$;

each $R_c$ is independently selected from the group consisting of H, CN, O-alkyl, $NH_2$, mono-alkyl substituted amino, and di-alkyl substituted amino; and each $R_d$ is independently selected from the group consisting of H and alkyl, wherein said alkyl is optionally substituted with halogen, CN, $NO_2$, $CO_2H$, $CO_2R_a$, $CF_3$, $OCF_3$, $SF_3$, $C_{6-10}$aryl, or $CONHR_a$; and provided that said 9-membered ring contains at least one nitrogen and is not indole.

In some embodiments, the 9-membered ring is benzothizole optionally substituted with $R_b$.

Another aspect of the invention provides a compound of formula (I) having the structure:

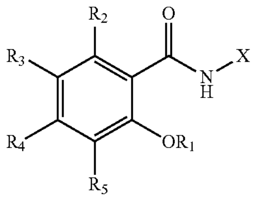

or a pharmaceutically acceptable salt, solvate, or prodrug thereof, wherein:

$R_1$ is selected from the group consisting of H, M, $PO(OH)_2$, $PO_2(OH)M$, $PO_3M_2$, $PO(OH)R_a$, $PO(OM)R_a$, $PO(R_a)_2$, and $C(O)R_a$, wherein M is a metal cation or an organic amine;

$R_2$, $R_3$, $R_4$, and $R_5$ are each independently selected from the group consisting of H, halogen, $SF_3$, $CF_3$, $OCF_3$, CN, $NO_2$, alkyl, haloalkyl, aryl, $CO_2H$, $CO_2R_a$, and $CONHR_a$;

X is a six-membered heteroaryl having the structure:

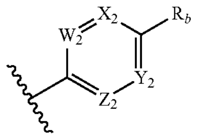

wherein two of $W_2$, $X_2$, $Y_2$ and $Z_2$ are N and the other two are $CR_b$, and $W_2$ and $Z_2$ are not both N;

each $R_a$ is independently selected from the group consisting of H, alkyl, aryl, alkoxy, aryloxy, alkoxyalkyl, amino, alkylamino, and alkyl-carbonyloxy-alkyl; and each $R_b$ is independently selected from the group consisting of H, halogen, CN, $NO_2$, $CO_2H$, $CO_2R_a$, $CF_3$, $OCF_3$, $SF_3$, $C_{6-10}$ aryl, alkyl, haloalkyl, $CONHR_a$, and $C{=}NR_c(N(R_d)_2)$;

each $R_c$ is independently selected from the group consisting of H, CN, O-alkyl, $NH_2$, mono-alkyl substituted amino, and di-alkyl substituted amino;

each $R_d$ is independently selected from the group consisting of H and alkyl, wherein said alkyl is optionally substituted with halogen, CN, $NO_2$, $CO_2H$, $CO_2R_a$, $CF_3$, $OCF_3$, $SF_3$, $C_{6-10}$aryl, or $CONHR_a$; and provided that when said six-membered heteroaryl is a pyrazine, $R_b$ is selected from halogen, CN, $NO_2$, $CO_2H$, $CO_2R_a$, $CF_3$, $OCF_3$, $SF_3$, $C_{6-10}$ aryl, alkyl, haloalkyl, $CONHR_a$, and $C{=}NR_c(N(R_d)_2)$.

In some embodiments, the 6-membered ring is pyrazine substituted with $R_b$.

Another aspect of the invention provides a compound of formula (I) having the structure:

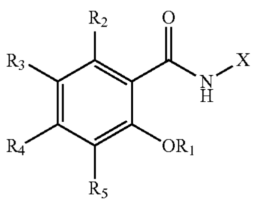

or a pharmaceutically acceptable salt, solvate, or prodrug thereof, wherein:

$R_1$ is selected from the group consisting of H, M, $PO(OH)_2$, $PO_2(OH)M$, $PO_3M_2$, $PO(OH)R_a$, $PO(OM)R_a$, $PO(R_a)_2$ and $C(O)R_a$, wherein M is a metal cation or an organic amine;

$R_2$, $R_3$, $R_4$, and $R_5$ are each independently selected from the group consisting of H, halogen, $CF_3$, $SF_3$, CN, $NO_2$, alkyl, haloalkyl, aryl, COOH, $COOR_a$, and $CONHR_a$;

X is a pyridine ring substituted with one or more $R_b$, wherein each $R_b$ is independently selected from the group consisting of halogen, CN, $NO_2$, $CO_2H$, $CO_2R_a$, $CF_3$, $OCF_3$, $SF_3$, $C_{6-10}$ aryl, alkyl, haloalkyl, $CONHR_a$, and $C{=}NR_c(N(R_d)_2)$, provided that said halogen is not substituted ortho to the ring nitrogen;

each $R_a$ is independently selected from the group consisting of H, alkyl, aryl, alkoxy, aryloxy, alkoxyalkyl, amino, alkylamino, and alkyl-carbonyloxy-alkyl;

each $R_c$ is independently selected from the group consisting of H, CN, O-alkyl, $NH_2$, mono-alkyl substituted amino, and di-alkyl substituted amino; and each $R_d$ is independently selected from the group consisting of H and alkyl, wherein said alkyl is optionally substituted with halogen, CN, $NO_2$, $CO_2H$, $CO_2R_a$, $CF_3$, $OCF_3$, $SF_3$, $C_{6-10}$aryl, or $CONHR_a$.

Another aspect of the invention provides a compound of formula (I) or a pharmaceutically acceptable salt, solvate, or prodrug thereof, wherein:

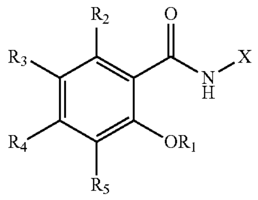

(I)

$R_1$ is selected from the group consisting of H, M, $PO(OH)_2$, $PO_2(OH)M$, $PO_3M_2$, $PO(OH)R_a$, $PO(OM)R_a$, $PO(R_a)_2$, and $C(O)R_a$, wherein M is a metal cation or an organic amine;

$R_2$, $R_3$, $R_4$, and $R_5$ are each independently selected from the group consisting of H, halogen, $CF_3$, $SF_3$, CN, $NO_2$, alkyl, haloalkyl, aryl, COOH, $COOR_a$, and $CONHR_a$;

X is optionally substituted with at least one $R_b$ and X is selected from the group consisting of imidazole, pyrrole, tetrazole, cyano-thiazole, triazine, indazole, purine, benzimidazole, benzoxazole, benzothiazole, isoquinoline, and quinazoline;

each $R_a$ is independently selected from the group consisting of H, alkyl, aryl, alkoxy, aryloxy, alkoxyalkyl, amino, alkylamino, and alkyl-carbonyloxy-alkyl;

each $R_b$ is independently selected from the group consisting of H, halogen, CN, $NO_2$, $CO_2H$, $CO_2R_a$, $CF_3$, $OCF_3$, $SF_3$, $C_{6-10}$aryl, alkyl, haloalkyl, $CONHR_a$, and $C{=}NR_c(N(R_d)_2)$;

each $R_e$ is independently selected from the group consisting of H, CN, O-alkyl, $NH_2$, mono-alkyl substituted amino, and di-alkyl substituted amino; and each $R_d$ is independently selected from the group consisting of H and alkyl, wherein said alkyl is optionally substituted with halogen, CN, $NO_2$, $CO_2H$, $CO_2R_a$, $CF_3$, $OCF_3$, $SF_3$, $C_{6-10}$aryl, or $CONHR_a$;

provided that when X is cyano-thiazole, said cyano-thiazole is not substituted with tert-butyl.

Another aspect of the invention provides a compound of formula (I) having the structure:

(I)

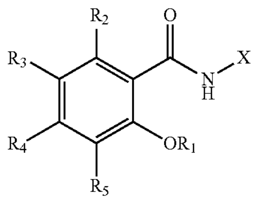

or a pharmaceutically acceptable salt, solvate, or prodrug thereof, wherein:

$R_1$ is selected from the group consisting of $PO(OH)_2$, $PO_2(OH)M$, $PO_3M_2$, $PO(OH)R_a$, $PO(OM)R_a$, $PO(R_a)_2$, and $C(O)R_e$, wherein M is a metal cation or an organic amine;

$R_2$, $R_3$, $R_4$, and $R_5$ are each independently selected from the group consisting of H, halogen, $CF_3$, $SF_3$, CN, $NO_2$, alkyl, haloalkyl, aryl, COOH, $COOR_a$, and $CONHR_a$;

X is a $C_{6-10}$aryl optionally substituted with one or more $R_b$;

each $R_a$ is independently selected from the group consisting of H, alkyl, aryl, alkoxy, aryloxy, alkoxyalkyl, amino, alkylamino, and alkyl-carbonyloxy-alkyl;

each $R_b$ is independently selected from the group consisting of H, halogen, CN, $NO_2$, $CO_2H$, $CO_2R_a$, $CF_3$, $OCF_3$, $SF_3$, $C_{6-10}$aryl, alkyl, haloalkyl, $CONHR_a$, and $C{=}NR_c(N(R_d)_2)$;

each $R_c$ is independently selected from the group consisting of H, CN, O-alkyl, $NH_2$, mono-alkyl substituted amino, and di-alkyl substituted amino;

each $R_d$ is independently selected from the group consisting of H and alkyl, wherein said alkyl is optionally substituted with halogen, CN, $NO_2$, $CO_2H$, $CO_2R_a$, $CF_3$, $OCF_3$, $SF_3$, $C_{6-10}$aryl, or $CONHR_a$; and $R_e$ is $NH_2$ optionally substituted with one or two alkyl groups.

In some embodiments, $R_1$ is selected from the group consisting of $PO(OH)_2$, $PO_2(OH)M$, $PO_3M_2$, $PO(OH)R_a$, $PO(OM)R_a$, and $PO(R_a)_2$.

In another aspect there is provided compositions containing any of the compounds described herein.

In some embodiments, there is provided the mitochondrial uncoupling activities of the compounds.

In some embodiments, there is provided the effectiveness of the compounds in activating AMPK (AMP-activating kinase).

In some embodiments, there is provided the effectiveness of the compounds in inhibiting cell proliferation and clonogenicity.

In another aspect there is provided a method of using a therapeutic effective amount of a compound described herein as mitochondrial uncoupling agent for treating or preventing a metabolic disease or disorder in a subject.

In some embodiments, there is provided use of compounds or compositions described herein for treating or preventing metabolic disease or disorder, wherein the disease or disorder is type 2 diabetes.

In some embodiments, there is provided use of compounds or compositions described herein for treating or preventing complications caused by diabetes including cardiovascular diseases, neurodegenerative disorders, atherosclerosis, hypertension, coronary heart diseasesnephropathy, retinopathy, neuropathy, diabetic heart failure.

In some embodiments, the subject to be treated is a mammalian animal or a human.

In some embodiments, the compound described herein as a mitochondrial uncoupling agent is administered in combination with a second anti-diabetic agent.

In some embodiments, the compound described herein as a mitochondrial uncoupling agent is administered prior to, concomitantly with, or subsequently to administration of the second anti-diabetic agent.

In some embodiments, the second anti-diabetic agent is selected from insulin, insulin analogs, sulfonylureas, biguanides, meglitinides, thiazolidinediones, alpha glucosidase inhibitors, GLP-1 agonists, and DPP-4 inhibitors. In some embodiments, the second anti-diabetic agent is metformin.

In some embodiments, there is provided use of compounds or compositions described herein for treating or preventing metabolic disease or disorder, wherein the disease or disorder is obesity, alcoholic fatty liver disease, non-alcoholic fatty liver disease, or dyslipidemia. In some embodiments, the metabolic disease or disorder is obesity or obesity-related complications.

In another aspect there is provided a method of using a therapeutic effective amount of a compound described herein as mitochondrial uncoupling agent for treating or preventing cancer in a subject.

In some embodiments, the compound described herein as a mitochondrial uncoupling agent is administered orally, intravenously, subcutaneously, intramuscularly, transdermally, intraperitoneally, or other pharmacologically acceptable routes.

In some embodiments, the compound described herein is in the form of pharmacologically acceptable formulations and dosages.

In another aspect there is provided a new approach of using the compounds described herein as mitochondrial uncoupling agents for long-term chronic disease management by reducing plasma glucose. In some embodiments, the metabolic disease or disorder for long-term disease management includes obesity, obesity-related complications, and type 2 diabetes.

In another aspect, there is provided use of the compound described herein as a mitochondrial uncoupling agent in manufacture of a medicament for treatment of metabolic diseases and cancer.

DETAILED DESCRIPTION OF THE INVENTION

Metabolic diseases defined in this patent application are a family of diseases characterized by symptoms of abnormal glucose and/or lipid metabolism, which share common causal factors of abnormal accumulation of intracellular lipid in cells of various tissues and insulin resistance. More specifically, the referred metabolic diseases include but not limited to: obesity (excessive fat accumulation in cells of adipose tissue), metabolic syndrome (insulin resistance in peripheral tissues, usually caused by ectopic fat accumulation in cells of liver, muscle, or adipose tissue), type 2 diabetes (insulin resistance in peripheral tissues usually caused by ectopic fat accumulation in cells of liver, muscle, or adipose tissue, and hyperglycemia caused by insulin resistance), the various known complications caused by type 2 diabetes, alcoholic fatty liver disease (ectopic lipid accumulation in liver cells), the various stages of non-alcoholic liver fatty liver disease (or NAFLD, caused by ectopic lipid accumulation in liver cells, the stages include hepatosteatosis, non-alcoholic steatohepatitis (NASH), cirrhosis, and NAFLD induced hepatocellular carcinoma (HCC)), and the various types of dyslipidemia (ectopic accumulation of lipid in cells of liver, muscle, heart, as a result of redistribution of lipid from adipose tissue to other tissues). Mitochondrial uncouplers, which reduce energy efficiency and boost futile lipid oxidation, would effectively reduce cellular accumulation of lipid. Moreover, recent studies have demonstrated that ectopic intracellular accumulation of lipid in liver, muscle, as well as excessive accumulation of lipid in adipose tissue are the fundamental cause of insulin resistance of the various forms of metabolic diseases (Samuel V. T., et al., Lancet, 2010, 375:2267-77). Indeed, more recent studies have shown that chemical mitochondrial uncouplers are efficacious in preventing and treating metabolic diseases (Perry R J, Zhang D, Zhang X M, Boyer J L, Shulman G I., Science 2015 Mar. 13; 347(6227):1253-6.), leading to: (1) reduction of lipid accumulation in various tissues, including adipose tissue, (2) reduction in insulin resistance, (3) reduction in blood glucose concentrations, (4) improvement in glycemic control and slowdown in disease progression. Importantly, using mitochondrial uncouplers for treating metabolic diseases has a number of appealing features; for example, since they correct the cause of insulin resistance (ectopic lipid accumulation), such an approach may provide a cure for some metabolic diseases. Despite the exciting advantage, currently no uncoupler drugs have been approved for clinical use or in clinical trials. Discovery of novel chemical mitochondrial uncouplers with a combination of favorable pharmamacokinetic and pharmacodynamic properties would be critical for developing mitochondrial uncoupling drugs for treatment of the above-mentioned metabolic diseases.

Cancer is a family of diseases characterized by uncontrolled growth and proliferation of cells of various tissue types, resulted from a combination of genetic mutations in oncogenes and tumor suppressor genes. It is well-accepted that one requirement of tumorigenesis is the alteration of cell metabolism. For rapid proliferation and growth, cancer cells require not only energy but also the building blocks (metabolic intermediates) for biosynthesis of macromolecules such as DNA and RNA. Metabolism in cancer cells is changed in such a way it could support both the energy need and the enormous need of the various metabolic intermediates (building blocks) for biosynthesis of macromolecules Wander Heiden M G, Cantley L C, Thompson C B. Science. 2009 May 22; 324(5930):1029-33.). As a result, most cancers exhibit a unique cellular metabolic pattern called the Warburg effect, or aerobic glycolysis, which prevents the complete oxidation of glucose or lipid and allows for production of glucose metabolites for biosynthesis of macromolecules (Vander Heiden M G, Cantley L C, Thompson C B. Science. 2009 May 22; 324(5930):1029-33.). Mitochondrial uncoupling reduces energy efficiency thereby undermines the energy requirement of cancer cells. In addition, mitochondrial uncoupling promotes the complete mitochondrial oxidation of glucose and lipid, thereby diminishes the production of metabolic intermediates essential for biosynthesis of macromolecules required for cell proliferation. Moreover, mitochondrial uncoupling could lead to AMPK activation, a known event for inhibiting cell growth. Indeed, prior documents showed that mitochondrial uncouplers exhibit anti-cancer activities (US20130231312). Targeting cancer cells through mitochondrial uncoupling would deprive energy as well as biosynthetic metabolic intermediates that are absolutely essential for cancer cell growth and proliferation. Again, despite the appealing features of the new anti-cancer strategy, currently no mitochondrial uncoupling drug has been approved for cancer treatment or in clinical trial. Discovery of new types of chemical mitochondrial uncouplers with a combination of favorable pharmacokinetic and pharmacodynamic properties is critical for treating the various types of cancers.

Various embodiments provide compounds with mitochondrial uncoupling activity. These compounds could be used for the prevention and treatment of metabolic diseases and cancer, including, but not limited to, obesity, metabolic syndrome, type 2 diabetes, alcoholic fatty liver disease, non-alcoholic fatty liver diseases, dyslipidemia, primary cancer of various tissue origins, and metastatic cancer.

In one aspect there is provided a compound of formula (I) or a pharmaceutically acceptable salt, solvate, or prodrug thereof, wherein:

(I)

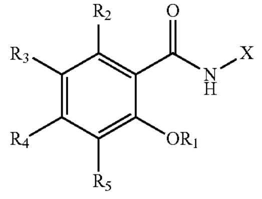

$R_1$ is H, $PO(OH)_2$, $PO_3M_2$, $PO(OH)R_a$, $PO(OM)R_a$, $PO(R_a)_2$, $C(O)R_a$, or $B(OH)_2$ wherein M is a metal cation (e.g. $Na^+$, $K^+$, $Mg^{2+}$, $Ca^{2+}$), an organic amine (e.g. positively charged organic amines such as a protonated amine or a quaternary ammonium cation), or a derivative thereof;

$R_2$, $R_3$, $R_4$, and $R_5$ are each independently selected from the group consisting of H, halogen, $CF_3$, $SF_3$, CN, $NO_2$, alkyl, haloalkyl, aryl, COOH, $COOR_a$, and $CONHR_a$;

each $R_a$ is independently selected from H, alkyl, aryl, alkoxy, aryloxy, alkoxyalkyl, amino, alkylamino and alkylcarbonyloxy-alkyl; wherein each alkyl, aryl, alkoxy, aryloxy, or alkoxyalkyl is optionally substituted with one, two, three or four substituents each selected from hydroxy, cyano, nitro, halogen, carbonyl, $C_{1-8}$ alkyl, $C_{2-8}$ alkenyl, $C_{2-8}$ alkynyl, hydroxy-$C_{1-8}$ alkyl, halo-$C_{1-8}$ alkyl, $C_{1-8}$ alkoxy, halo-$C_{1-8}$alkoxy, amino, $C_{1-8}$ alkyl-amino, amino-$C_{1-8}$ alkyl, $C_{1-8}$ alkyl-amino-$C_{1-8}$ alkyl, $C_{1-8}$alkoxy-$C_{1-8}$ alkyl, $C_{1-8}$ alkylthio, $C_{1-8}$ alkyl-carbonyl, $C_{1-8}$ alkoxy-carbonyl, $C_{1-8}$alkylcarbonyloxy or amino-sulfonyl.

X is a $C_{5-10}$heteroaryl or a monocyclic or bicyclic $C_{6-10}$aryl. The heteroaryl comprises at least one nitrogen and optionally one oxygen or one sulfur atom, and said heteroaryl is optionally substituted with one or more $R_b$. The $C_{6-10}$ aryl is optionally substituted with one or more $R_b$.

Each $R_b$ is independently selected from the group consisting of H, halogen, CN, $NO_2$, $CO_2H$, $CO_2R_a$, $CF_3$, $OCF_3$, $SF_3$, $C_{6-10}$ oaryl, alkyl, haloalkyl, $CONHR_a$, and $C{=}NR_c(N(R_d)_2)$.

Each $R_c$ is independently selected from the group consisting of H, CN, O-alkyl, $NH_2$, mono-alkyl substituted amino, and di-alkyl substituted amino.

Each $R_d$ is independently selected from the group consisting of H and alkyl, wherein said alkyl is optionally substituted with halogen, CN, $NO_2$, $CO_2H$, $CO_2R_a$, $CF_3$, $OCF_3$, $SF_3$, $C_{6-10}$ aryl, or $CONHR_a$ Exemplary embodiments of alkyl as a substituent include $C_{1-6}$ alkyl, $C_{1-8}$ alkyl, $C_{1-10}$ alkyl, and $C_{1-20}$ alkyl. Aryl and heteroary groups as substituents can be $C_{6-10}$ aryl or $C_{5-10}$ heteroaryl.

In some embodiments, X is a 5, 6, 9, or 10-membered substituted or unsubstituted heteroaryl containing at least one nitrogen and optionally sulfur and/or oxygen and is selected from the group consisting of imidazole, pyrrole, pyrazole, tetrazole, oxazole, thiazole, pyridine, pyrimidine, pyrazine, pyridazine, triazine, indazole, purine, benzimidazole, benzoxazole, benzothiazole, quinoline, isoquinoline, and quinazaline;

In some embodiments, at least three of $R_2$, $R_3$, $R_4$, and $R_5$ are H. In some embodiments, "alkyl" group is a carbon chain, straight or branched, having 1 to 8 carbons.

In some embodiments, X is a 9-membered ring having the structure:

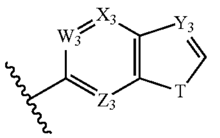

or

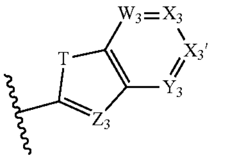

wherein T is O, S, or $NR_a$; $W_3$, $X_3$, $X_3'$, $Y_3$, and $Z_3$ are each independently $CR_b$ or N;
each $R_a$ is independently selected from the group consisting of H, alkyl, aryl, alkoxy, aryloxy, alkoxyalkyl, amino, alkylamino, and alkyl-carbonyloxy-alkyl;
each $R_b$ is independently selected from the group consisting of H, halogen, CN, $NO_2$, $CO_2H$, $CO_2R_a$, $CF_3$, $OCF_3$, $SF_3$, $C_{6-10}$aryl, alkyl, haloalkyl, $CONHR_a$, and $C{=}NR_c(N(R_d)_2)$;
each $R_c$ is independently selected from the group consisting of H, CN, O-alkyl, $NH_2$, mono-alkyl substituted amino, and di-alkyl substituted amino; and
each $R_d$ is independently selected from the group consisting of H and alkyl, wherein said alkyl is optionally substituted with halogen, CN, $NO_2$, $CO_2H$, $CO_2R_a$, $CF_3$, $OCF_3$, $SF_3$, $C_{6-10}$aryl, or $CONHR_a$; and
provided that said 9-membered ring contains at least one nitrogen and is not indole.

In some embodiments, X is a six-membered heteroaryl having the structure:

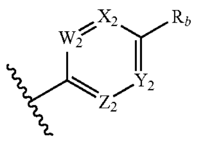

wherein two of $W_2$, $X_2$, $Y_2$ and $Z_2$ are N, the other two are $CR_b$, and $W_2$ and $Z_2$ are not both N;
each $R_a$ is independently selected from the group consisting of H, alkyl, aryl, alkoxy, aryloxy, alkoxyalkyl, amino, alkylamino, and alkyl-carbonyloxy-alkyl; and
each $R_b$ is independently selected from the group consisting of H, halogen, CN, $NO_2$, $CO_2H$, $CO_2R_a$, $CF_3$, $OCF_3$, $SF_3$, $C_{6-10}$ aryl, alkyl, haloalkyl, $CONHR_a$, and $C{=}NR_c(N(R_d)_2)$;
each $R_c$ is independently selected from the group consisting of H, CN, O-alkyl, $NH_2$, mono-alkyl substituted amino, and di-alkyl substituted amino;
each $R_d$ is independently selected from the group consisting of H and alkyl, wherein said alkyl is optionally substituted with halogen, CN, $NO_2$, $CO_2H$, $CO_2R_a$, $CF_3$, $OCF_3$, $SF_3$, $C_{6-10}$ aryl, or $CONHR_a$; and
provided that when said six-membered heteroaryl is a pyrazine, $R_b$ is selected from halogen, CN, $NO_2$, $CO_2H$, $CO_2R_a$, $CF_3$, $OCF_3$, $SF_3$, $C_{6-10}$ aryl, alkyl, haloalkyl, $CONHR_a$, and $C{=}NR_c(N(R_d)_2)$.

In some embodiments, X is a pyridine ring substituted with one or more $R_b$, wherein each $R_b$ is independently selected from the group consisting of halogen, CN, $NO_2$, $CO_2H$, $CO_2R_a$, $CF_3$, $OCF_3$, $SF_3$, $C_{6-10}$ aryl, alkyl, haloalkyl, $CONHR_a$, and $C{=}NR_c(N(R_d)_2)$, provided that said halogen is not substituted ortho to the ring nitrogen;

each $R_a$ is independently selected from the group consisting of H, alkyl, aryl, alkoxy, aryloxy, alkoxyalkyl, amino, alkylamino, and alkyl-carbonyloxy-alkyl;

each $R_c$ is independently selected from the group consisting of H, CN, O-alkyl, $NH_2$, mono-alkyl substituted amino, and di-alkyl substituted amino; and each $R_d$ is independently selected from the group consisting of H and alkyl, wherein said alkyl is optionally substituted with halogen, CN, $NO_2$, $CO_2H$, $CO_2R_a$, $CF_3$, $OCF_3$, $SF_3$, $C_{6-10}$aryl, or $CONHR_a$.

In some embodiments of formula (I), X is a 5-membered ring having the structure:

(I-a)

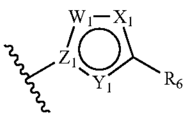

or (I-b)

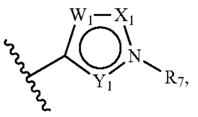

wherein $W_1$, $X_1$, and $Y_1$ are each independently CR, N, O, or S; $Z_1$ is $CR_b$ or N; provided that the 5-membered rings contain at least one nitrogen atom;

Each $R_b$ is independently as described above or void;

Each $R_6$ is independently selected from the group consisting of halo, CN, $NO_2$, $CO_2H$, $CO_2R_a$, and $CONHR_a$; and Each $R_7$ is independently selected from the group consisting of H, CN, $NO_2$, $CO_2R_a$, and $CONHR_a$.

The circle in formula I-a and I-b represents the aromaticity character of the ring. The specific positions of double bonds may vary depending on specific groups of $W_1$, $X_1$, $Y_1$, and $Z_1$. Examples of I-a and I-b include:

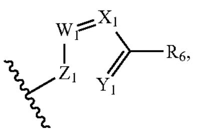

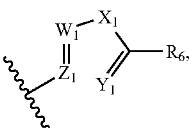

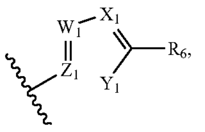

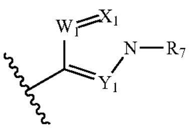

Another aspect of the invention provides a compound of formula (I) having the structure:

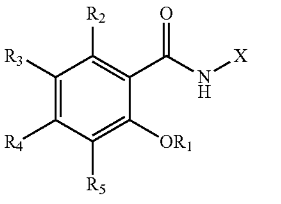

or a pharmaceutically acceptable salt, solvate, or prodrug thereof, wherein:

$R_1$ is selected from the group consisting of $PO(OH)_2$, $PO_2(OH)M$, $PO_3M_2$, $PO(OH)R_a$, $PO(OM)R_a$, or $PO(R_a)_2$, and $C(O)R_e$, wherein M is a metal cation or an organic amine;

$R_2$, $R_3$, $R_4$, and $R_5$ are each independently selected from the group consisting of H, halogen, $CF_3$, $SF_3$, CN, $NO_2$, alkyl, haloalkyl, aryl, COOH, $COOR_a$, and $CONHR_a$;

X is a monocyclic or bicyclic $C_{6-10}$aryl optionally substituted with one or more $R_b$;

each $R_a$ is independently selected from the group consisting of H, alkyl, aryl, alkoxy, aryloxy, alkoxyalkyl, amino, alkylamino, and alkyl-carbonyloxy-alkyl;

each $R_b$ is independently selected from the group consisting of H, halogen, CN, $NO_2$, $CO_2H$, $CO_2R_a$, $CF_3$, $OCF_3$, $SF_3$, $C_{6-10}$aryl, alkyl, haloalkyl, $CONHR_a$, and $C{=}NR_c(N(R_d)_2)$;

each R, is independently selected from the group consisting of H, CN, O-alkyl, $NH_2$, mono-alkyl substituted amino, and di-alkyl substituted amino;

each $R_d$ is independently selected from the group consisting of H and alkyl, wherein said alkyl is optionally substituted with halogen, CN, $NO_2$, $CO_2H$, $CO_2R_a$, $CF_3$, $OCF_3$, $SF_3$, $C_{6-10}$ aryl, or $CONHR_a$; and $R_e$ is $NH_2$ optionally substituted with one or two alkyl groups.

In another aspect there is provided a compound selected from:

N-(5-Bromopyrazin-2-yl)-5-chloro-2-hydroxybenzamide,
5-Chloro-N-(5-cyanopyrazin-2-yl)-2-hydroxybenzamide,
5-Chloro-N-(3-chloro-5-cyanopyrazin-2-yl)-2-hydroxybenzamide,
5-chloro-2-hydroxy-N-(pyrimidin-5-yl)benzamide,
5-Chloro-N-(2,4-dichloropyrimidin-5-yl)-2-hydroxybenzamide,
5-Chloro-N-(2-chloropyrimidin-5-yl)-2-hydroxybenzamide,
5-Chloro-N-(2-cyanopyrimidin-5-yl)-2-hydroxybenzamide,
5-Chloro-2-hydroxy-N-(pyridazin-3-yl)benzamide,
5-Chloro-N-(6-chloropyridazin-3-yl)-2-hydroxybenzamide,
5-Chloro-N-(5-cyanopyridin-2-yl)-2-hydroxybenzamide,
N-(Benzo[d]thiazol-5-yl)-5-chloro-2-hydroxybenzamide,
5-chloro-N-(5-cyanothiazol-2-yl)-2-hydroxybenzamide,
N-(Benzo[d]thiazol-2-yl)-5-chloro-2-hydroxybenzamide,
5-Chloro-N-(4-fluorobenzo[d]thiazol-2-yl)-2-hydroxybenzamide,
4-Chloro-2-((5-cyanopyrazin-2-yl)carbamoyl)phenyl dihydrogen phosphate,
Sodium 4-chloro-2-((5-cyanopyrazin-2-yl)carbamoyl)phenyl phosphate phosphate,
5-Chloro-2-hydroxy-N-(isoquinolin-7-yl)benzamide,
5-Chloro-2-hydroxy-N-(quinoxalin-6-yl)benzamide,
4-Chloro-2-((5-cyanopyrazin-2-yl)carbamoyl)phenyl dimethylcarbamate,
4-chloro-2-((5-cyanopyrazin-2-yl)carbamoyl)phenyl[1,4'-bipiperidine]-1'-carboxylate,
4-chloro-2-((5-cyanopyrazin-2-yl)carbamoyl)phenyl[1,4'-bipiperidine]-1'-carboxylate,
4-Chloro-2-((5-cyanopyrazin-2-yl)carbamoyl)phenyl ethylcarbamate,
5-chloro-N-(6-fluorobenzo[d]thiazol-2-yl)-2-hydroxybenzamide,
4-Chloro-2-((6-fluorobenzo[d]thiazol-2-yl)carbamoyl)phenyl dimethylcarbamate,
5-Chloro-2-hydroxy-N-(4-(trifluoromethyl)benzo[d]thiazol-2-yl)benzamide,
4-chloro-2-((4-(trifluoromethyl)benzo[d]thiazol-2-yl)carbamoyl)phenyl, dimethylcarbamate,
5-chloro-2-hydroxy-N-(6-(trifluoromethyl)benzo[d]thiazol-2-yl)benzamide,
4-chloro-2-((6-(trifluoromethyl)benzo[d]thiazol-2-yl)carbamoyl)phenyl, dimethylcarbamate,
4-chloro-2-((4-fluorobenzo[d]thiazol-2-yl)carbamoyl)phenyl dimethylcarbamate,
4-chloro-2-((2-chloro-4-nitrophenyl)carbamoyl)phenyl dimethylcarbamate,
5-chloro-2-hydroxy-N-(5-(trifluoromethyl)pyrazin-2-yl)benzamide,
5-chloro-N-(6-cyanobenzo[d]thiazol-2-yl)-2-hydroxybenzamide, and a pharmaceutically acceptable salt thereof.

In another aspect there is provided a compound selected from:

4-chloro-2-((2-chloro-4-cyanophenyl)carbamoyl)phenyl ethyl hydrogen phosphate,
4-chloro-2-((2-chloro-4-cyanophenyl)carbamoyl)phenyl dihydrogen phosphate,
sodium 4-chloro-2-((2-chloro-4-cyanophenyl)carbamoyl)phenyl phosphate, and pharmaceutically acceptable salts thereof.

In another aspect there is provided compositions for treatment or prevention of obesity, type 2 diabetes, non-alcoholic or alcoholic fatty liver disease, dyslipidemia, cancer, a related disorder and complication, the composition comprising a compound of the present invention, or a pharmaceutically acceptable salt, solvate, or prodrug thereof. The pharmaceutical composition may comprise one or more compounds of the invention, and biologically active analogs, homologs, derivatives, modifications, and pharmaceutically acceptable salts thereof, and a pharmaceutically acceptable carrier.

The compounds and compositions of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals (e.g. mice, rats, horses, cattle, sheep, dogs, cats, monkeys, etc.), the compounds of the invention are effective for use in humans. The terms "administration of" and or "administering a" compound should be understood to mean providing a compound of the invention or a prodrug of a compound of the invention to the individual in need of treatment.

The compounds and compositions of this invention can be administered at prophylactically effective dosage levels to prevent the above-recited conditions and disorders, as well as to prevent other conditions and disorders characterized by insulin resistance or hyperglycemia.

Pharmaceutical compositions intended for oral use may be prepared according to any method known to the art for the manufacture of pharmaceutical compositions and such compositions may contain one or more agents including for example sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art.

Compositions containing a compound of the invention, or pharmaceutically acceptable salts thereof, can also be prepared in powder or liquid concentrate form.

Pharmaceutically-acceptable base addition salts for compounds described herein can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cyclo alkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of organic (e.g., carboxylic) acids can also be made.

The pharmaceutical compositions described herein may include, as appropriate, one or more additional carrier ingredients such as diluents, buffers, flavoring agents, binders, surface-active agents, thickeners, lubricants, and preservatives (including anti-oxidants). Furthermore, other adjuvants can be included to render the formulation isotonic with the blood of the intended recipient.

The pharmaceutical composition according to the invention can be administered in a wide range of dosage-forms including for example solid dosage forms and liquid dosage forms. Solid dosage forms may include powders, tablets, pills, capsules, suppositories, or dispersible granules. A solid carrier can be one or more substances that function as a diluting agent, flavor additive, solvent, lubricant, suspension agent, binder, preservative, tablet-disintegrating substance or encapsulating material. In powdered form, the carrier may be a finely pulverized solid including lactose, hydroxypropylmethylcellulose and PVP, mixed with an appropriate amount of the active ingredient. Appropriate carriers for powder and tablet forms include for example magnesium carbonate, magnesium stearate, talc, sugar, lactose, pectin, dextrin, stiffeners, gelatins, tragacanth, methylcellulose, and sodium carboxymethylcellulose.

Liquid dosage forms include for example solutions, suspensions, and emulsions. Also included are compositions in solid form that are meant to be converted to liquid form shortly prior to consumption. These forms may include, in addition to the active ingredients, artificial colors, flavors, stabilizers, buffers, natural or artificial sweeteners, dispersing agents, thickeners, dissolving agents and the like.

Solutions or mixtures may be administered directly to the nasal cavity using conventional means, such as drops or sprays. The composition may be produced in individual or multi-dose forms. Multi-dose forms would include a dropper, pipette or atomizer that delivers a predetermined volume of the composition.

The pharmaceutical composition is preferably provided in individual dosage units that contain a suitable amount of the active ingredient. The individual doses may be provided in a package, or as a kit that includes a measuring device, e.g., a device for measuring oral or injectable dosages (i.e., a measuring cup, needle, or syringe). The kit can also include, other materials such buffers, diluents, filters, and package inserts with instructions for use. A label may be present on the on the kit to indicate that the composition is used for a specific therapy, and may also indicate directions for use.

In another aspect there is provided a method of treating or preventing a metabolic disease or disorder in a subject, comprising administering to the subject a therapeutically effective amount of a mitochondrial uncoupling agent or composition described above. Studies on the relationship between the modulation of mitochondrial uncoupling and reduction of lipid accumulation in tissues, insulin resistance, blood-glucose and body-weight control in animals have been reported in the literature (see, for example, WO2012068274, Tao H, Zhang Y, Zeng X, Shulman G I, Jin S. Nat Med. 2014, 20: 1263-1269. Perry R J, Zhang D, Zhang X M, Boyer J L, Shulman G I., Science 2015 Mar. 13; 347(6227):1253-6). Thus, the present invention provides, among others, a method of treating and alleviating the symptoms of obesity (characterized by excessive accumulation of lipid in adipocytes), pre-type 2 diabetes (characterized by insulin resistance usually caused by ectopic accumulation of lipid in cells of liver and muscle), type 2 diabetes (characterized by insulin resistance and hyperglycemia), non-alcoholic fatty liver diseases or alcoholic fatty liver disease (characterized by abnormal accumulation of lipid in liver), dyslipidemia (characterized by abnormal lipid deposit in tissue other than adipose), and complications of the above mentioned metabolic disorders, including, but not limited to, hypertension, cardiovascular diseases, nephropathy, and neuropathy. These diseases or disorders may be caused by dietary, environmental, medical and/or genetic factors. The method of the present invention can also be used for prevention of the above-mentioned metabolic diseases for a subject with risk factors including, but not limited to, dietary, environmental, medical, and genetic predispositions. In addition, the present invention provides a new approach for long-term chronic disease management and longevity management by reducing insulin resistance or reducing glucose levels in the blood.

In some embodiments of this aspect, the metabolic disease or disorder is type 2 diabetes, or related diseases leading to insulin resistance or hyperglycemia.

In some embodiments of this aspect, the metabolic disease or disorder is obesity.

In some embodiments of this aspect, the metabolic disease or disorder is non-alcoholic fatty liver disease, (NAFLD), including nonalcoholic steatohepatitis (NASH) and cirrhosis, or alcoholic fatty liver disease (AFLD). In some embodiments, the metabolic disease or disorder is hepatic steatosis, non-alcoholic steatohepatitis (NASH), cirrhosis, or NAFLD induced hepatocellular carcinoma (HCC).

In some embodiments of this aspect, the metabolic diseases or disorder is complications of type 2 diabetes including but not limited to type 2 diabetes induced hypertension, cardiovascular disease, nephropathy, atherosclerosis, dyslipidemia, retinopathy, neurodegenerative disorders, diabetic heart failure, and neuropathy.

In some embodiments of this aspect, the metabolic disease or disorder is pre-type 2 diabetes.

In some embodiments of this aspect, the metabolic disease or disorder is dyslipidemia.

In some embodiments, the disease to be treated may be a mitochondrial disorder. In some embodiments, the metabolic disorder may be LHON (leber heredity optic neuropathy), MELAS (mitochondrial myopathy, mitochondrial encephalomyopathy, lactic acidosis and stroke-like episodes), MERRF (myoclonic epilepsy and ragged red muscle fiber), Leigh Syndrome, MILS (maternally inherited Leigh Syndrome), NARP (neurogenic muscle weakness, ataxia and retinitis pigmentosa), FBSN (familial bilateral striatal necrosis) or KSS (Kearns Sayre Syndrome).

In some embodiments, the disease to be treated may be a heart disorder. In some embodiments, the heart disorder may be hypertension or cardiovascular disease.

In some embodiments, the disease to be treated may be a central nervous system (CNS) disease. In some embodiments, the CNS disease may be stroke, Alzheimer's, Parkinson's, Huntington's or ALS (amyotropic lateral sclerosis).

In some embodiments, the disease to be treated may be disorders associated with increased ROS (reactive oxygen species) production. Increased ROS has been associated with aging, Alzheimer's disease, Parkinson's disease, Huntington's disease, ALS (amyotropic lateral sclerosis), mitochondrial diseases and cancers.

In some embodiments of this aspect, the compound described herein is used as a veterinarian drug to treat diabetes or a diabetes-associated disease, and the subject is a mammalian animal.

In some embodiments of this aspect, the subject is a human.

In some embodiments of this aspect, the compound of the present invention is administered in combination with a second agent indicated for the above-mentioned disorders or diseases, either concomitant with, prior to, or after the administration of the second agent.

In some embodiments of this aspect, the mitochondrial uncoupling agent is administered in combination with a second anti-diabetic agent.

In some embodiments of this aspect, the second anti-diabetic agent is metformin.

In some embodiments of this aspect, the second anti-diabetic agent is selected from insulin, insulin analogs, sulfonylureas, biguanides, meglitinides, thiazolidinediones, alpha glucosidase inhibitors, GLP-1 agonists, DPP-4 inhibitors, and SGLT2 inhibitors.

In some embodiments of this aspect, the mitochondrial uncoupling agent is administered in combination with a second anti-non alcoholic fatty liver disease agent.

In some embodiments of this aspect, the mitochondrial uncoupling agent is administered in combination with a second anti-alcoholic fatty liver disease agent.

In some embodiments of this aspect, the mitochondrial uncoupling agent is administered in combination with a second anti-dyslipidemia agent.

In some embodiments of this aspect, the mitochondrial uncoupling agent is administered orally, intravenously, subcutaneously, intramuscularly, transdermally, intraperitoneally, or other pharmacologically acceptable routes.

In another aspect the present invention there is provided a method for long-term disease management of a metabolic disease or disorder, comprising administering to a subject in need of such long-term management an effective amount of a compound or a composition described herein.

In another aspect the present invention there is provided use of a compound described above as a mitochondrial uncoupling agent in manufacture of a medicament for treatment of obesity, diabetes, non-alcoholic or alcoholic fatty liver disease, dyslipidemia, or related disorders or complications, including hepatic steatosis, non-alcoholic steatohepatitis (NASH), cirrhosis, or NAFLD induced hepatocellular carcinoma (HCC).

The route of administration can vary depending on the type of compound being administered. In one aspect, the compounds are administered via routes such as oral, topical, rectal, intramuscular, intramucosal, intranasal, inhalation, ophthalmic, and intravenous. The present invention further provides for administration of a compound of the invention as a controlled-release formulation.

In another aspect there is provided a method of treating or preventing cancer in a subject, comprising administering to the subject a therapeutically effective amount of a mitochondrial uncoupling agent or composition described above. Studies on the relationship between mitochondrial uncoupling and cancer have been reported in the literature (see, for example US20130231312). Thus, the present invention provides, among others, a method of preventing and treating cancer, including but not limited to primary cancer and metastatic cancer.

In some embodiments of this aspect, the cancer is primary cancer including but not limited to hepatocellular carcinoma, colorectal carcinoma, pancreatic cancer, breast cancer, prostate cancer, leukemia, lymphoma, melanoma, ovarian cancer, lung cancer.

In some embodiments of this aspect, the cancer is metastatic liver cancer originated from the primary tumor of other tissue types.

In some embodiments of this aspect, the cancer is metastatic lung cancer originated from the primary tumor of other tissue types.

In some embodiments of this aspect, the cancer is metastatic cancer to other sites including intraperitoneal cavity.

In some embodiments of this aspect, the compound described herein is used as a veterinarian drug to treat cancer, and the subject is a mammalian animal.

In some embodiments of this aspect, the subject is a human.

In some embodiments of this aspect, the compound of the present invention is administered in combination with a second anti-cancer agent or anti-cancer regimen, either concomitant with, prior to, or after the administration of the second one.

If desired, the compositions of the present invention may further comprise one or more additional active agents. Where it is appropriate, any of the active agents may be administered in the form of the compound per se, and/or in the form of a salt, polymorph, ester, amide, prodrug, derivative, or the like, provided the salt, polymorph, ester, amide, prodrug or derivative is suitable pharmacologically. Where it is appropriate, salts, esters, amides, prodrugs and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For any active agents that may exist in enantiomeric forms, the active agent may be incorporated into the present compositions either as the racemate or in enantiomerically enriched form.

The dosage of the active compound(s) being administered will depend on the condition being treated, the particular compound, and other clinical factors such as age, sex, weight, and health of the subject being treated, the route of administration of the compound(s), and the type of composition being administered (tablet, gel cap, capsule, solution, suspension, inhaler, aerosol, elixir, lozenge, injection, patch, ointment, cream, etc.). It is to be understood that the present invention has application for both human and animal use. The amount of the compound, or an active salt or derivative thereof, required for use in treatment will be ultimately at the discretion of the attendant physician or clinician.

As described above, the compounds of the invention are useful for the prevention, treatment, control, amelioration, or reduction of risk of the diseases, disorders and conditions noted herein. The dosage of the compound as an active ingredient in the compositions of this invention may be varied so that a suitable dosage form is obtained. The active ingredient may be administered to patients (animals and human) in need of such treatment in dosages that will provide optimal pharmaceutical efficacy. The selected therapeutically effective dosage depends upon the desired therapeutic effect, on the route of administration, and on the duration of the treatment. The therapeutically effective dose will vary from patient to patient depending upon the nature and severity of disease, the patient's weight, special diets then being followed by a patient, concurrent medication, and other factors which those skilled in the art will recognize. Generally, pharmaceutical compositioin of the present invention having an active ingredient in therapeutically effective dosage levels of between 0.001 to 100 mg/kg of body weight daily are administered to the patient, e.g., humans and elderly humans. The therapeutically effective dosage range will generally be about 0.5 mg to 10 g per patient per day which may be administered in single or multiple doses. In some embodiments, the therapeutically effective dosage range will be about 0.5 mg to 2500 mg per patient per day; in some embodiments about 0.5 mg to 200 mg per patient per day; in some embodiments about 0.5 mg to 500 mg per patient per day; in some embodiments about 0.5 mg to 1000 mg per patient per day; in some embodiments about 1 mg to 250 mg per patient per day; and in yet some other embodiments about 5 mg to 50 mg per patient per day. The pharmaceutical composition may be provided in a formulation containing a therapeutically effective amount of, for example, about 1 mg, 5 mg, 10 mg, 25 mg, 50 mg, 100 mg, 200 mg, 250 mg, 500 mg, 1000 mg, 1500 mg, or 2000 mg of the active ingredient. For oral administration, the compositions may be provided in the form of tablets containing 1.0 to 2000 milligrams of the active ingredient, such as 1, 5, 10, 15, 20, 25, 50, 75, 100, 150, 200, 250, 300, 400, 500, 600, 750, 800, 900, 1000 and 2000 milligrams of the active ingredient for the symptomatic adjustment of the dosage to the patient to be treated. The compounds or pharmaceutical compositions may be administered on a regimen of 1 to 4 times per day, such as once, twice, or three times per day.

Compounds of the present invention may have prodrug forms. Any compound that will be converted in vivo to provide the bioactive agent is a prodrug within the scope and spirit of the invention. Various forms of prodrugs are well known in the art (see, for example, Medicinal Chemistry: Principles and Practice, F. D. King, ed., The Royal Society of Chemistry, Cambridge, UK, 1994; Hydrolysis in Drug and Prodrug Metabolism. Chemistry, Biochemistry and Enzymology, B. Testa, J. M. Mayer, VCHA and Wiley-VCH, Zurich, Switzerland, 2003; The Practice of Medicinal Chemistry, C. G. Wermuth, $2^{nd}$ ed., Academic Press, San Diego, Calif., 1999).

In some embodiments, a prodrug of the compounds of the present invention may take the form of a carbamate. For instance, a compound of formula (I) may have $R_1$ as $C(O)R_a$ wherein $R_a$ is amino ($—NH_2$), alkylamino, or arylamino. The alkylamino may be mono-substituted or di-substituted alkylamino groups. In some embodiments, the alkyl group has 1-10 carbons. Non-limiting examples include $—NHCH_3$, $—NHCH_2CH_3$, $—NH\ CH_2CH_2CH_3$, $—N(CH_3)_2$, and $—N(CH_2CH_3)_2$.

Definitions

The articles "a" and "an" as used herein mean "one or more" or "at least one," unless otherwise indicated. That is, reference to any element of the present invention by the indefinite article "a" or "an" does not exclude the possibility that more than one of the element is present.

As used herein, the term "alkyl" is intended to include both branched and straight-chain saturated aliphatic hydrocarbon groups having the specified number of carbon atoms. For example, "$C_1$-$C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" or "$C_{1-6}$ alkyl" denotes alkyl having 1 to 6 carbon atoms. Alkyl group can be unsubstituted or substituted with at least one hydrogen being replaced by another chemical group. Examples of alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). An alkylamino group includes mono-substituted alkyl amino group (e.g. NHR, R=alkyl) and di-substituted alkyl amino group (e.g. NRR, R=alkyl).

"Alkenyl" is intended to include hydrocarbon chains of either straight or branched configuration having the specified number of carbon atoms and one or more, preferably one to three, carbon-carbon double bonds that may occur in any stable point along the chain. For example, "$C_2$-$C_6$ alkenyl" or "$C_{2-6}$ alkenyl" (or alkenylene), are intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

Alkynyl" is intended to include hydrocarbon chains of either straight or branched configuration having one or more, preferably one to three, carbon-carbon triple bonds that may occur in any stable point along the chain. For example, "$C_2$-$C_6$ alkynyl" is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$-$C_6$ alkoxy" or "$C_{1-6}$ alkoxy" (or alkyloxy), is intended to include $C_1$, $C_2$, $C_3$, $C_4$, $C_5$, and $C_6$, alkoxy groups. Examples of alkoxy groups include, but are not limited to, methoxy, ethoxy, propoxy (e.g., n-propoxy and isopropoxy), and t-butoxy.

The term "halo" or "halogen" refers to fluoro, chloro, bromo, and iodo. "Haloalkyl" is intended to include both branched and straight-chain saturated aliphatic hydrocarbon groups having the specified number of carbon atoms, substituted with one or more halogens. Examples of haloalkyl include, but are not limited to, fluoromethyl, difluoromethyl, trifluoromethyl, and trichloromethyl.

"Haloalkoxy" or "haloalkyloxy" represents a haloalkyl group as defined above with the indicated number of carbon atoms attached through an oxygen bridge. For example, "$C_1$-$C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, trichloromethoxy, and 2,2,2-trifluoroethoxy.

"Aryl" groups refer to monocyclic or polycyclic aromatic hydrocarbons, including, for example, phenyl, and naphthyl. "$C_6$-$C_{10}$ aryl" or "$C_{6-10}$ aryl" refers to phenyl and naphthyl. Unless otherwise specified, "aryl", "$C_6$-$C_{10}$ aryl," "$C_{6-10}$ aryl," or "aromatic residue" may be unsubstituted or substituted with 1 to 5 groups selected from —OH, —$OCH_3$, —Cl, —F, —Br, —I, —CN, —$NO_2$, —$NH_2$, —$NH(CH_3)$, —$N(CH_3)_2$, —$CF_3$, —OCF3, —$C(O)CH_3$, —$SCH_3$, —$S(O)CH_3$, —$S(O)_2CH_3$, —$CH_3$, —$CH_2CH_3$, —$CO_2H$, and —$CO_2CH_3$.

The term "benzyl," as used herein, refers to a methyl group on which one of the hydrogen atoms is replaced by a phenyl group, wherein said phenyl group may optionally be substituted by one to five, preferably one to three, substituents independently selected from methyl, trifluoromethyl (—$CF_3$), hydroxyl (—OH), methoxy (—$OCH_3$), halogen, cyano (—CN), nitro (—$NO_2$), —$CO_2$Me, —$CO_2$Et, and —$CO_2$H. Representative examples of benzyl group include, but are not limited to, $PhCH_2$—, 4-MeO—$C_6H_4CH_2$—, 2,4,6-tri-methyl-$C_6H_2CH_2$—, and 3,4-di-Cl—$C_6H_3CH_2$—.

A "compound," as used herein, refers to any type of substance or agent that is commonly considered a drug or a candidate for use as a drug, as well as combinations and mixtures of the above. When referring to a compound of the invention, and unless otherwise specified, the term "compound" is intended to encompass not only the specified molecular entity but also its pharmaceutically acceptable, pharmacologically active analogs, including, but not limited to, salts, polymorphs, esters, amides, prodrugs, adducts, conjugates, active metabolites, and the like, where such modifications to the molecular entity are appropriate.

As used herein, a "derivative" of a compound refers to a chemical compound that may be produced from another compound of similar structure in one or more steps. Non-limiting examples include replacement of H by an alkyl, acyl, or amino group.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

The terms "formula" and "structure" are used interchangeably herein.

As used herein, the term "heteroaryl" is intended to mean stable monocyclic and polycyclic aromatic hydrocarbons that include at least one heteroatom ring member, such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Unless otherwise specified, heteroaryl groups may be unsubstituted or substituted with 1 to 5 groups selected from —OH, —$OCH_3$, —Cl, —F, —Br, —I, —CN, —$NO_2$, —$NH_2$, —$NH(CH_3)$, —$N(CH_3)_2$, —$CF_3$, —OCF3, —$C(O)CH_3$, —$SCH_3$, —$S(O)CH_3$, —$S(O)_2CH_3$, —$CH_3$, —$CH_2CH_3$, —$CO_2H$, and —$CO_2CH_3$. The nitrogen atom is substituted or unsubstituted (i.e., N or NR wherein R is H or another substituent, if defined). The nitrogen and sulfur heteroatoms may optionally be oxidized (i.e., N→0 and $S(O)_p$, wherein p is 0, 1 or 2).

The term, "mitochondrial uncoupling", also referred to as "uncoupling", refers to the process whereby protons enter the mitochondrial matrix via a pathway independent of ATP synthase and thereby uncouple nutrient oxidation from ATP production. This process can be pharmacologically induced by small molecule mitochondrial protonophores, which directly shuttle protons across the mitochondrial inner membrane into the matrix. The primary pathway for energy production in aerobic cells involves the oxidation of nutrients (including fats, carbohydrates, and amino acids) in mitochondria, which promotes the efflux of protons out of the mitochondrial matrix. This process creates a pH and electrochemical gradient across the mitochondrial inner membrane. Protons normally re-enter the mitochondrial matrix via ATP synthase, which results in ATP production. Protons can also re-enter the mitochondrial matrix via pathways independent of ATP synthase, which 'uncouples' nutrient oxidation and proton efflux from ATP production.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, $18^{th}$ Edition, Mack Publishing Company, Easton, Pa., 1990, the disclosure of which is hereby incorporated by reference.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate.

The term "subject" as used herein is intended to include human and non-human animals. Non-human animals includes all vertebrates, e.g. mammals and non-mammals, such as non-human primates, sheep, dogs, cats, cows, horses, chickens, amphibians, and reptiles, although mammals are preferred, such as non-human primates, sheep, dogs, cats, cows and horses. Preferred subjects include human patients in need of enhancement of an immune response. The methods are particularly suitable for treating human patients having a disorder that can be treated by augmenting the immune response.

The term "treating" or "treatment" as used herein refers to administration of a compound or agent to a subject who has a disorder or is at risk of developing the disorder with the purpose to cure, alleviate, relieve, remedy, delay the onset of, prevent, or ameliorate the disorder, the symptom of the disorder, the disease state secondary to the disorder, or the predisposition toward the disorder.

EXAMPLES

Processes for preparing compounds of the present invention, such as formulas I or I-a, or for preparing intermediates useful for preparing compounds of formula I or other formulas of the invention are provided as further embodiments of the invention or are known in the art. While the following text may exemplify specific compounds and corresponding routes of synthesis, it is not intended to limit the scope of the invention to such particular reference or examples. Various modifications may be made by those skilled in the art, in view of practical and economic considerations, such as the source of the agents and specific conditions of reactions.

1

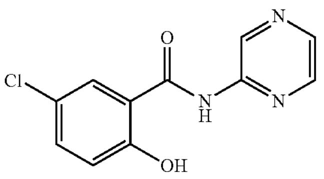

5-Chloro-2-hydroxy-N-(pyrazin-2-yl)benzamide (1)

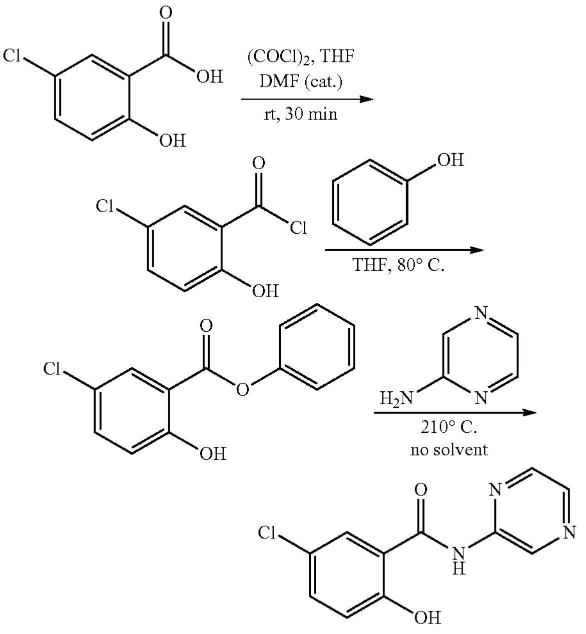

This compound is known and the preparation herein was adapted from the literature procedure (Farmaco, 2005, vol. 60, #5 p. 399-408).

5-Chlorosalicyclic acid (1.0389 g, 6.020 mmol) was dissolved in THF (15.0 mL), followed by the addition of catalytic amount of DMF (20 μL) and oxalyl chloride (0.62 mL, 7.224 mmol) respectively. The reaction was allowed to stir at rt for 30 min and then concentrated in vacuo. The residue was re-dissolved in THF (10.0 mL) followed by addition of phenol (510 mg, 5.418 mmol). The reaction was heated to 80° C. and stirred for 14 hours before it was concentrated. The residue was purified via silica gel column chromatography to yield the known compound phenyl 5-chloro-2-hydroxybenzoate (213.0 mg, 16% yield). The resulting phenyl 5-chloro-2-hydroxybenzoate (213.0 mg, 0.857 mmol) was mixed with aminopyrazine (68.0 mg, 0.714 mmol) and heated to 215° C. The melting mixture was stirred for 25 minutes and cooled back to P. The residue was purified via silica gel column chromatography to yield 5-chloro-2-hydroxy-N-(pyrazin-2-yl)benzamide 1 (10.0 mg, 6% yield). $^1$H NMR (300 MHz, Chloroform-d) δ 9.66 (d, J=1.5 Hz, 1H), 8.90 (s, 1H), 8.49 (dt, J=2.7, 0.5 Hz, 1H), 8.36-8.30 (m, 1H), 7.69 (d, J=2.5 Hz, 1H), 7.47 (ddd, J=8.9, 2.5, 0.6 Hz, 1H), 7.04 (dd, J=8.9, 0.6 Hz, 1H). MS (ESI) exact mass calculated for [M+H] (C11H9ClN3O2) requires m/z 250.0, found m/z 249.9.

2

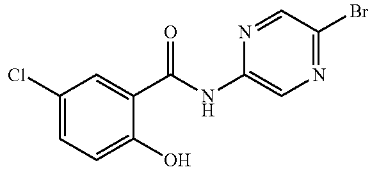

N-(5-Bromopyrazin-2-yl)-5-chloro-2-hydroxybenzamide (2)

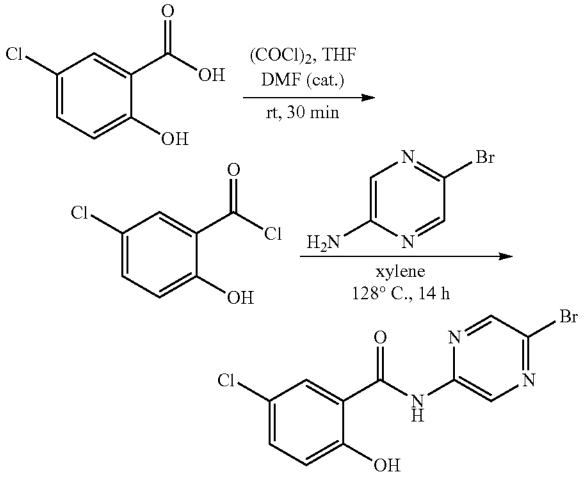

5-Chlorosalicyclic acid (539.0 mg, 3.123 mmol) was dissolved in THF (10.0 mL), followed by the addition of catalytic amount of DMF (20 μL) and oxalyl chloride (0.32 mL, 3.748 mmol) respectively. The reaction was allowed to stir at rt for 30 min and then concentrated in vacuo. The residue was re-dissolved in xylene (7.0 mL) followed by the addition of 5-bromopyrazin-2-amine (435.0 mg, 2.498 mmol). The mixture was heated to 128° C. and stirred for 14 hours before it was brought back to P. The solvent was removed in vacuo and the resulting residue was purified via silica gel column chromatography to yield N-(5-bromopyrazin-2-yl)-5-chloro-2-hydroxybenzamide 2 (15.0 mg, 2% yield). $^1$H NMR (300 MHz, Chloroform-d) δ 11.40 (s, 1H), 9.42 (t, J=1.2 Hz, 1H), 8.52 (s, 1H), 8.36 (d, J=1.4 Hz, 1H), 7.58 (d, J=2.5 Hz, 1H), 7.52-7.44 (m, 1H), 7.05 (d, J=8.9 Hz, 1H). MS (ESI) exact mass calculated for [M+H] (C11H8BrClN3O2) requires m/z 327.9, found m/z 328.0.

3

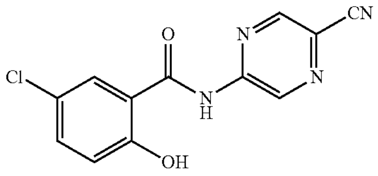

5-Chloro-N-(5-cyanopyrazin-2-yl)-2-hydroxybenzamide (3)

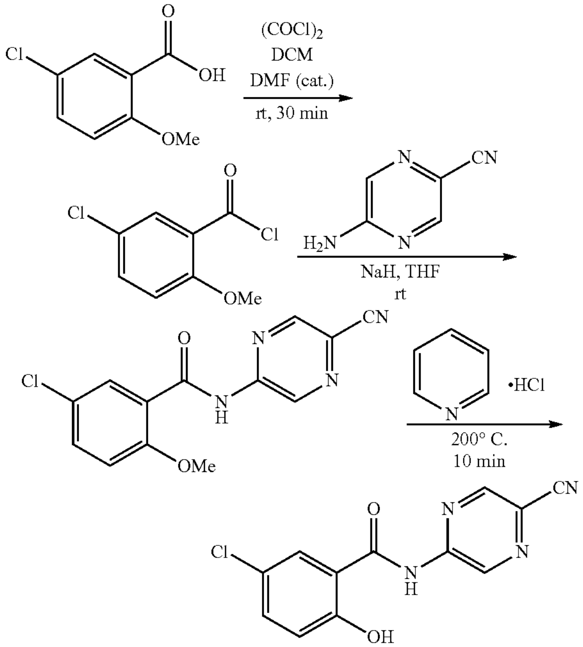

5-chloro-2-methoxybenzoic acid (370.0 mg, 1.981 mmol) was dissolved in THF (10.0 mL), followed by the addition of catalytic amount of DMF (20 μL) and oxalyl chloride (0.20 mL, 2.377 mmol) respectively. The reaction was allowed to stir at rt for 30 min, concentrated in vacuo, and the residue was re-dissolved in THF (10.0 mL). In another flask, 5-aminopyrazine-2-carbonitrile (170.0 mg, 1.415 mmol) was dissolved in THF (5.0 mL) followed by addition of NaH (85.0 mg, 2.123 mmol, 60% in mineral oil). The mixture was stirred for 10 minutes before it was added to the flask containing the freshly prepared acid chloride dropwise at rt. The reaction was stirred at rt for 30 min before silica gel was added to quench the reaction. Solvent was evaporated and the resulting residue was purified via silica gel column chromatography to yield 5-chloro-N-(5-cyanopyrazin-2-yl)-2-methoxybenzamide (40.0 mg, 10% yield) which was mixed with pyridinium chloride (550.0 mg). The mixture was heated to 200° C., stirred for 10 minutes and cooled down to rt. The resulting solid was dissolved in water and extracted with ethyl acetate. The organic layer was concentrated in vacuo and the residue was purified via silica gel column chromatography to yield 5-chloro-N-(5-cyanopyrazin-2-yl)-2-hydroxybenzamide 3 (27.5 mg, 72% yield). $^{1}$H NMR (300 MHz, Acetone-$d_6$) δ 9.70 (d, J=1.5 Hz, 1H), 8.90 (d, J=1.5 Hz, 1H), 8.16 (d, J=2.7 Hz, 1H), 7.59-7.51 (m, 1H), 7.17 (d, J=8.8 Hz, 1H). MS (ESI) exact mass calculated for [M+H] (C12H8ClN4O2) requires m/z 275.0, found m/z 275.1.

4

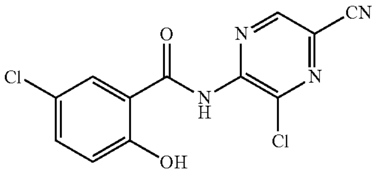

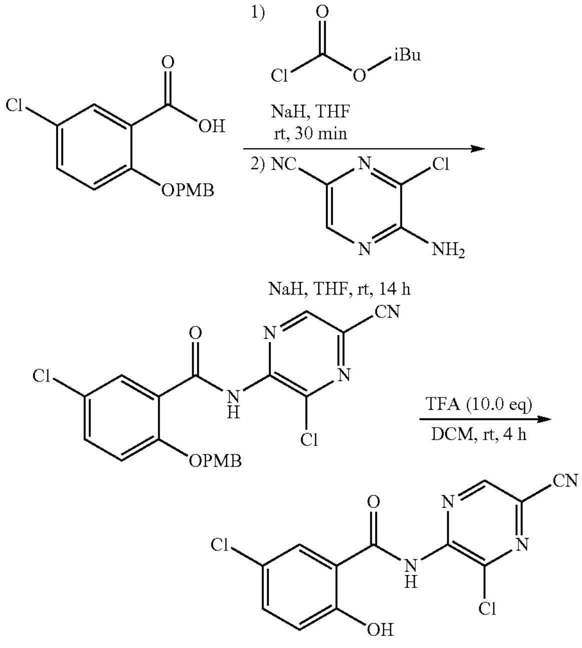

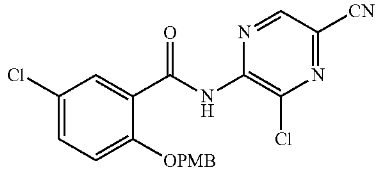

5-Chloro-N-(3-chloro-5-cyanopyrazin-2-yl)-2-((4-methoxybenzyl)oxy)benzamide 5-chloro-2-((4-methoxybenzyl)oxy)benzoic acid (96.0 mg, 0.328 mmol) was dissolved in THF (5.0 mL) followed by addition of NaH (16.0 mg, 60% in mineral oil) and chloro isobutylformate (52 μL) at rt. The mixture was stirred at rt for 30 minutes. In another flask, 5-amino-6-chloropyrazine-2-carbonitrile (46.0 mg, 0.295 mmol) was dissolved in THF (5.0 mL) followed by addition of NaH (14.2 mg. 60% in mineral oil). The mixture was stirred for 10 minutes before it was added to the flask containing the freshly prepared acid chloride dropwise at rt. The reaction was stirred at rt for 14 hours before silica gel was added to quench the reaction. Solvent was evaporated and the resulting residue was purified via silica gel column chromatography to yield 5-chloro-N-(3-chloro-5-cyanopyrazin-2-yl)-2-((4-methoxybenzy-poxy) benzamide (47.0 mg, 37% yield). $^{1}$H NMR (300 MHz, Chloroform-d) δ 10.96 (s, 1H), 8.69 (s, 1H), 8.29 (d, J=2.8 Hz, 1H), 7.57-7.50 (m, 1H), 7.42-7.37 (m, 2H), 7.16 (d, J=8.9 Hz, 1H), 6.98-6.92 (m, 2H), 5.27 (s, 2H), 3.86 (s, 3H).). MS (ESI) exact mass calculated for [M+H] (C20H15C12N4O3) requires m/z 429.0, found m/z 429.1.

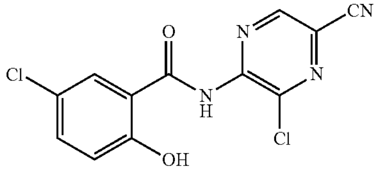 [SMILES: N#Cc1cnc(NC(=O)c2cc(Cl)ccc2O)c(Cl)n1]

5-Chloro-N-(3-chloro-5-cyanopyrazin-2-yl)-2-hydroxybenzamide (4)

5-chloro-N-(3-chloro-5-cyanopyrazin-2-yl)-2-((4-methoxybenzyl)oxy)benzamide (26.0 mg, 0.0606 mmol) was dissolved in DCM (5.0 mL) followed by addition of TFA (46 μL, 0.606 mmol) at rt. The mixture was stirred at rt for 4 hours before the solvent was evaporated. The residue was purified via silica gel column chromatography to yield 5-chloro-N-(3-chloro-5-cyanopyrazin-2-yl)-2-hydroxybenzamide 4 (6.7 mg, 36% yield) $^{1}$H NMR (500 MHz, Acetone-$d_6$) δ 8.93 (s, 1H), 8.08 (s, 1H), 7.46 (d, J=8.8 Hz, 1H), 7.19 (d, J=8.8 Hz, 1H). MS (ESI) exact mass calculated for [M+H] (C12H7C12N4O2) requires m/z 309.0, found m/z 309.0.

5

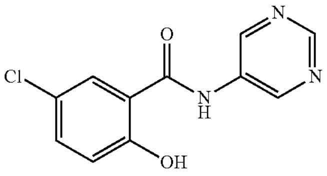

5-Chloro-2-hydroxy-N-(pyrimidin-5-yl)benzamide (5)

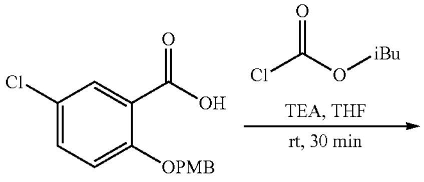

-continued

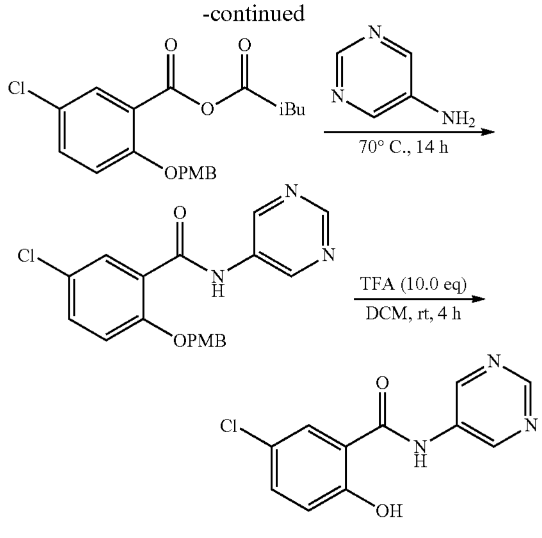

5-chloro-2-((4-methoxybenzyl)oxy)benzoic acid (103.0 mg, 0.352 mmol) was dissolved in THF (8.0 mL) followed by addition of TEA (59 μL, 0.422 mmol) and chloro isobutylformate (55 μL, 0.422 mmol) at P. The mixture was stirred at rt for 30 minutes before the addition of pyrimidin-5-amine (48.2 mg, 0.422 mmol). The reaction was heated to 70° C. and stirred for 14 hours. Silica gel was added to quench the reaction and the solvent was removed. The residue was purified via silica gel column chromatography to yield 5-chloro-2-((4-methoxybenzyl)oxy)-N-(pyrimidin-5-yl) benzamide (34.3 mg, 26% yield) which was then dissolved in DCM (5.0 mL) followed by addition of TFA (71 μL, 0.928 mmol). The reaction was stirred at rt for 4 hours before it was concentrated in vacuo. The residue was purified via silica gel column chromatography to yield 5-chloro-2-hydroxy-N-(pyrimidin-5-yl)benzamide 5 (3.0 mg, 13% yield). $^1$H NMR (300 MHz, DMSO-$d_6$) δ 10.79 (s, 1H), 9.14 (s, 2H), 8.96 (s, 1H), 7.89 (d, J=2.7 Hz, 1H), 7.54-7.45 (m, 1H), 7.04 (d, J=8.8 Hz, 1H). MS (ESI) exact mass calculated for [M+H] (C11H9ClN3O2) requires m/z 250.0, found m/z 250.0.

6

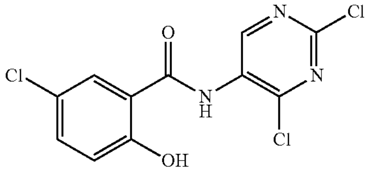

5-Chloro-N-(2,4-dichloropyrimidin-5-yl)-2-hydroxybenzamide (6)

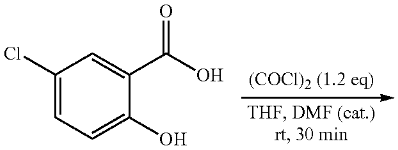

-continued

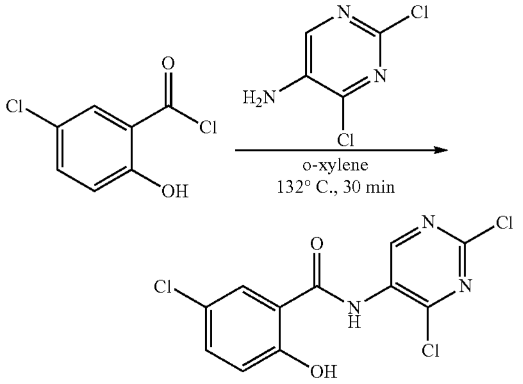

5-Chlorosalicyclic acid (211.4 mg, 1.225 mmol) was dissolved in THF (10.0 mL), followed by the addition of catalytic amount of DMF (10 μL) and oxalyl chloride (0.13 mL, 1.470 mmol) respectively. The reaction was allowed to stir at rt for 30 min and then concentrated in vacuo. The residue was re-dissolved in xylene (7.0 mL) followed by the addition of 2,4-dichloropyrimidin-5-amine (161.0 mg, 0.980 mmol). The mixture was heated to 132° C. and stirred for 30 minutes before it was brought back to P. The solvent was removed in vacuo and the resulting residue was purified via silica gel column chromatography to yield 5-Chloro-N-(2,4-dichloropyrimidin-5-yl)-2-hydroxybenzamide 6 ($^1$H NMR (300 MHz, DMSO-$d_6$) δ 12.45 (s, 1H), δ 11.04 (s, 1H), 9.60 (s, 1H), 7.95 (d, J=2.8 Hz, 1H), 7.55 (dd, J=8.8, 2.8 Hz, 1H), 7.11 (d, J=8.8 Hz, 1H). MS (ESI) exact mass calculated for [M+H] (C11H7C13N3O2) requires m/z 318.0, found m/z 317.9.

7

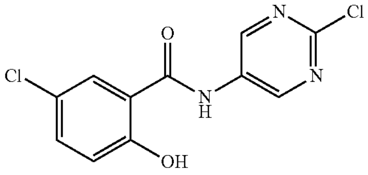

5-Chloro-N-(2-chloropyrimidin-5-yl)-2-hydroxybenzamide (7)

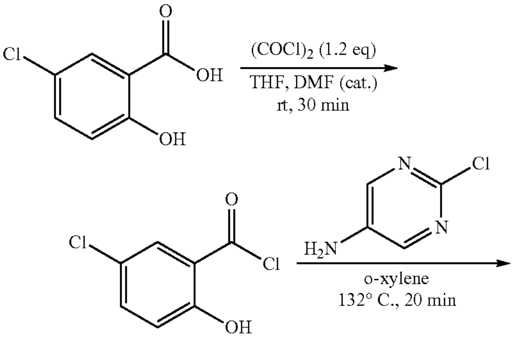

-continued

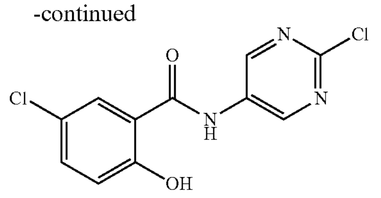

5-Chlorosalicyclic acid (253.4 mg, 1.468 mmol) was dissolved in THF (10.0 mL), followed by the addition of catalytic amount of DMF (10 μL) and oxalyl chloride (0.15 mL, 1.762 mmol) respectively. The reaction was allowed to stir at rt for 30 min and then concentrated in vacuo. The residue was re-dissolved in xylene (7.0 mL) followed by the addition of 4-chloropyrimidin-5-amine (152.0 mg, 1.174 mmol). The mixture was heated to 132° C. and stirred for 20 minutes before it was brought back to P. The solvent was removed in vacuo and the resulting residue was purified via silica gel column chromatography to yield 5-Chloro-N-(2-chloropyrimidin-5-yl)-2-hydroxybenzamide 7 (174.6 mg, 52% yield). $^1$H NMR (300 MHz, DMSO-$d_6$) δ 11.54 (s, 1H), 10.77 (s, 1H), 9.01 (s, 2H), 7.86 (d, J=2.7 Hz, 1H), 7.56-7.42 (m, 1H), 7.06 (d, J=8.8 Hz, 1H). MS (ESI) exact mass calculated for [M+H] (C11H8Cl2N3O2) requires m/z 284.0, found m/z 283.9.

8

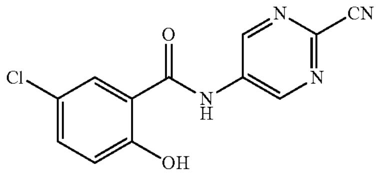

5-Chloro-N-(2-cyanopyrimidin-5-yl)-2-hydroxybenzamide (8)

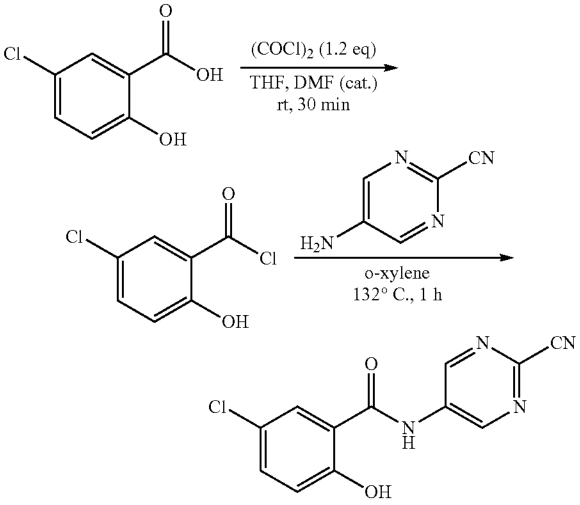

5-Chlorosalicyclic acid (144.0 mg, 0.833 mmol) was dissolved in THF (5.0 mL), followed by the addition of catalytic amount of DMF (10 μL) and oxalyl chloride (86 μL, 1.0 mmol) respectively. The reaction was allowed to stir at rt for 30 min and then concentrated in vacuo. The residue was re-dissolved in xylene (5.0 mL) followed by the addition of 4-chloropyrimidin-5-amine (80.0 mg, 0.666 mmol). The mixture was heated to 132° C. and stirred for 1 hour before it was brought back to P. The solvent was removed in vacuo and the resulting residue was purified via silica gel column chromatography to yield 5-Chloro-N-(2-cyanopyrimidin-5-yl)-2-hydroxybenzamide 8 (25.0 mg, 14% yield). $^1$H NMR (500 MHz, DMSO-$d_6$) δ 11.45 (s, 1H), 11.01 (s, 1H), 9.30 (s, 2H), 7.80 (d, J=2.7 Hz, 1H), 7.49 (dd, J=8.8, 2.6 Hz, 1H), 7.04 (d, J=8.8 Hz, 1H). MS (ESI) exact mass calculated for [M+H] (C12H8ClN4O2) requires m/z 275.0, found m/z 274.9.

9

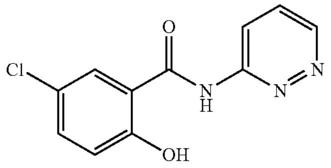

5-Chloro-2-hydroxy-N-(pyridazin-3-yl)benzamide (9)

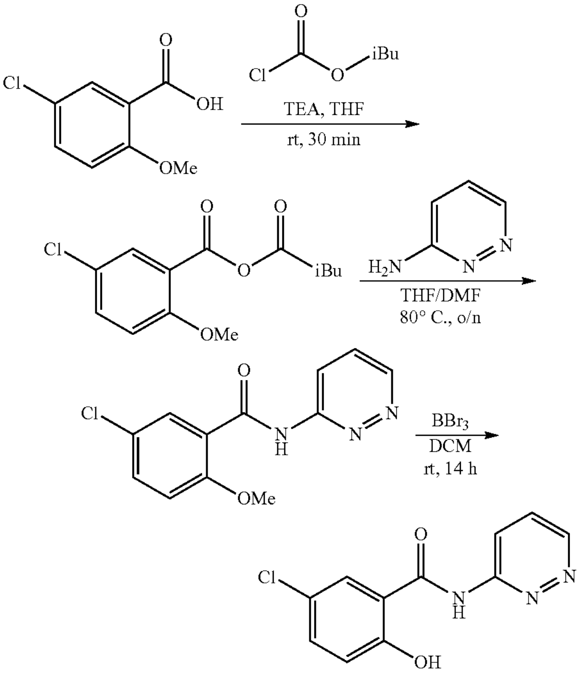

5-chloro-2-methoxybenzoic acid (196.2 mg, 1.052 mmol) was dissolved in THF (10.0 mL) followed by addition of TEA (0.18 mL, 1.262 mmol) and chloro isobutylformate (0.17 mL, 1.262 mmol) at rt. The mixture was stirred at rt for 30 minutes before the addition of pyridazin-3-amine (100.0 mg, 1.052 mmol). DMF (2.0 mL) was added, and the reaction was heated to 80° C. and stirred for 14 hours. Silica gel was added to quench the reaction and the solvent was removed. The residue was purified via silica gel column chromatography to yield 5-chloro-2-methoxy-N-(pyridazin-3-yl)benzamide (163.0 mg, 59% yield). 5-chloro-2-methoxy-N-(pyridazin-3-yl)benzamide (93.0 mg, 0.353 mmol) was dissolved in DCM followed by addition of boron tribromide (1.8 mL, 1.0 M in DCM) at P. The reaction was stirred at rt for 14 hours before it was quenched with aq. Sodium bicarbonate. The mixture was extracted with ethyl acetate and the organic layer was separated. The solvents were concentrated and the residue was purified via silica gel column chromatography to yield 5-Chloro-2-hydroxy-N-(pyridazin-3-yl)benzamide 9 (15.3 mg, 17% yield). $^1$H NMR (300 MHz, DMSO-$d_6$) δ 12.19 (s, 1H), 11.39 (s, 1H), 9.03 (dd, J=4.7, 1.5 Hz, 1H), 8.48 (dd, J=9.0, 1.5 Hz, 1H), 7.97 (dd, J=2.9, 1.0 Hz, 1H), 7.86-7.67 (m, 1H), 7.53 (dd, J=8.8, 2.8 Hz, 1H), 7.11 (d, J=8.8 Hz, 1H). MS (ESI) exact mass calculated for [M+H] (C11H9ClN3O2) requires m/z 250.0, found m/z 249.9.

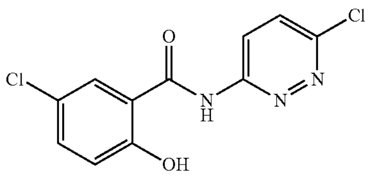 [SMILES: O=C(Nc1ccc(Cl)nn1)c1cc(Cl)ccc1O]

5-Chloro-N-(6-chloropyridazin-3-yl)-2-hydroxybenzamide (10)

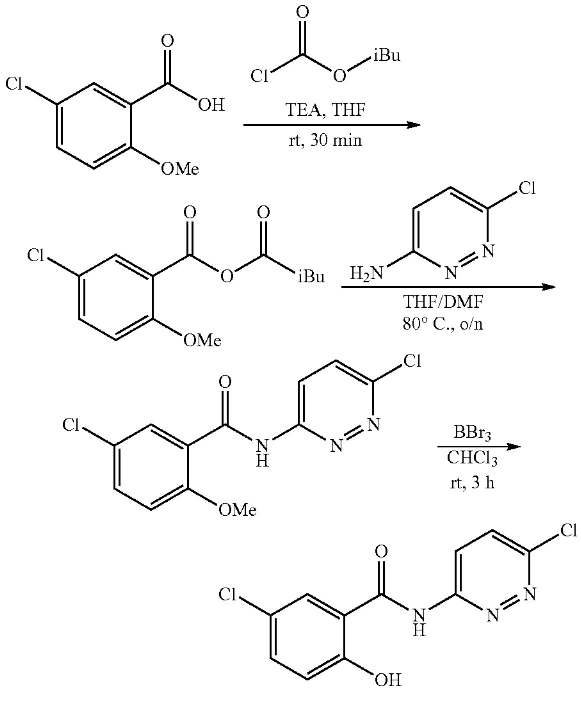

5-chloro-2-methoxybenzoic acid (179.7 mg, 0.963 mmol) was dissolved in THF (10.0 mL) followed by addition of TEA (0.16 mL, 1.156 mmol) and chloro isobutylformate (0.15 mL, 1.156 mmol) at rt. The mixture was stirred at rt for 30 minutes before the addition of 6-chloropyridazin-3-amine (125.0 mg, 0.963 mmol). DMF (2.0 mL) was added, and the reaction was heated to 80° C. and stirred for 14 hours. Silica gel was added to quench the reaction and the solvent was removed. The residue was purified via silica gel column chromatography to yield 5-chloro-N-(6-chloropyridazin-3-yl)-2-methoxybenzamide (101.5 mg, 35% yield). 5-chloro-N-(6-chloropyridazin-3-yl)-2-methoxybenzamide (25.8 mg, 0.0865 mmol) was dissolved in DCM followed by addition of boron tribromide (0.45 mL, 1.0 M in DCM) at P. The reaction was stirred at rt for 3 hours before it was quenched with aq. Sodium bicarbonate. The mixture was extracted with ethyl acetate and the organic layer was separated. The solvents were concentrated and the residue was purified via silica gel column chromatography to yield 5-Chloro-N-(6-chloropyridazin-3-yl)-2-hydroxybenzamide 10 (18.4 mg, 75% yield). $^1$H NMR (400 MHz, DMSO-$d_6$) δ 12.08 (s, 1H), 11.40 (s, 1H), 8.52 (d, J=9.3 Hz, 1H), 7.99-7.86 (m, 2H), 7.51 (dd, J=8.4, 2.3 Hz, 1H), 7.08 (d, J=8.7 Hz, 1H). MS (ESI) exact mass calculated for [M+H] (C11H8Cl2N3O2) requires m/z 284.0, found m/z 283.9.

11

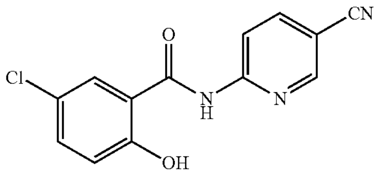

5-Chloro-N-(5-cyanopyridin-2-yl)-2-hydroxybenzamide (11)

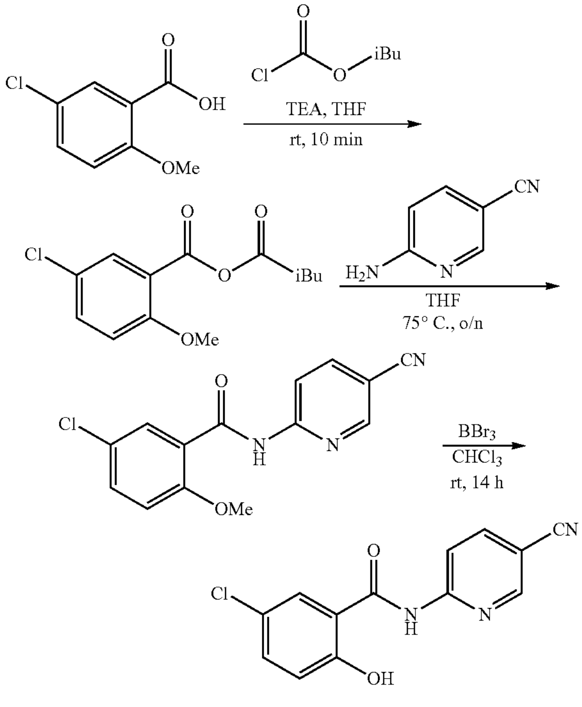

This compound is known and the preparation herein was adapted from the literature procedure. (Bioorganic and Medicinal Chemistry Letters, 2013, 23(6), 1748-1751).

5-chloro-2-methoxybenzoic acid (324.4 mg, 1.739 mmol) was dissolved in THF (10.0 mL) followed by addition of TEA (0.29 mL, 2.086 mmol) and chloro isobutylformate (0.27 mL, 2.086 mmol) at rt. The mixture was stirred at rt for 10 minutes before the addition of 6-aminonicotinonitrile (207.0 mg, 1.739 mmol). The reaction was heated to 75° C. and stirred for 14 hours. Silica gel was added to quench the reaction and the solvent was removed. The residue was purified via silica gel column chromatography to yield 5-chloro-N-(5-cyanopyridin-2-yl)-2-methoxybenzamide (147.0 mg, 29% yield). 5-chloro-N-(5-cyanopyridin-2-yl)-2-methoxybenzamide (147.0 mg, 0.511 mmol) was dissolved in DCM followed by addition of boron tribromide (2.6 mL, 1.0 M in DCM) at P. The reaction was stirred at rt for 14 hours before it was quenched with aq. Sodium bicarbonate. The mixture was extracted with ethyl acetate and the organic layer was separated. The solvents were concentrated and the residue was purified via silica gel column chromatography to yield 5-Chloro-N-(5-cyanopyridin-2-yl)-2-hydroxybenzamide 11 (3.0 mg, 2% yield). $^1H$ NMR(DMSO-d6) δ 12.09 (brs, 1H), 11.21 (s, 1H), 8.83 (d, J=2.1 Hz, 1H), 8.32-8.41 (m, 2H), 7.92 (d, J=2.8 Hz, 1H), 7.52 (dd, J1=8.8 Hz, J2=2.8 Hz, 1H), 7.09 (d, J=8.8 Hz, 1H).

12

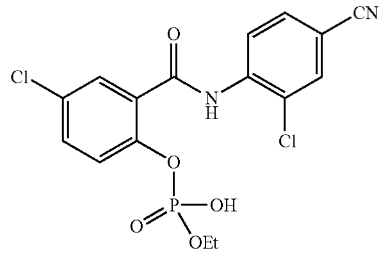

4-Chloro-2-((2-chloro-4-cyanophenyl)carbamoyl)phenyl ethyl hydrogen phosphate (12)

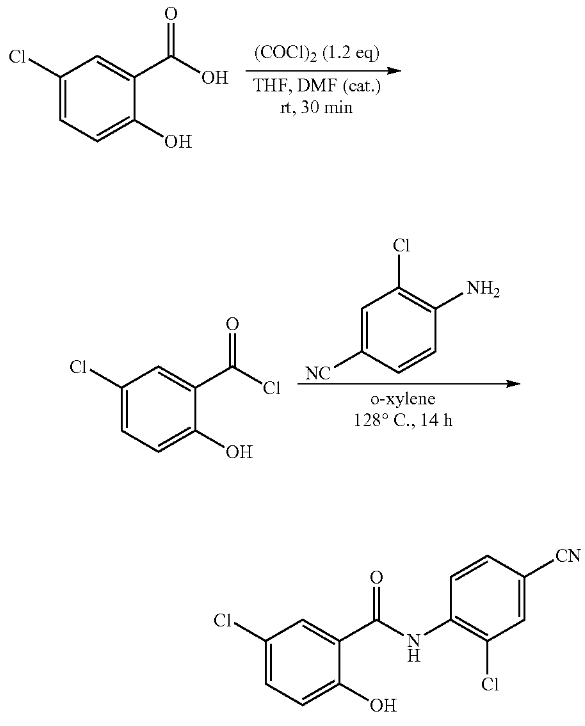

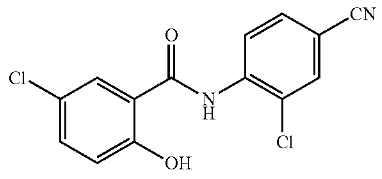 [SMILES: N#Cc1ccc(NC(=O)c2cc(Cl)ccc2O)c(Cl)c1]

5-Chloro-N-(2-chloro-4-cyanophenyl)-2-hydroxybenzamide

The starting material 5-chlorosalicyclic acid (561.0 mg, 3.251 mmol) was dissolved in THF (8.0 mL), followed by the addition of catalytic amount of DMF (10 μL) and oxalyl chloride (0.33 mL, 3.901 mmol) respectively. The reaction was allowed to stir at rt for 30 min and then concentrated in vacuo. The residue was re-dissolved in o-xylene followed by addition of the cyano aniline. The mixture was then heated to 128° C. and stirred at this temperature for 14 hours before it was cooled to rt and filtered. The filter cake was washed with cold diethyl ether to give the crude cyano amide which was further purified through silica gel column chromatography (25% acetone/hexances) to yield 5-chloro-N-(2-chloro-4-cyanophenyl)-2-hydroxybenzamide as an off-white solid (519.0 mg, 52% yield). $^1H$ NMR (500 MHz, Acetone-$d_6$) δ 8.44 (d, J=9.2 Hz, 1H), 8.29 (d, J=2.6 Hz, 1H), 8.22 (dd, J=9.2, 2.6 Hz, 1H), 7.92 (d, J=2.2 Hz, 1H), 7.62 (dd, J=8.2, 2.2 Hz, 1H), 7.43 (d, J=8.2 Hz, 1H). MS (ESI) exact mass calculated for [M+H] (C14H8Cl2N2O2) requires m/z 306.0, found m/z 306.9.

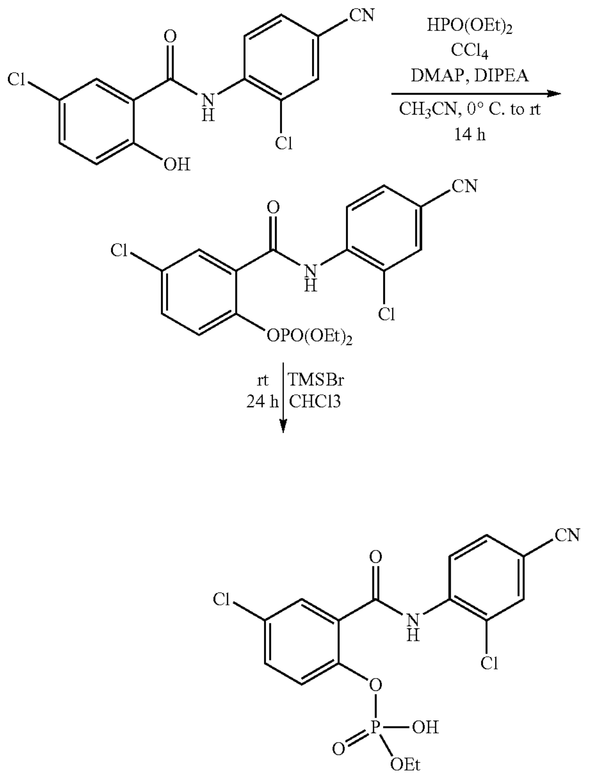

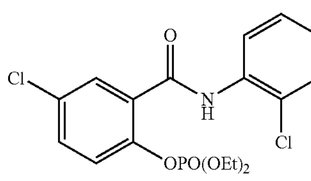

4-Chloro-2-((2-chloro-4-cyanophenyl)carbamoyl) phenyl diethyl phosphate

The starting 5-chloro-N-(2-chloro-4-cyanophenyl)-2-hydroxybenzamide (225.1 mg, 0.733 mmol) was dissolved in acetonitrile (15.0 mL) and cooled to 0° C., followed by addition of diethyl phosphite (113 μL, 0.880 mmol), $CCl_4$ (0.51 mL), DMAP (11.0 mg) and Hunig's base (0.30 mL). The mixture was allowed to gradually warm up to rt and stirred at rt for 14 h before it was concentrated in vacuo. The residue was purified via silica gel column chromatography (30% acetone/hexanes) to yield the 4-chloro-2-((2-chloro-4-cyanophenyl)carbamoyl)phenyl diethyl phosphate as a white solid (227.8 mg, 70% yield). $^1$H NMR (300 MHz, Chloroform-d) δ 9.45 (s, 1H), 8.77 (d, J=8.7 Hz, 1H), 8.06 (ddt, J=2.5, 1.2, 0.6 Hz, 1H), 7.74 (dd, J=2.0, 0.5 Hz, 1H), 7.64 (ddt, J=8.7, 2.0, 0.6 Hz, 1H), 7.56-7.51 (m, 2H), 4.34-4.12 (m, 4H), 1.32 (tdd, J=7.1, 1.2, 0.5 Hz, 6H).

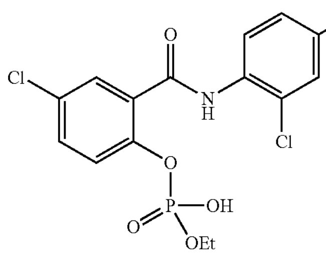

4-Chloro-2-((2-chloro-4-cyanophenyl)carbamoyl) phenyl ethyl hydrogen phosphate (12)

4-Chloro-2-((2-chloro-4-cyanophenyl)carbamoyl)phenyl diethyl phosphate (187.0 mg, 0.422 mmol) was dissolved in chloroform (10.0 mL) followed by dropwise addition of bromo trimethylsilane (0.28 mL, 2.110 mmol) at P. The reaction was stirred at rt for 24 h before it was concentrated in vacuo. The residue was re-dissolved in methanol, stirred for 30 min and the solvent was evaporated. A solution of 5% water/acetonitrile was added to the residue and the mixture was filtered. The filter cake was washed with ether to give 4-chloro-2-((2-chloro-4-cyanophenyl)carbamoyl)phenyl ethyl hydrogen phosphate 12 as a white solid (50.0 mg, 29% yield). $^1$H NMR (500 MHz, DMSO-$d_6$) δ 11.49 (d, J=4.1 Hz, 1H), 8.32-8.22 (m, 1H), 8.10 (dt, J=4.4, 1.9 Hz, 1H), 7.83 (dt, J=8.6, 2.2 Hz, 1H), 7.76 (t, J=2.8 Hz, 1H), 7.60 (d, J=8.8 Hz, 1H), 7.54 (dt, J=10.5, 3.5 Hz, 1H), 3.76 (p, J=7.3 Hz, 2H), 1.09-0.94 (m, 3H). MS (ESI) exact mass calculated for [M+H] (C16H13C12N2O5P) requires m/z 414.0, found m/z 414.8.

13

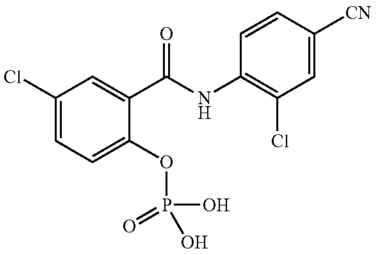 [SMILES: CCOP(=O)(O)Oc1ccc(Cl)cc1C(=O)Nc1ccc(C#N)cc1Cl]

4-Chloro-2-((2-chloro-4-cyanophenyl)carbamoyl) phenyl dihydrogen phosphate (13)

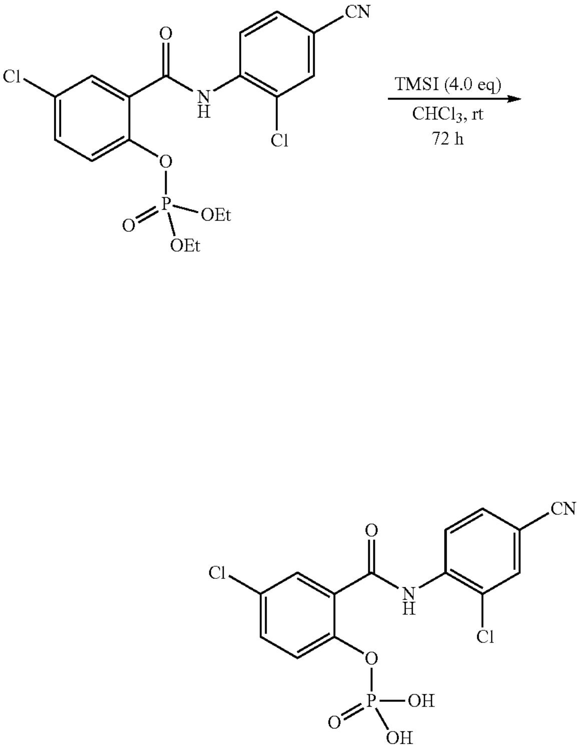

The starting 4-chloro-2-((2-chloro-4-cyanophenyl)carbamoyl)phenyl diethyl phosphate (227.8 mg, 0.514 mmol) was dissolved in chloroform (10.0 mL) followed by dropwise addition of iodo trimethylsilane (0.29 mL, 2.056 mmol) at rt. The reaction was stirred at rt for 72 h before it was concentrated in vacuo. The residue was re-dissolved in methanol, stirred for 30 min and the solvent was evaporated. A solution of 5% water/acetonitrile was added to the residue and the mixture was filtered. The filter cake was washed with ether to give 4-chloro-2-((2-chloro-4-cyanophenyl)carbamoyl)phenyl dihydrogen phosphate 13 as an off-white solid (120.0 mg, 60% yield). $^1$H NMR (500 MHz, DMSO-$d_6$) δ 10.24 (s, 1H), 8.34 (d, J=8.5 Hz, 1H), 8.12 (d, J=1.9 Hz, 1H), 7.86 (dd, J=8.6, 1.9 Hz, 1H), 7.79 (d, J=2.6 Hz, 1H), 7.64 (dd, J=8.8, 2.8 Hz, 1H), 7.51 (d, J=8.7 Hz, 1H). MS (ESI) exact mass calculated for [M+H] (C14H9C12N2O5P) requires m/z 386.0, found m/z 386.8.

14

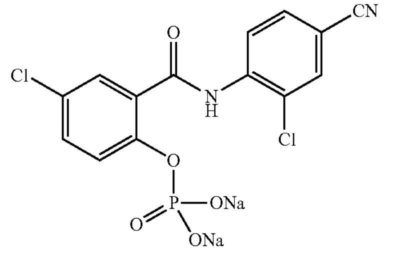

Sodium 4-chloro-2-((2-chloro-4-cyanophenyl)carbamoyl)phenyl phosphate (14)

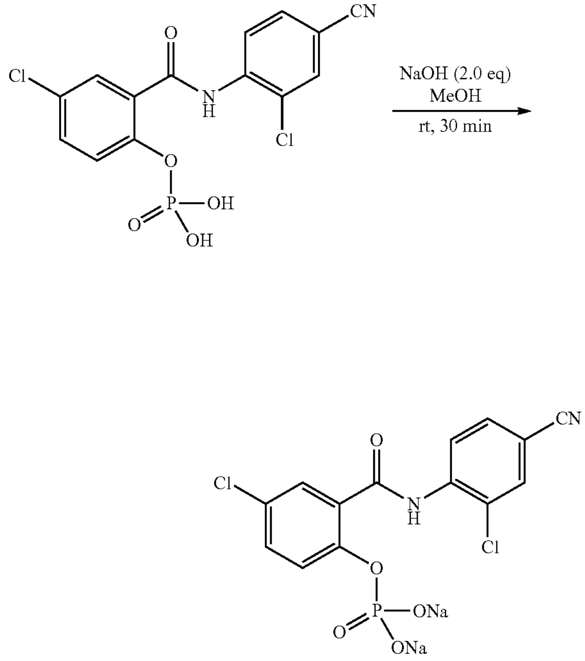

The starting 4-chloro-2-((2-chloro-4-cyanophenyl)carbamoyl)phenyl dihydrogen phosphate (102.3 mg, 0.264 mmol) was dissolved in methanol (2.0 mL) followed by addition of a solution of NaOH (21.1 mg, 0.528 mmol) in methanol (1.2 mL). The mixture was stirred at rt for 30 min and the solvent was removed to yield the title compound 14 as a white solid (120.0 mg, quantitative). $^{1}$H NMR (300 MHz, Deuterium Oxide) δ 7.94 (d, J=8.5 Hz, 1H), 7.89-7.73 (m, 2H), 7.65 (d, J=8.8 Hz, 1H), 7.56-7.39 (m, 2H).

15

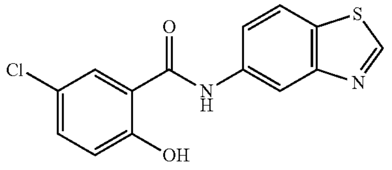

N-(Benzo[d]thiazol-5-yl)-5-chloro-2-hydroxybenzamide (15)

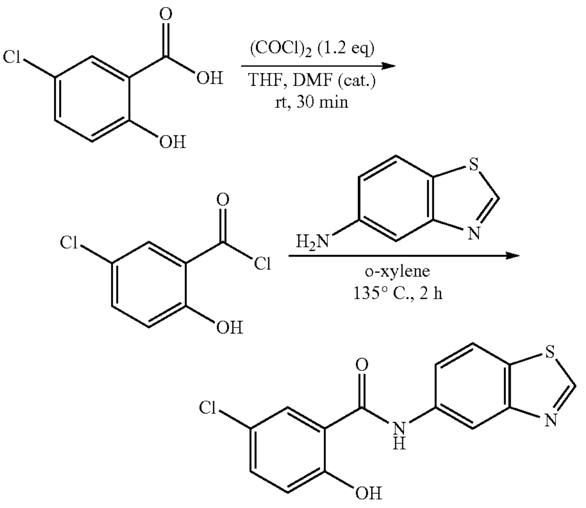

5-Chlorosalicyclic acid (215.7 mg, 1.250 mmol) was dissolved in THF (8.0 mL), followed by the addition of catalytic amount of DMF (10 μL) and oxalyl chloride (0.13 mL, 1.500 mmol) respectively. The reaction was allowed to stir at rt for 30 min and then concentrated in vacuo. The residue was re-dissolved in o-xylene followed by addition of benzo[d]thiazol-5-amine (150.2 mg, 1.000 mmol). The mixture was then heated to 135° C. and stirred at this temperature for 2 hours before it was cooled to rt and filtered. The filter cake was washed with cold diethyl ether to give N-(benzo[d]thiazol-5-yl)-5-chloro-2-hydroxybenzamide 15 as an off-white solid (40.6 mg, 13% yield). $^{1}$H NMR (300 MHz, DMSO-$d_6$) δ 11.10 (brs, 1H), δ 9.41 (d, J=0.8 Hz, 1H), 8.59 (d, J=2.0 Hz, 1H), 8.14 (dd, J=8.7, 0.9 Hz, 1H), 7.95 (dd, J=2.7, 0.9 Hz, 1H), 7.73 (dd, J=8.7, 2.1 Hz, 1H), 7.44 (ddd, J=8.9, 2.7, 0.9 Hz, 1H), 7.00 (dd, J=8.7, 0.9 Hz, 1H). MS (ESI) exact mass calculated for [M+H] (C14H10ClN2O2S) requires m/z 305.0, found m/z 305.1.

16

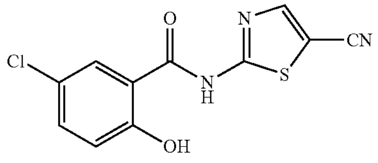

5-chloro-N-(5-cyanothiazol-2-yl)-2-hydroxybenzamide (16)

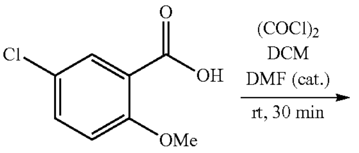

-continued

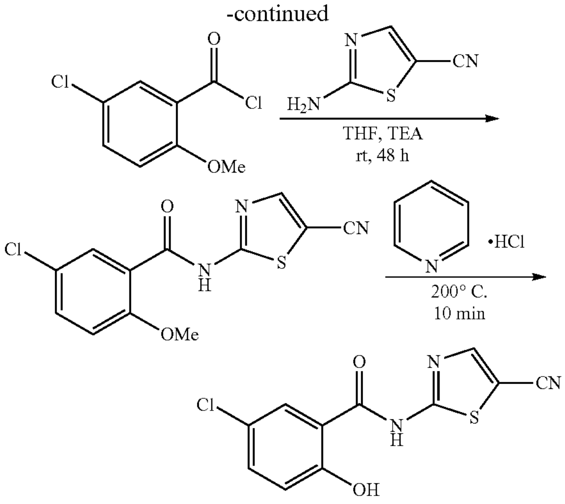

5-chloro-2-methoxybenzoic acid (186.7 mg, 1.000 mmol) was dissolved in DCM (10.0 mL), followed by the addition of catalytic amount of DMF (20 μL) and oxalyl chloride (0.10 mL, 1.200 mmol) respectively. The reaction was allowed to stir at rt for 30 min, concentrated in vacuo, and the residue was re-dissolved in DCM (10.0 mL). In another flask, 2-aminothiazole-5-carbonitrile (100.0 mg, 0.800 mmol) was dissolved in THF (5.0 mL) followed by addition of triethylamine (0.17 mL, 1.200 mmol). The reaction was stirred at rt for 48 h before silica gel was added to quench the reaction. Solvent was evaporated and the resulting residue was purified via silica gel column chromatography to give 5-chloro-N-(5-cyanothiazol-2-yl)-2-methoxybenzamide which was mixed with pyridinium chloride (550.0 mg). The mixture was heated to 200° C., stirred for 10 minutes and cooled down to rt. The resulting solid was suspended in water and filtered. The filter cake was washed with diethyl ether to yield 5-chloro-N-(5-cyanothiazol-2-yl)-2-hydroxybenzamide 16 (40.3 mg, 18% yield over 2 steps). $^1$H NMR (300 MHz, DMSO-$d_6$) δ 8.45 (d, J=1.2 Hz, 1H), 7.85 (dd, J=2.8, 1.2 Hz, 1H), 7.52 (ddd, J=8.8, 2.8, 1.2 Hz, 1H), 7.06 (dd, J=8.9, 1.2 Hz, 1H). MS (ESI) exact mass calculated for [M+H] (C11H7ClN3O2S) requires m/z 280.0, found m/z 279.9.

17

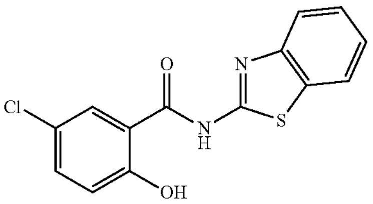

N-(Benzo[d]thiazol-2-yl)-5-chloro-2-hydroxybenzamide (17)

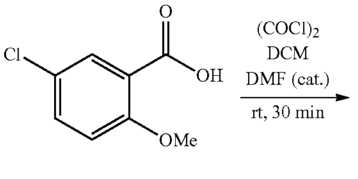

-continued

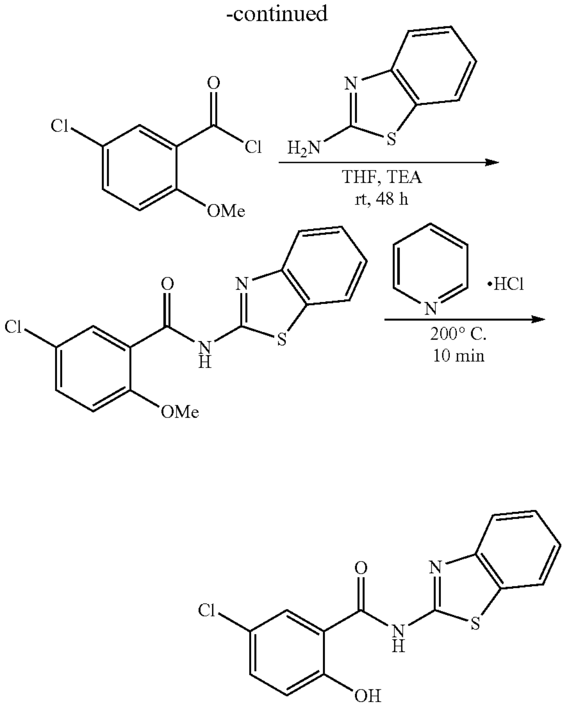

5-chloro-2-methoxybenzoic acid (186.7 mg, 1.000 mmol) was dissolved in DCM (10.0 mL), followed by the addition of catalytic amount of DMF (20 μL) and oxalyl chloride (0.10 mL, 1.200 mmol) respectively. The reaction was allowed to stir at rt for 30 min, concentrated in vacuo, and the residue was then dissolved in THF (10.0 mL). To this flask, was added triethylamine (0.17 mL, 1.200 mmol) followed by benzo[d]thiazol-2-amine (120.2 mg, 0.800 mmol). The reaction was stirred at rt for 48 h before silica gel was added to quench the reaction. Solvent was evaporated and the resulting residue was purified via silica gel column chromatography to give N-(benzo[d]thiazol-2-yl)-5-chloro-2-methoxybenzamide (165.8 mg, 65% yield). This amide (50.0 mg, 0.157 mmol) was mixed with pyridinium chloride (1.0 g). The mixture was heated to 200° C., stirred for 10 minutes and cooled down to P. The resulting solid was suspended in water and filtered. The filter cake was washed with water, diethyl ether and dichloromethane to yield N-(benzo[d]thiazol-2-yl)-5-chloro-2-hydroxybenzamide 17 (25.0 mg, 52% yield). $^1$H NMR (300 MHz, DMSO-$d_6$) δ 8.03 (d, J=7.9 Hz, 1H), 7.95 (d, J=2.7 Hz, 1H), 7.73 (s, 1H), 7.51 (t, J=7.6 Hz, 2H), 7.44-7.33 (m, 1H), 7.07 (d, J=8.7 Hz, 1H). MS (ESI) exact mass calculated for [M+H] (C14H10ClN2O2S) requires m/z 305.0, found m/z 304.9.

18

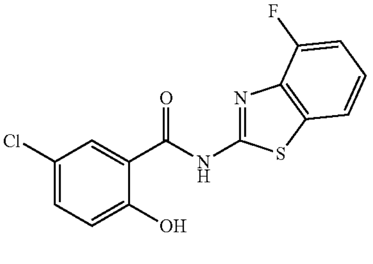

5-Chloro-N-(4-fluorobenzo[d]thiazol-2-yl)-2-hydroxybenzamide (18)

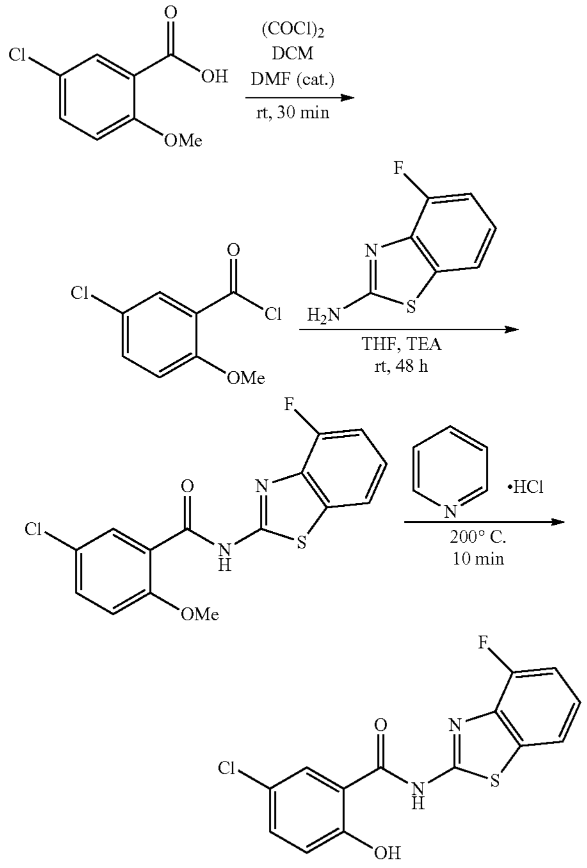

5-chloro-2-methoxybenzoic acid (186.7 mg, 1.000 mmol) was dissolved in DCM (10.0 mL), followed by the addition of catalytic amount of DMF (20 μL) and oxalyl chloride (0.10 mL, 1.200 mmol) respectively. The reaction was allowed to stir at rt for 30 min, concentrated in vacuo, and the residue was then dissolved in THF (10.0 mL). To this flask, was added triethylamine (0.17 mL, 1.200 mmol) followed by 4-fluorobenzo[d]thiazol-2-amine (134.6 mg, 0.800 mmol). The reaction was stirred at rt for 48 h before silica gel was added to quench the reaction. Solvent was evaporated and the resulting residue was purified via silica gel column chromatography to give 5-chloro-N-(4-fluorobenzo[d]thiazol-2-yl)-2-methoxybenzamide (101.1 mg, 38% yield). This amide (50.0 mg, 0.148 mmol) was mixed with pyridinium chloride (1.0 g). The mixture was heated to 200° C., stirred for 10 minutes and cooled down to rt. The resulting solid was suspended in water and filtered. The filter cake was washed with water, acetone and diethyl ether to yield 5-chloro-N-(4-fluorobenzo[d]thiazol-2-yl)-2-hydroxybenzamide 18 (15.0 mg, 31% yield). $^1$H NMR (300 MHz, DMSO-$d_6$) δ 7.99-7.92 (m, 1H), 7.92-7.83 (m, 1H), 7.60-7.50 (m, 1H), 7.35 (h, J=8.1, 7.5 Hz, 2H), 7.11 (d, J=8.5 Hz, 1H). MS (ESI) exact mass calculated for [M+H] (C14H19ClFN2O2S) requires m/z 323.0, found m/z 322.9.

19

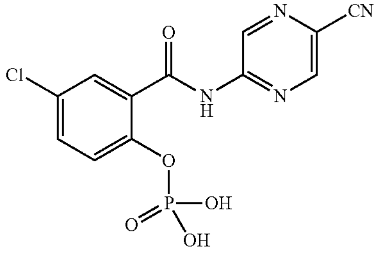

4-Chloro-2-((5-cyanopyrazin-2-yl)carbamoyl)phenyl dihydrogen phosphate (19)

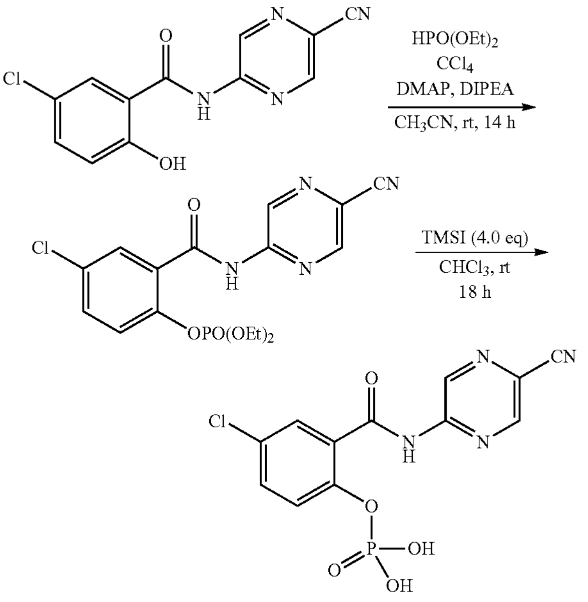

5-chloro-N-(5-cyanopyrazin-2-yl)-2-hydroxybenzamide (200.0 mg, 0.728 mmol) was dissolved in acetonitrile (10.0 mL) and cooled to 0° C., followed by addition of diethyl phosphite (110 μL, 0.874 mmol), $CCl_4$ (0.51 mL), DMAP (11.0 mg) and Hunig's base (0.30 mL). The mixture was allowed to gradually warm up to rt and stirred at rt for 14 h before it was concentrated in vacuo. The residue was purified via silica gel column chromatography (30% acetone/hexanes) to yield the desired product 4-chloro-2-((5-cyanopyrazin-2-yl)carbamoyl)phenyl diethyl phosphate as a colorless oil (121.0 mg, 41% yield). 4-chloro-2-((5-cyanopyrazin-2-yl)carbamoyl)phenyl diethyl phosphate (121.0 mg, 0.295 mmol) was dissolved in chloroform (10.0 mL) followed by dropwise addition of iodo trimethylsilane (0.17 mL, 1.178 mmol) at rt. The reaction was stirred at rt for 2 h before it was concentrated in vacuo. The residue was re-dissolved in methanol, stirred for 30 min and the solvent was evaporated. Diethyl ether was added to the residue and the mixture was filtered. The filter cake was washed with ether to give 4-chloro-2-((5-cyanopyrazin-2-yl)carbamoyl)phenyl dihydrogen phosphate 19 as an off-white solid (61.2 mg, 58% yield). $^1$H NMR (300 MHz, DMSO-$d_6$) δ 11.71 (s, 1H), 9.51 (t, J=1.5 Hz, 1H), 9.02 (t, J=1.5 Hz, 1H), 7.70 (d, J=2.8 Hz, 1H), 7.64 (ddd, J=8.8, 3.8, 2.0 Hz, 1H), 7.42 (dt, J=8.9, 1.5 Hz, 1H). MS (ESI) exact mass calculated for [M+H] (C12H9ClN4O5P) requires m/z 355.0, found m/z 355.0.

20

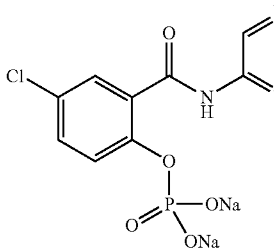

Sodium 4-chloro-2-((5-cyanopyrazin-2-yl)carbamoyl)phenyl phosphate phosphate (20)

4-chloro-2-((5-cyanopyrazin-2-yl)carbamoyl)phenyl dihydrogen phosphate 19 (540.8 mg, 1.525 mmol) was dissolved in methanol (10.0 mL) followed by addition of a solution of NaOH (122.0 mg, 3.050 mmol) in methanol (7.0 mL). The mixture was stirred at rt for 20 min and the solvent was removed to yield the title compound sodium 4-chloro-2-((5-cyanopyrazin-2-yl)carbamoyl)phenyl phosphate 20 (607.9 mg, quantitative). $^1H$ NMR (300 MHz, DMSO-$d_6$) δ 9.62 (d, J=1.4 Hz, 1H), 8.81 (d, J=1.4 Hz, 1H), 7.64 (d, J=3.0 Hz, 1H), 7.07-7.00 (m, 1H), 6.49 (d, J=9.0 Hz, 1H).

21

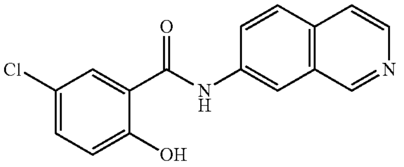

5-Chloro-2-hydroxy-N-(isoquinolin-7-yl)benzamide (21)

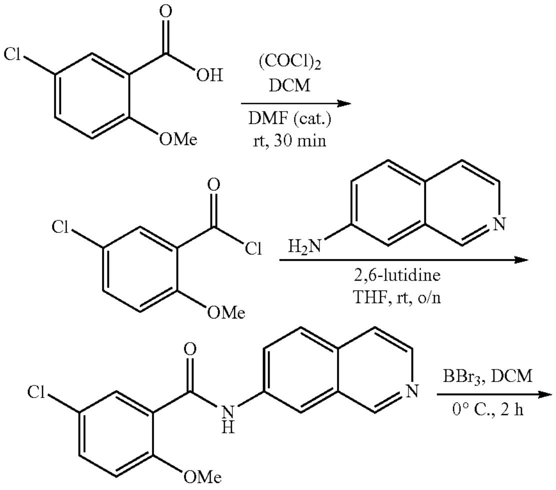

-continued

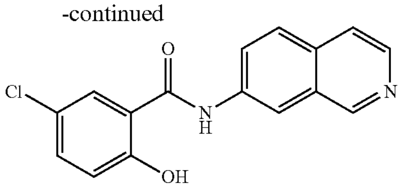

5-Chloro-2-methoxybenzoic acid (162.0 mg, 0.868 mmol) was dissolved in DCM (5.0 mL), followed by the addition of catalytic amount of DMF (10 μL) and oxalyl chloride (0.09 mL, 1.042 mmol) respectively. The reaction was allowed to stir at rt for 30 min, and concentrated in vacuo. The residue was re-dissolved in THF (5.0 mL), 2,6-lutidine (0.1 mL, 0.868 mmol) and isoquinolin-7-amine (100.0 mg, 0.694 mmol) were added. The mixture was stirred at rt for 18 hours before silica gel was added to quench the reaction. Solvent was evaporated and the resulting residue was purified via silica gel column chromatography to give 5-chloro-N-(isoquinolin-7-yl)-2-methoxybenzamide (53.0 mg, 24% yield). 5-Chloro-N-(isoquinolin-7-yl)-2-methoxybenzamide (29.8 mg, 0.0953 mmol) was dissolved in DCM followed by the addition of boron tribromide (0.29 mL, 1.0 M in DCM) at 0° C. The reaction was stirred at rt for 14 hours before it was quenched with aq. sodium bicarbonate. The mixture was extracted with DCM and the organic layer was separated. The solvents were concentrated and the residue was purified via silica gel column chromatography to yield 5-chloro-2-hydroxy-N-(isoquinolin-7-yl)benzamide 21 (21.3 mg, 75% yield). $^1H$ NMR (300 MHz, Acetone-d6) δ 9.41 (s, 1H), 8.76 (s, 1H), 8.55-8.48 (m, 1H), 8.22 (dt, J=5.5, 2.6 Hz, 2H), 8.09 (d, J=8.9 Hz, 1H), 7.93 (d, J=5.9 Hz, 1H), 7.53 (dd, J=8.9, 2.6 Hz, 1H), 7.15 (d, J=8.9 Hz, 1H). MS (ESI) exact mass calculated for [M+H] (C16H11ClN2O2) requires m/z 299.1, found m/z 298.9.

22

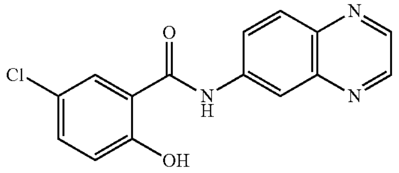

5-Chloro-2-hydroxy-N-(quinoxalin-6-yl)benzamide (22)

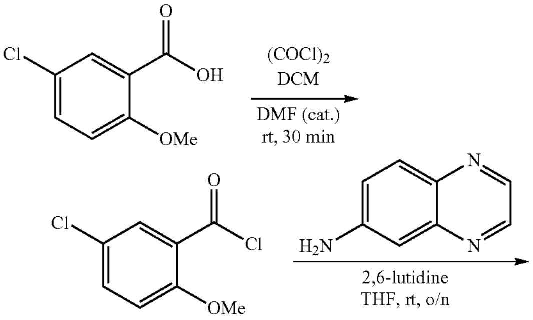

-continued

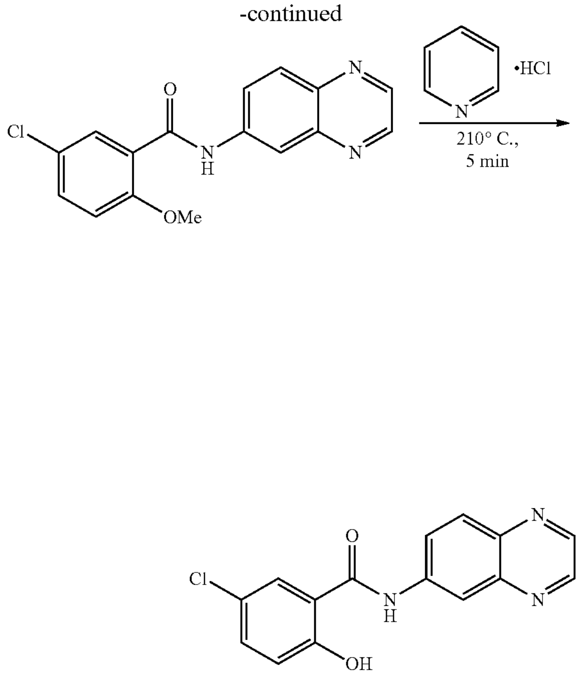

5-Chloro-2-methoxybenzoic acid (162.0 mg, 0.868 mmol) was dissolved in DCM (5.0 mL), followed by the addition of catalytic amount of DMF (10 μL) and oxalyl chloride (0.09 mL, 1.042 mmol) respectively. The reaction was allowed to stir at rt for 30 min, concentrated in vacuo. The residue was re-dissolved in THF (5.0 mL), 2,6-lutidine (0.1 mL, 0.868 mmol) and quinoxalin-6-amine (100.0 mg, 0.689 mmol) were added. The mixture was stirred at rt for 18 hours before silica gel was added to quench the reaction. Solvent was evaporated and the resulting residue was purified via silica gel column chromatography to give 5-chloro-2-methoxy-N-(quinoxalin-6-yl)benzamide (85.0 mg, 39% yield). This compound (35.5 mg, 0.113 mmol) was then mixed with pyridinium chloride (360.0 mg). The mixture was heated to 200° C., stirred for 5 minutes and cooled down to rt. The resulting solid was suspended in water and extracted with EtOAc. The organic phase was separated and evaporated. The resulting residue was purified via preparative TLC to yield 5-chloro-2-hydroxy-N-(quinoxalin-6-yl) benzamide 22 (10.6 mg, 31% yield). $^1$H NMR (300 MHz, Acetone-$d_6$) δ 8.89 (dd, J=14.9, 1.8 Hz, 2H), 8.72 (d, J=2.4 Hz, 1H), 8.26-8.07 (m, 3H), 7.10 (d, J=8.8 Hz, 1H). MS (ESI) exact mass calculated for [M+H] (C15H11ClN3O2) requires m/z 300.1, found m/z 299.8

23

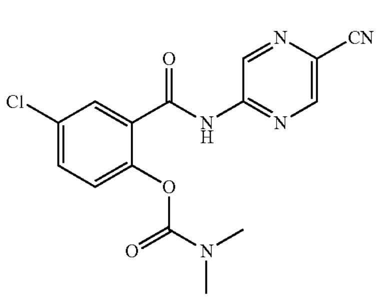

4-Chloro-2-((5-cyanopyrazin-2-yl)carbamoyl)phenyl dimethylcarbamate (23)

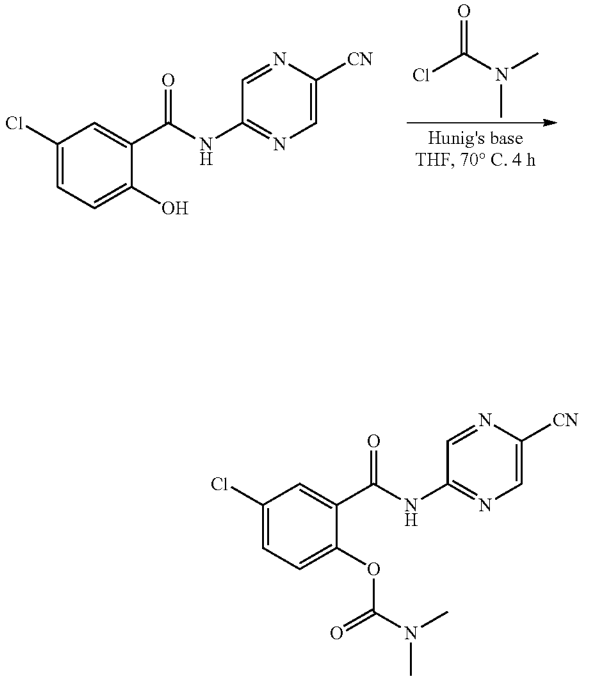

To an empty flask was added 5-chloro-N-(5-cyanopyrazin-2-yl)-2-hydroxybenzamide (109.7 mg, 0.399 mmol), followed by the addition of THF (5.0 mL) and Hunig's base (0.14 mL, 0.798 mmol). To this solution was added dimethylcarbamic chloride (44 μL, 0.479 mmol). The reaction was stirred at 70° C. for 4 hours before silica gel was added. Solvent was then removed and the residue was purified via silica gel column chromatography to yield 4-chloro-2-((5-cyano-pyrazin-2-yl)carbamoyl)phenyl dimethylcarbamate 23 (94 mg, 80% yield). $^1$H NMR (500 MHz, Chloroform-d) δ 9.75 (d, J=1.5 Hz, 1H), 9.59 (s, 1H), 8.58 (d, J=1.5 Hz, 1H), 7.93 (d, J=2.6 Hz, 1H), 7.52 (dd, J=8.8, 2.6 Hz, 1H), 7.17 (d, J=8.7 Hz, 1H), 3.20 (s, 3H), 3.03 (s, 3H). MS (ESI) exact mass calculated for [M+H] (C15H13ClN5O3) requires m/z 346.1, found m/z 345.9.

24

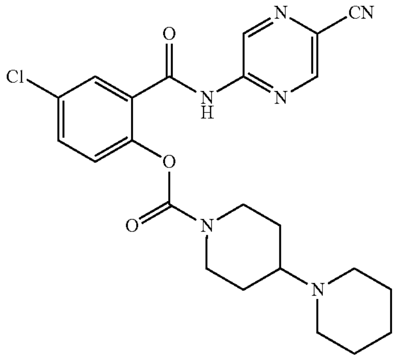

4-chloro-2-((5-cyanopyrazin-2-yl)carbamoyl)phenyl [1,4'-bipiperidine]-1-carboxylate (24)

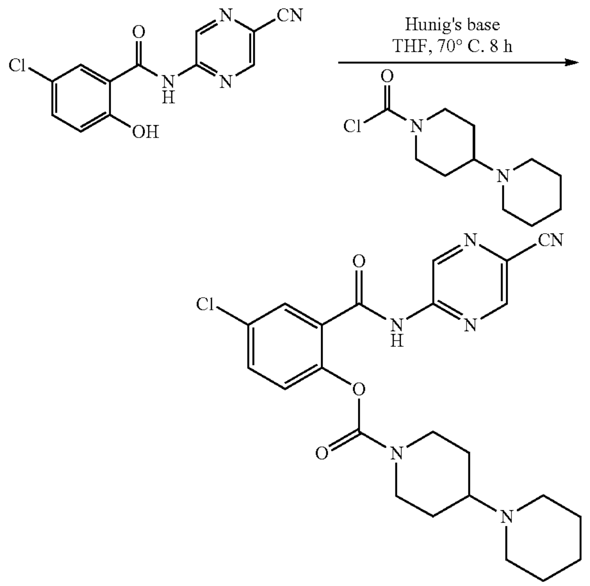

To an empty flask was added 5-chloro-N-(5-cyanopyrazin-2-yl)-2-hydroxybenzamide (200.0 mg, 0.728 mmol), followed by the addition of THF (5.0 mL) and Hunig's base (0.26 mL, 1.456 mmol). To this solution was added [1,4'-bipiperidine]-P-carbonyl chloride (202 mg, 0.874 mmol). The reaction was stirred at 70° C. for 16 hours before silica gel was added. Solvent was then removed and the residue was purified via silica gel column chromatography to give 4-chloro-2-((5-cyanopyrazin-2-yl)carbamoyl)phenyl [1,4'-bipiperidine]-1'-carboxylate 24 (183.0 mg, 54% yield). $^1$H NMR (500 MHz, DMSO-d6) δ 11.81 (s, 1H), 9.41 (d, J=1.4 Hz, 1H), 9.03 (d, J=1.4 Hz, 1H), 7.74 (d, J=2.6 Hz, 1H), 7.64 (dd, J=8.7, 2.6 Hz, 1H), 7.31 (d, J=8.7 Hz, 1H), 4.13 (d, J=13.4 Hz, 1H), 3.95-3.82 (m, 1H), 2.96-2.83 (m, 1H), 2.78-2.63 (m, 1H), 2.38 (ddt, J=11.7, 7.2, 3.7 Hz, 1H), 2.29 (t, J=5.3 Hz, 4H), 1.58 (t, J=14.5 Hz, 2H), 1.44 (q, J=5.2 Hz, 4H), 1.35 (dt, J=8.5, 5.9 Hz, 2H), 1.22 (q, J=12.0, 8.3 Hz, 1H), 1.16-1.02 (m, 1H). MS (ESI) exact mass calculated for [M+H] (C23H26ClN6O3) requires m/z 469.2, found m/z 469.0.

25

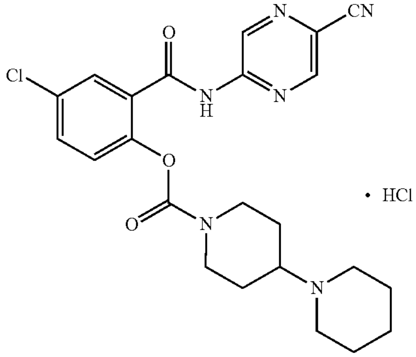

4-chloro-2-((5-cyanopyrazin-2-yl)carbamoyl)phenyl [1,4'-bipiperidine]-1'-carboxylate Hydrochloride (25)

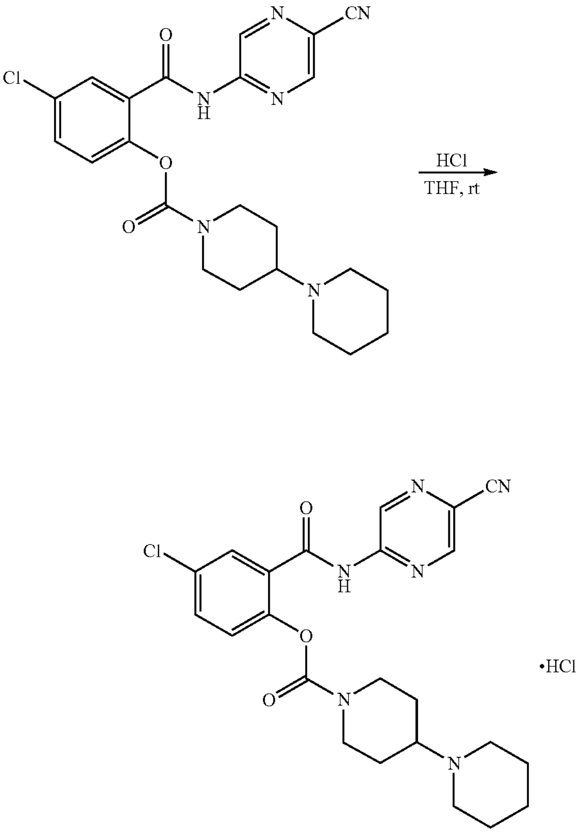

4-chloro-2-((5-cyanopyrazin-2-yl)carbamoyl)phenyl [1,4'-bipiperidine]-1'-carboxylate (68.1 mg, 0.145 mmol) was dissolved in THF (6.0 mL), followed by the addition of HCl (2.0 M in ether, 73 μL). The mixture was stirred at rt for 10 minutes. The resulting white precipitate was filtered and washed with diethyl ether to afford 4-chloro-2-((5-cyanopyrazin-2-yl)carbamoyl)phenyl [1,4'-bipiperidine]-1'-carboxylate hydrochloride 25 (64.5 mg, 88% yield). $^1$H NMR (300 MHz, DMSO-d6) δ 11.87 (s, 111), 9.45 (dd, J=1.5, 0.6 Hz, 1H), 9.06 (dd, J=1.5, 0.6 Hz, 1H), 7.82 (d, J=2.6 Hz, 1H), 7.73-7.62 (m, 1H), 7.35 (d, J=8.7 Hz, 1H), 4.25 (br m, 1H), 4.05 (br m, 1H), 2.87 (br m, 5H), 2.09-1.92 (m, 2H), 1.80 (s, 5H), 1.55-1.40 (br m, 4H), 1.25 (s, 1H). MS was not recorded due to the ionic nature of the HCl salt.

26

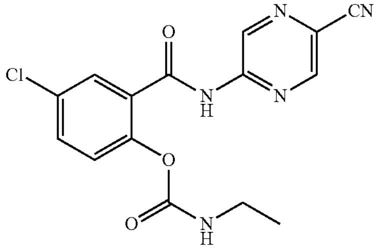

4-Chloro-2-((5-cyanopyrazin-2-yl)carbamoyl)phenyl ethylcarbamate (26)

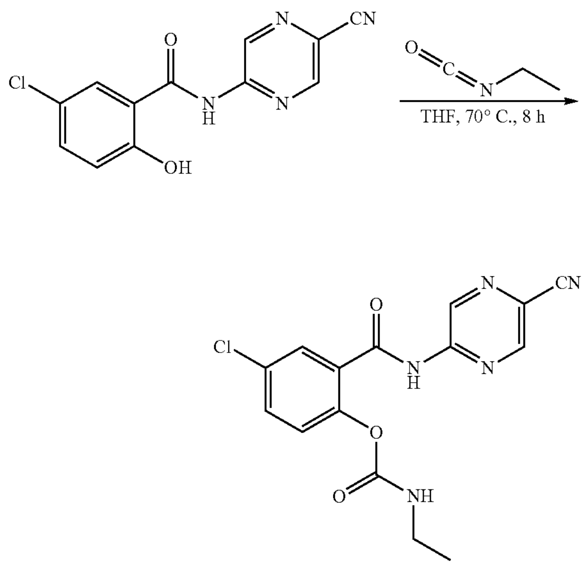

To an empty flask was added 5-chloro-N-(5-cyanopyrazin-2-yl)-2-hydroxybenzamide (100.0 mg, 0.364 mmol), THF (5.0 mL) and isocyanatoethane (35 μL, 0.437 mmol). The mixture was stirred at 70° C. for 8 hours before silica gel was added. The residue was purified via silica gel column chromatography to yield 4-chloro-2-((5-cyanopyrazin-2-yl)carbamoyl)phenyl ethylcarbamate 26 (72.9 mg, 58% yield). $^1$H NMR (500 MHz, Acetone-d6) δ 10.39 (s, 1H), 9.62 (d, J=1.4 Hz, 1H), 8.88 (d, J=1.5 Hz, 1H), 7.85 (d, J=2.6 Hz, 1H), 7.63 (dd, J=8.7, 2.7 Hz, 1H), 7.34 (d, J=8.8 Hz, 1H), 7.11 (s, 1H), 3.18 (qd, J=7.2, 5.7 Hz, 2H), 1.08 (t, J=7.2 Hz, 3H). MS (ESI) exact mass calculated for [M+H] (C15H13ClN5O3) requires m/z 346.1, found m/z 345.9.

27

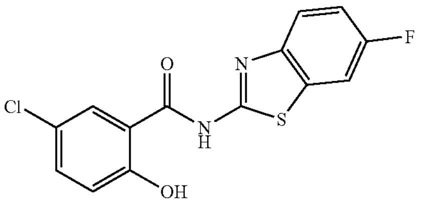

5-chloro-N-(6-fluorobenzo[d]thiazol-2-yl)-2-hydroxybenzamide (27)

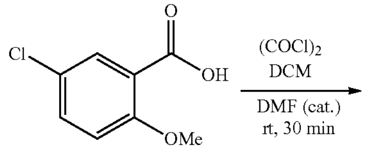

-continued

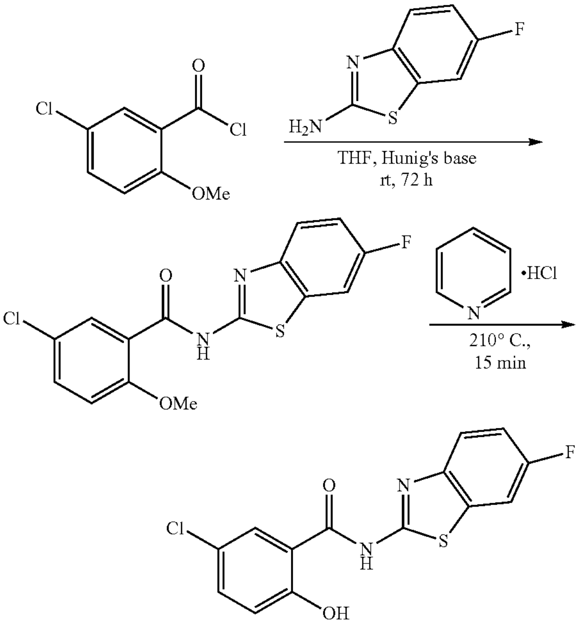

5-Chloro-2-methoxybenzoic acid (861.8 mg, 4.619 mmol) was dissolved in DCM (15.0 mL), followed by the addition of catalytic amount of DMF (40 μL) and oxalyl chloride (0.48 mL, 5.542 mmol) respectively. The reaction was allowed to stir at rt for 30 min and concentrated in vacuo. The residue was re-dissolved in THF (10.0 mL), and Hunig's base (0.81 mL, 4.619 mmol) and 6-fluorobenzo[d]thiazol-2-amine (620.0 mg, 3.686 mmol) were added. The mixture was stirred at rt for 72 hours before it was filtered. The filter cake was washed with diethyl ether and DCM to give 5-chloro-N-(6-fluorobenzo[d]thiazol-2-yl)-2-methoxybenzamide (837.0 mg, 67% yield). This compound (204.8 mg, 0.608 mmol) was then mixed with pyridinium chloride (2.100 g). The mixture was heated to 210° C., stirred for 15 minutes and cooled down to rt. The resulting solid was suspended in water and filtered. The filter cake was washed with diethyl ether to give 5-chloro-N-(6-fluorobenzo[d]thiazol-2-yl)-2-hydroxybenzamide 27 (128.6 mg, 63% yield). $^1$H NMR (500 MHz, DMSO-d6) δ 7.99-7.85 (m, 2H), 7.74 (d, J=8.6 Hz, 1H), 7.51 (dd, J=8.7, 2.8 Hz, 1H), 7.32 (td, J=8.9, 2.9 Hz, 1H), 7.06 (d, J=8.9 Hz, 1H). MS (ESI) exact mass calculated for [M+H] (C14H9ClFN2O2S) requires m/z 323.0, found m/z 322.8.

28

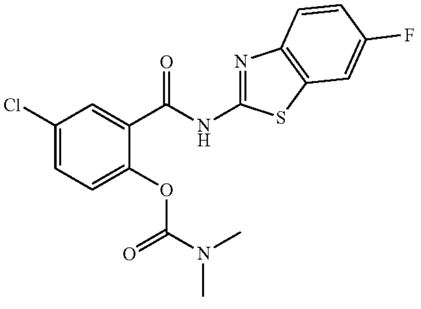

4-Chloro-2-((6-fluorobenzo[d]thiazol-2-yl)carbamoyl)phenyl dimethylcarbamate (28)

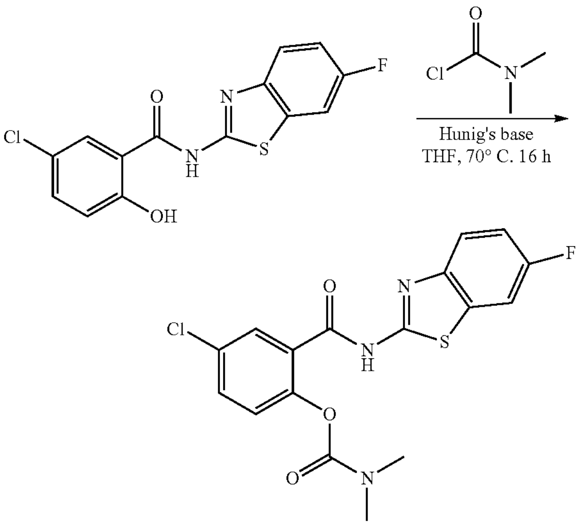

To an empty flask was added 5-chloro-N-(6-fluorobenzo[d]thiazol-2-yl)-2-hydroxybenzamide (120.0 mg, 0.372 mmol), followed by the addition of THF (5.0 mL) and Hunig's base (0.26 mL, 1.487 mmol). To this solution was added dimethylcarbamic chloride (69 μL, 0.744 mmol). The reaction was stirred at 70° C. for 16 hours before silica gel was added. Solvent was then removed and the residue was purified via silica gel column chromatography to yield 4-chloro-2-((6-fluorobenzo[d]thiazol-2-yl)carbamoyl)phenyl dimethylcarbamate 28 (122.5 mg, 84% yield). 1H NMR (300 MHz, Chloroform-d) δ 7.90 (d, J=2.6 Hz, 1H), 7.62 (dd, J=8.9, 4.7 Hz, 1H), 7.52 (ddd, J=10.1, 8.4, 2.6 Hz, 2H), 7.22 (d, J=8.7 Hz, 1H), 7.14 (td, J=8.9, 2.6 Hz, 1H), 3.26 (s, 3H), 3.07 (s, 3H). MS (ESI) exact mass calculated for [M+H] (C17H14ClFN3O3S) requires m/z 394.0, found m/z 393.7.

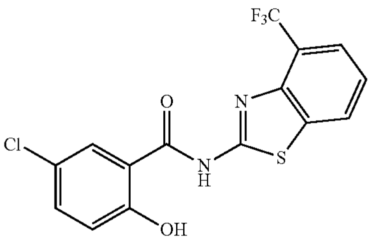

29

5-Chloro-2-hydroxy-N-(4-(trifluoromethyl)benzo[d]thiazol-2-yl)benzamide (29)

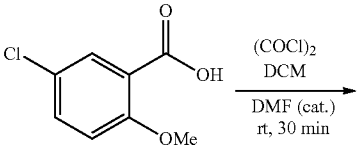

-continued

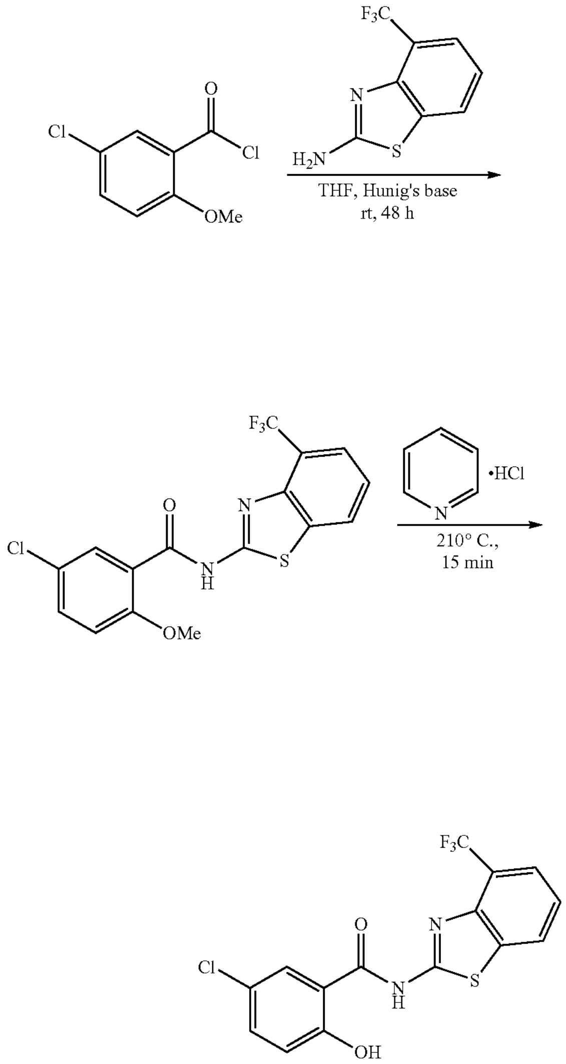

5-Chloro-2-methoxybenzoic acid (427.0 mg, 2.291 mmol) was dissolved in DCM (10.0 mL), followed by the addition of catalytic amount of DMF (30 μL) and oxalyl chloride (0.24 mL, 2.750 mmol) respectively. The reaction was allowed to stir at rt for 30 min and concentrated in vacuo. The residue was re-dissolved in THF (10.0 mL), and Hunig's base (0.40 mL, 2.291 mmol) and 4-(trifluoromethypbenzo[d]thiazol-2-amine (400.0 mg, 1.833 mmol) were added. The mixture was stirred at rt for 48 hours before it was filtered. The filter cake was washed with diethyl ether and DCM to give 5-chloro-2-methoxy-N-(4-(trifluoromethypbenzo[d]thiazol-2-yl)benzamide (644.3 mg, 91% yield). This compound (333.1 mg, 0.861 mmol) was then mixed with pyridinium chloride (3.330 g). The mixture was heated to 210° C., stirred for 15 minutes and cooled down to rt. The resulting solid was suspended in water and filtered. The filter cake was washed with diethyl ether to give 5-chloro-2-hydroxy-N-(4-(trifluoromethypbenzo[d]thiazol-2-yl)benzamide 29 (102.2 mg, 32% yield). $^1$H NMR (300 MHz, DMSO-d6) δ 8.38 (d, J=7.9 Hz, 1H), 7.92 (d, J=2.8 Hz, 1H), 7.83 (d, J=7.6 Hz, 1H), 7.59-7.45 (m, 2H), 7.09 (d, J=8.8 Hz, 1H). MS (ESI) exact mass calculated for [M+H] (C15H9ClF3N2O2S) requires m/z 373.0, found m/z 372.8.

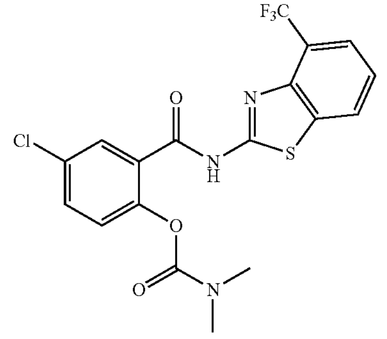

30

4-chloro-2-((4-(trifluoromethyl)benzo[d]thiazol-2-yl)carbamoyl)phenyl Dimethylcarbamate (30)

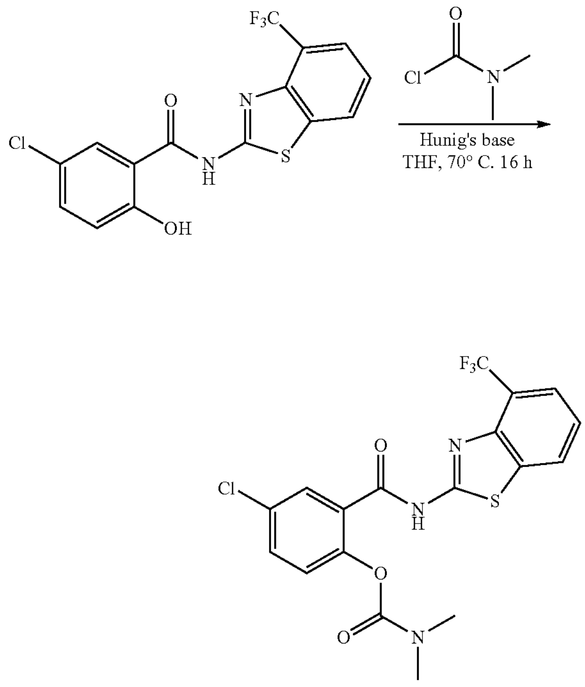

To an empty flask was added 5-chloro-2-hydroxy-N-(4-(trifluoromethypbenzo[d]thiazol-2-yl)benzamide (120.0 mg, 0.322 mmol), followed by the addition of THF (5.0 mL) and Hunig's base (0.22 mL, 1.288 mmol). To this solution was added dimethylcarbamic chloride (60 μL, 0.644 mmol). The reaction was stirred at 70° C. for 16 hours before silica gel was added. Solvent was then removed and the residue was purified via silica gel column chromatography to yield 4-chloro-2 ((4-(trifluoromethypbenzo[d]thiazol-2-yl)carbamoyl)phenyl dimethylcarbamate 30 (99.6 mg, 70% yield). $^1$H NMR (300 MHz, Chloroform-d) δ 10.53 (s, 1H), 8.10 (d, J=2.7 Hz, 1H), 8.05 (ddd, J=7.5, 1.4, 0.7 Hz, 1H), 7.76 (ddd, J=7.6, 1.3, 0.7 Hz, 1H), 7.56 (ddd, J=8.8, 2.7, 0.6 Hz, 1H), 7.46-7.36 (m, 1H), 7.28 (d, J=8.8 Hz, 1H), 3.36 (s, 3H), 3.09 (s, 3H). MS (ESI) exact mass calculated for [M+H] (C18H14ClF3N3O3S) requires m/z 444.0, found m/z 443.7.

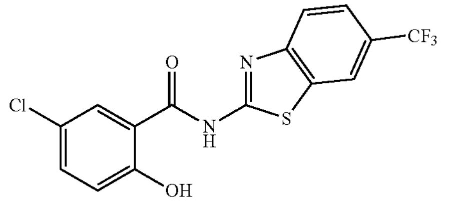

31

5-chloro-2-hydroxy-N-(6-(trifluoromethyl)benzo[d]thiazol-2-yl)benzamide (31)

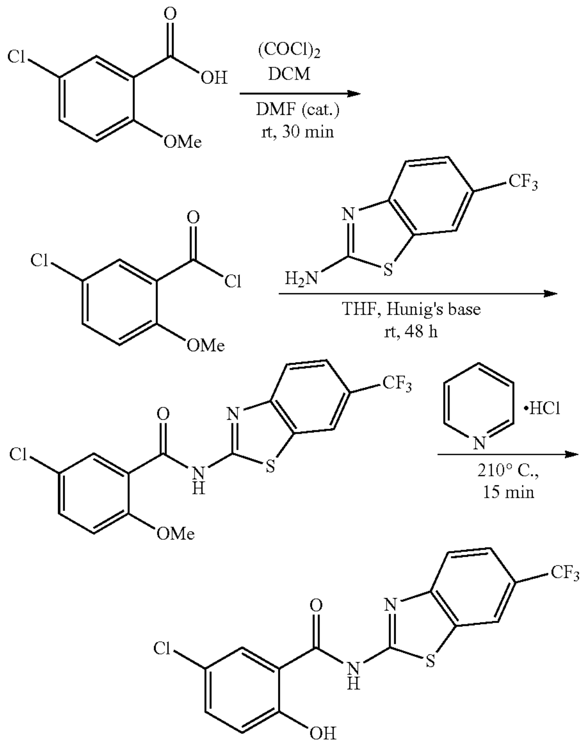

5-Chloro-2-methoxybenzoic acid (535.0 mg, 2.864 mmol) was dissolved in DCM (15.0 mL), followed by the addition of catalytic amount of DMF (40 μL) and oxalyl chloride (0.30 mL, 3.437 mmol) respectively. The reaction was allowed to stir at rt for 30 min and concentrated in vacuo. The residue was re-dissolved in THF (10.0 mL), and Hunig's base (0.50 mL, 2.864 mmol) and 6-(trifluorometh-ypbenzo[d]thiazol-2-amine (500.0 mg, 2.291 mmol) were added. The mixture was stirred at rt for 48 hours before it was filtered. The filter cake was washed with diethyl ether and DCM to give 5-chloro-2-methoxy-N-(6-(trifluoromet-hypbenzo[d]thiazol-2-yl)benzamide (710.5 mg, 80% yield). This compound (400.0 mg, 1.034 mmol) was then mixed with pyridinium chloride (4.000 g). The mixture was heated to 210° C., stirred for 15 minutes and cooled down to rt. The resulting solid was suspended in water and filtered. The filter cake was washed with diethyl ether to give 5-chloro-2-hydroxy-N-(6-(trifluoromethypbenzo[d]thiazol-2-yl)benzamide 31 (219.1 mg, 57% yield). $^1$H NMR (300 MHz, DMSO-d6) δ 8.56 (d, J=2.2 Hz, 1H), 7.93 (dd, J=6.2, 4.0 Hz, 2H), 7.84-7.72 (m, 1H), 7.55 (dt, J=8.8, 2.4 Hz, 1H), 7.10

(dd, J=9.0, 2.0 Hz, 1H). MS (ESI) exact mass calculated for [M+H] (C15H9ClF3N2O2S) requires m/z 373.0, found m/z 372.7.

32

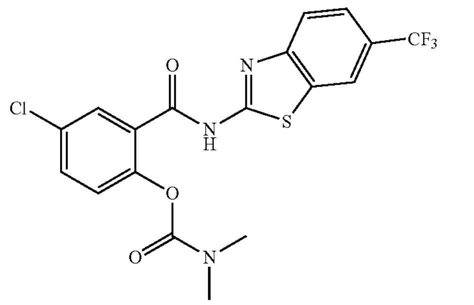

4-chloro-2-((6-(trifluoromethyl)benzo[d]thiazol-2-yl)carbamoyl)phenyl dimethylcarbamate (32)

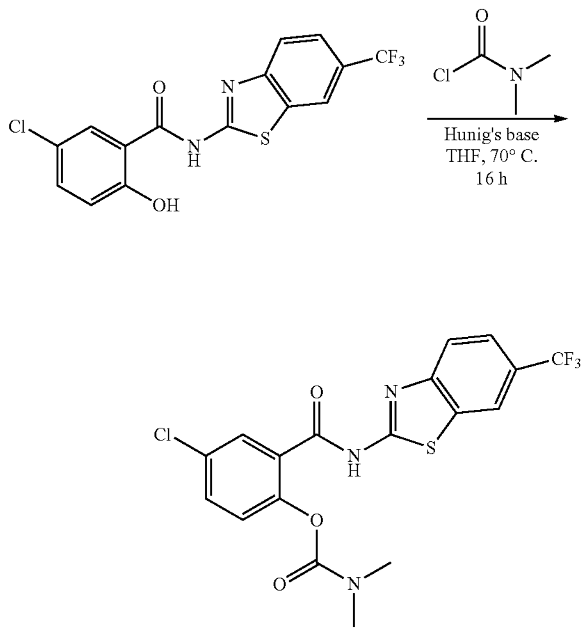

To an empty flask was added 5-chloro-2-hydroxy-N-(6-(trifluoromethypbenzo[d]thiazol-2-yl)benzamide (71.9 mg, 0.193 mmol), followed by the addition of THF (5.0 mL) and Hunig's base (84 μL, 0.482 mmol). To this solution was added dimethylcarbamic chloride (27 μL, 0.290 mmol). The reaction was stirred at 70° C. for 16 hours before silica gel was added. Solvent was then removed and the residue was purified via silica gel column chromatography to yield 4-chloro-2-((6-(trifluoromethypbenzo[d]thiazol-2-yl)carbamoyl)phenyl dimethylcarbamate 32 (44.3 mg, 52% yield). $^{1}$H NMR (300 MHz, Chloroform-d) δ 8.10 (tt, J=1.4, 0.8 Hz, 1H), 7.82 (t, J=2.2 Hz, 1H), 7.67 (dq, J=8.5, 0.8 Hz, 1H), 7.62-7.56 (m, 1H), 7.48-7.42 (m, 1H), 7.21 (dd, J=8.8, 1.7 Hz, 1H), 3.27 (d, J=1.7 Hz, 3H), 3.08 (d, J=1.6 Hz, 3H). MS (ESI) exact mass calculated for [M+H] (C18H14ClF3N3O3S) requires in/z 444.0, found m/z 443.7.

33

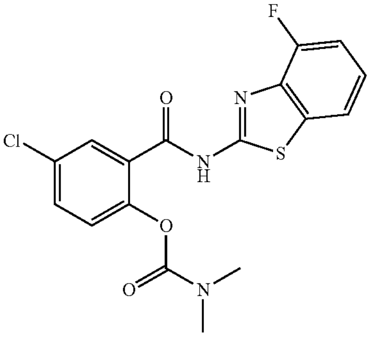

4-chloro-2-((4-fluorobenzo[d]thiazol-2-yl)carbamoyl)phenyl dimethylcarbamate (33)

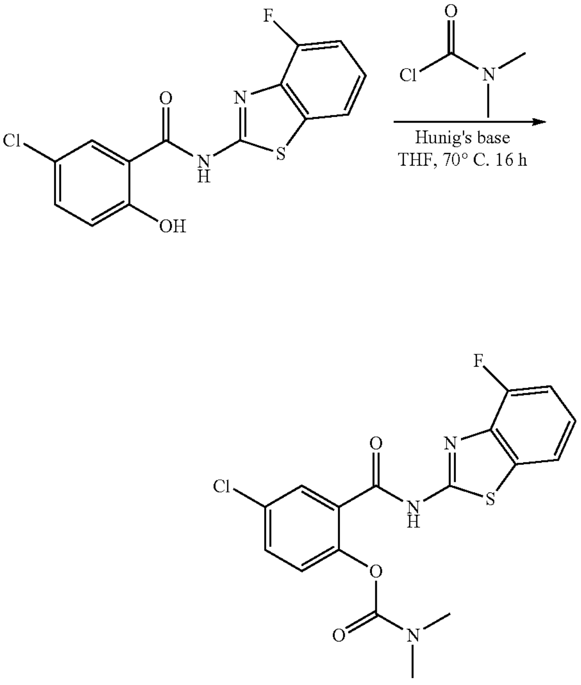

To an empty flask was added 5-chloro-N-(4-fluorobenzo[d]thiazol-2-yl)-2-hydroxybenzamide (66.0 mg, 0.240 mmol), followed by the addition of THF (5.0 mL) and Hunig's base (84 μL, 0.480 mmol). To this solution was added dimethylcarbamic chloride (27 μL, 0.290 mmol). The reaction was stirred at 70° C. for 16 hours before silica gel was added. Solvent was then removed and the residue was purified via silica gel column chromatography to yield 4-chloro-2-((4-fluorobenzo[d]thiazol-2-yl)carbamoyl)phenyl dimethylcarbamate 33 (54.2 mg, 57% yield). $^{1}$H NMR (500 MHz, Chloroform-d) δ 10.66 (s, 1H), 7.87 (d, J=2.6 Hz, 1H), 7.54 (dd, J=8.0, 1.0 Hz, 1H), 7.43 (dd, J=8.8, 2.6 Hz, 1H), 7.24-7.17 (m, 2H), 7.09 (ddd, J=10.5, 8.1, 1.0 Hz, 1H), 3.26 (s, 3H), 3.08 (s, 3H). MS (ESI) exact mass calculated for [M+H] (C17H14ClFN3O3S) requires m/z 394.0, found m/z 393.7.

34

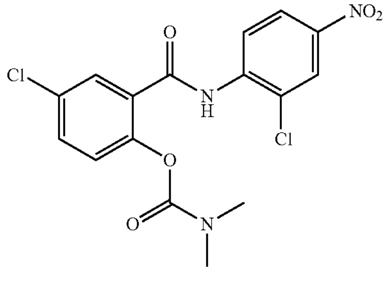

4-chloro-2-((2-chloro-4-nitrophenyl)carbamoyl)phenyl dimethylcarbamate (34)

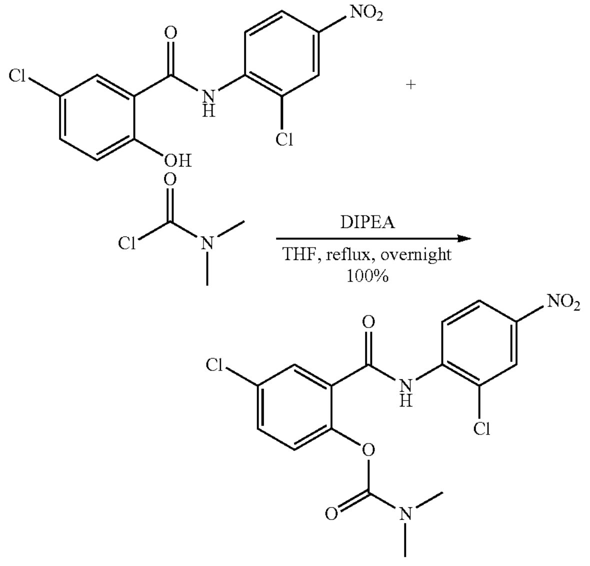

To a stirred solution of niclosamide (277 mg, 0.847 mmol) in THF (5.0 mL) was added DIPEA (592 ul, 3.4 mmol) and then dimethylcarbamoyl chloride (157 μL, 1.7 mmol). The reaction was refluxed overnight. After cooled down, THF was removed and the residue was dissolved in EA and washed with 1N HCl (two times), Sat. $NaHCO_3$ (two times) and brine (one time). The organic layer was dried over sodium sulfate, filtered and concentrated to give 34 as a white solid (336 mg, 100%). $^1H$ NMR (300 MHz, $cdcl_3$) δ 9.01 (s, 1H), 8.82 (d, J=9.2 Hz, 1H), 8.34 (d, J=2.6 Hz, 1H), 8.22 (dd, J=9.2, 2.6 Hz, 1H), 7.91 (d, J=2.6 Hz, 1H), 7.52 (dd, J=8.7, 2.6 Hz, 1H), 7.14 (d, J=8.7 Hz, 1H), 3.14 (s, 3H), 3.01 (s, 3H). MS (ESI) exact mass calculated for $[M+Na]^+$ ($C_{16}H_{13}Cl_2N_3NaO_5$) requires m/z 420.01, found m/z 419.75.

35

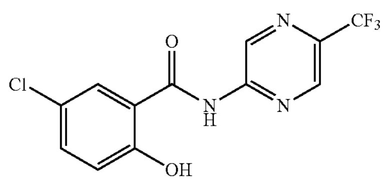

5-chloro-2-hydroxy-N-(5-(trifluoromethyl)pyrazin-2-yl)benzamide (35)

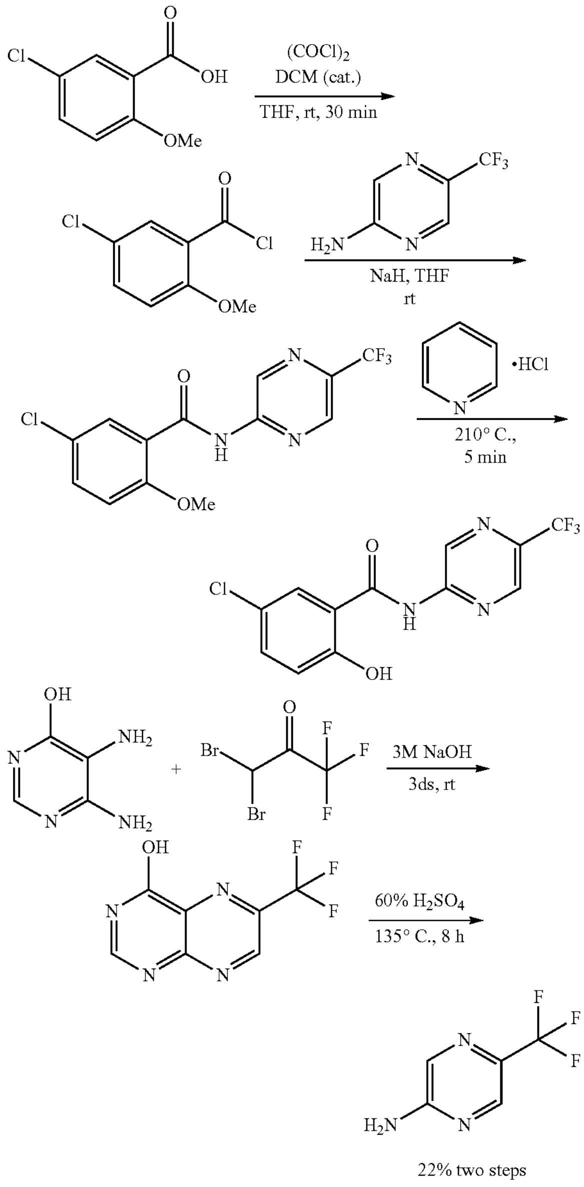

To an ice bath cooled solution of 5,6-diaminopyrimidin-4-ol (1.94 g, 15.4 mmol) in 3M NaOH (19.3 ml, 58 mmol) was added 3,3-dibromo-1,1,1-trifluoropropan-2-one (1.36 ml, 10 mmol). The reaction was stirred for 72 h at room temperature. The reaction was acidified to PH=5 and extracted with DCM for three times. The combined organic phase was dried over sodium sulfate, filtered and concentrated. The residue was dissolved in 60% sulfuric acid (15 ml) and stirred at 135° C. for 8 hs. The reaction was cooled, poured over ice and neutralized to PH=8 with conc. ammonia and extracted with EA for 5 times. The combined organic phase was dried over sodium sulfate, filtered and concentrated. The residue was recrystallized form hexane to afford the 5-(trifluoromethyl)pyrazin-2-amine as a white solid (370 mg, 22%). $^1H$ NMR (300 MHz, $CDC1_3$) 88.31 (s, 1H), 8.01

(s, 1H), 5.43 (brs, 2H). MS (ESI) exact mass calculated for $[M+H]^+$ ($C_5H_5F_3N_3$) requires m/z 164.04, found m/z 163.85.

5-chloro-2-methoxybenzoic acid (229.0 mg, 1.226 mmol) was dissolved in THF (5.0 mL), followed by the addition of catalytic amount of DMF (10 μL) and oxalyl chloride (0.127 mL, 1.472 mmol) respectively. The reaction was allowed to stir at rt for 30 min, concentrated in vacuo, and the residue was re-dissolved in THF (3.0 mL). In another flask, 5-(trifluoromethyl)pyrazin-2-amine (160.0 mg, 0.981 mmol) was dissolved in THF (5.0 mL) followed by addition of NaH (60.0 mg, 1.47 mmol, 60% in mineral oil). The mixture was stirred for 10 minutes before it was added to the flask containing the freshly prepared acid chloride dropwise at rt. The reaction was stirred at rt for 30 min before silica gel was added to quench the reaction. Solvent was evaporated and the resulting residue was purified via silica gel column chromatography to yield 35 as a white solid (76.0 mg, 23% yield). $^1$H NMR (300 MHz, cdc13) δ 10.56 (s, 1H), 9.80 (s, 1H), 8.63 (s, 1H), 8.24 (d, J=2.8 Hz, 1H), 7.51 (dd, J=8.8, 2.8 Hz, 1H), 7.02 (d, J=8.9 Hz, 1H), 4.11 (s, 3H). MS (ESI) exact mass calculated for $[M+Na]^+$ ($C_{13}H_{10}ClF_3N_3O_2$) requires m/z 332.04, found m/z 331.75. This compound (95 mg, 0.287 mmol) was mixed with pyridinium chloride (1.0 g). The mixture was heated to 210° C., stirred for 15 minutes and cooled down to rt. The resulting solid was dissolved in water and extracted with ethyl acetate. The organic layer was concentrated in vacuo and the residue was purified via silica gel column chromatography to yield the title compound as a yellow solid (67.0 mg, 75% yield). $^1$H NMR (400 MHz, $cdcl_3$) δ 11.23 (s, 1H), 9.71 (s, 1H), 8.78 (s, 1H), 8.69 (s, 1H), 7.61 (d, J=2.4 Hz, 1H), 7.48 (dd, J=8.9, 2.4 Hz, 1H), 7.04 (d, J=9.0 Hz, 1H). MS (ESI) exact mass calculated for [M+H] ($C_{12}H_8ClF_3N_3O_2$) requires m/z 318.03, found m/z 317.85.

36

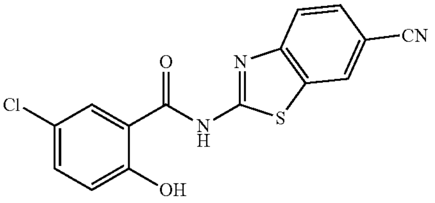

5-chloro-N-(6-cyanobenzo[d]thiazol-2-yl)-2-hydroxybenzamide (36)

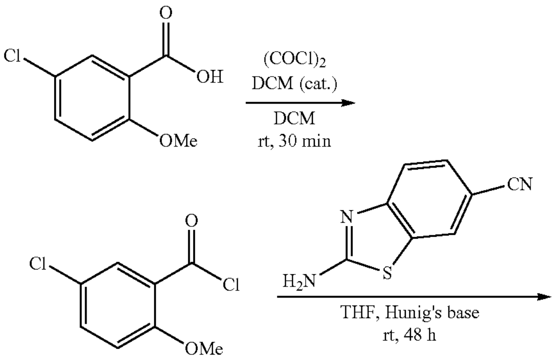

-continued

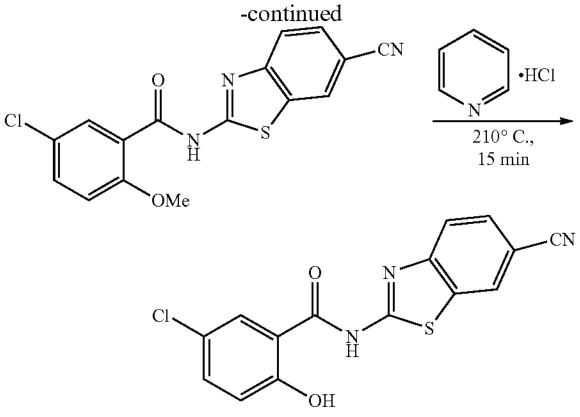

5-Chloro-2-methoxybenzoic acid (107.0 mg, 0.571 mmol) was dissolved in DCM (3.0 mL), followed by the addition of catalytic amount of DMF (10 μL) and oxalyl chloride (0.06 mL, 0.685 mmol) respectively. The reaction was allowed to stir at rt for 30 min and concentrated in vacuo. The residue was re-dissolved in THF (3.0 mL), and Hunig's base (0.10 mL, 0.571 mmol) and 2-aminobenzo[d]thiazole-6-carbonitrile (80.0 mg, 0.456 mmol) were added. The mixture was stirred at rt for 48 hours before it was filtered. The filter cake was washed with diethyl ether and DCM to give 5-chloro-N-(6-cyanobenzo[d]thiazol-2-yl)-2-methoxybenzamide (122 mg, 79% yield). This compound (122 mg, 0.356 mmol) was then mixed with pyridinium chloride (1.0 g). The mixture was heated to 210° C., stirred for 15 minutes and cooled down to rt. The resulting solid was suspended in water and filtered. The filter cake was washed with diethyl ether to give 36 as a yellow solid (31.0 mg, 32% yield). $^1$H NMR (300 MHz, DMSO-d6) δ 12.42 (s, 1H), 8.61 (s, 1H), 7.91 (d, J=2.7 Hz, 1H), 7.89 (d, J=7.1 Hz, 2H), 7.53 (dd, J=8.8, 2.8 Hz, 1H), 7.28 (dd, J=15.7, 9.7 Hz, 1H), 7.08 (d, J=8.8 Hz, 1H). MS (ESI) exact mass calculated for [M+H] ($C_{15}H_9ClN_3O_2S$) requires m/z 330.01, found m/z 329.80

Mitochondrial Uncoupling Activity Assay

Mitochondrial uncoupling analyses in live cells were performed with cultured mammalian cells, the NIH-3T3 cells, or HepG2 cells. Cells were seeded onto 6-well plate and cultured in DMEM medium supplemented with 10% fetal bovine serum and 2 mM glutamine. Cells were allowed to grow to logarithmic growth phase prior to experiments. The cells were treated with each individual synthesized compound at various concentrations for two hours, followed by staining with TMRE (tetramethylrhodamine ethyl ester) at final concentration of 100 nM for 15 minutes. The cells were then washed once with PBS, and examined under fluorescence microscopy. A positive control of cells treated with various concentrations of niclosamide ethanolamine were used as positive control. Percentage of cells losing mitochondrial TMRE staining was used as a quantification of mitochondrial uncoupling activity. EC50 of an indicated compound is defined as the concentration at which the fluorescent intensity of mitochondrial TMRE staining in cells is reduced to about 50%. The mitochondrial uncoupling activity of the compounds was further confirmed by cellular oxygen consumption analysis at concentrations above EC50, both in the absence and in the presence of oligomycin (5 μg/ml) analyzed by Seahorse XF96 assay. The increase in oxygen consumption upon treatment with the individual compound in the presence of oligomycin as compared to the untreated cells further confirmed mitochondrial uncoupling activity.

TABLE I

Summary of mitochondrial uncoupling activity of the synthesized compounds

| Compound Number | Activities[1] |
|---|---|
| 1 | *** |
| 2 | *** |
| 3 | *** |
| 4 | * |
| 5 | * |
| 6 | * |
| 7 | *** |
| 8 | ** |
| 9 | * |
| 10 | ** |
| 11 | ** |
| 12 | * |
| 13 | *** |
| 14 | *** |
| 15 | *** |
| 16 | *** |
| 17 | *** |
| 18 | *** |
| 19 | *** |
| 20 | *** |
| 21 | ** |
| 22 | ** |
| 23 | N/A |
| 24 | N/A |
| 25 | N/A |
| 26 | N/A |
| 27 | *** |
| 28 | N/A |
| 29 | *** |
| 30 | N/A |
| 31 | *** |
| 32 | N/A |
| 33 | N/A |
| 34 | N/A |
| 35 | *** |
| 36 | *** |

[1]*, EC50 <=10 μM; , 10 μM < EC50 <= 50 μM; *, EC50 > 50 μM

The Effect of Compounds in Activating AMPK and Inhibiting Cell Proliferation

AMPK activation analysis by immunoblotting assay with antibody against phosphorylated AMPK: mouse pancreatic cancer cell line, Panc02, or NIH-3T3 fibroblasts, or human liver carcinoma cell line HepG2, were cultured in Dulbecco's modified Eagle's medium (DMEM) supplemented with 10% (vol/vol) fetal bovine serum, 100 unit·$ml^{-1}$ of penicillin, 100 μg·$ml^{-1}$ of streptomycin and 0.29 mg·$ml^{-1}$ of L-glutamine at 37° C. and 5% $CO_2$. For treatment, individual compound was first dissolved in DMSO to make stock solution, and then was added directly to the culturing medium to desired concentration by at least 1:1000 dilution. After a two-hour treatment, cells were collected and homogenized within lysis buffer containing 10 mM TRIS-HCl (pH 7.9), 10% glycerol, 0.1 mM EDTA, 100 mM KCl, 0.2% NP-40, 0.5 mM PMSF, 1 mM DTT, mini-complete protease inhibitor cocktail (Roche, 11836153001), and phosphatase inhibitor cocktail (Roche, 04906845001) if required. Nuclei and insoluble debris were pelleted in an Eppendorf microcentrifuge at 10,000 rpm for 5 min at 4° C. Cell extracts were then stored at −20° C. or immediately subjected to sodium dodecyl sulfate-polyacrylamide gel electrophoresis (SDS-PAGE). For the SDS-PAGE, cell extracts were mixed with 5× Laemmli loading buffer and heated at 95° C. for 5 min prior to electrophoresis. For immunoblotting, proteins were transferred to polyvinylidene difluoride (PVDF) membranes (Millipore, IPVH00010). Prior to incubating with primary antibody (Phospho-AMPKα (Thr172) mAb (#2535, Cell Signaling Technology), AMPKα mAb (#2793, Cell Signaling Technology), Ran antibody (sc-1156, Santa Cruz Biotechnology)), membranes were blocked with 5% milk in phosphate-buffered saline supplemented with 0.1% (vol/vol) Tween-20 for 1 h at room temperature. Chemiluminescent detection was completed with ECL western blotting reagents (Amersham, 95038-566). Quantification was determined by measuring band intensity using ImageJ software and calculating the ratio of protein of interesting to internal loading control.

Example immunoblotting assay with antibodies against phosphorylated AMPK, indicative of AMPK activity. NEN, niclosamide ethanolamine as a control mitochondrial uncoupler; Example #14 is shown in this assay as an example.

TABLE II

Activity of example compounds for AMPK activation is correlated with mitochondrial uncoupling activity.

| | Example # | | |
|---|---|---|---|
| | #2 | #13 | #14 |
| Concentrations for AMPK activation[1] | *** | *** | *** |

[1]***, <=10 μM.

Clonogenic assay for determining activity of cell proliferation inhibition: mouse colon cancer cell line MC38 was seeded onto 6-well plates at the density of about 200 cells per well, grown under medium conditions as described above, after attachment, cells were treated with ascending concentrations of example compounds for 24-48 hrs. The drug-containing medium was then removed and fresh medium without drug was added to each well. Cells were then grown for 2 weeks for colony formation. During the two weeks, old medium was aspirated out and fresh drug-free medium was added to the wells every two days. At the end of the experiment, the colonies were counted for the treatment at each concentration. IC50 is defined as the concentration that inhibits 50% of colony formation as compared to the no drug treatment control.

TABLE III

Activity of inhibition of colony formation by example compound

| | Example # #14 |
|---|---|
| IC50 concentrations[1] | *** |

[1]***, <=10 μM.

The invention claimed is:

1. A compound of formula (I) having the structure:

(I)

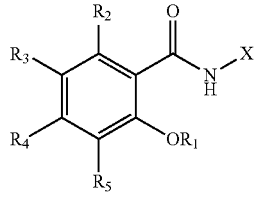

or a pharmaceutically acceptable salt, solvate, or prodrug thereof, wherein:

$R_1$ is selected from the group consisting of H, M, $PO(OH)_2$, $PO_2(OH)M$, $PO_3M_2$, $PO(OH)R_a$, $PO(OM)R_a$, $PO(R_a)_2$, and $C(O)R_a$, wherein M is a metal cation or an organic amine;

$R_2$, $R_4$, and $R_5$ are H;

$R_3$ is chloro;

X is a 9-membered ring having the structure:

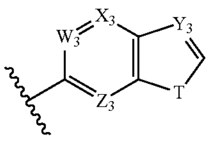

or

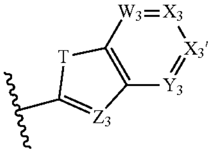

wherein T is O or S; $W_3$, $X_3$, $X_3'$, $Y_3$, and $Z_3$ are each independently $CR_b$ or N;

each $R_a$ is independently selected from the group consisting of H, alkyl, aryl, alkoxy, aryloxy, alkoxyalkyl, amino, alkylamino, and alkyl-carbonyloxy-alkyl;

each $R_b$ is independently selected from the group consisting of H, CN, $NO_2$, $CO_2H$, $CO_2R_a$, $CF_3$, $OCF_3$, $SF_3$, $C_{6-10}$aryl, haloalkyl, $CONHR_a$, and $C{=}NR_c(N(R_d)_2)$;

each $R_c$ is independently selected from the group consisting of H, CN, O-alkyl, $NH_2$, mono-alkyl substituted amino, and di-alkyl substituted amino; and each $R_d$ is independently selected from the group consisting of H and alkyl, wherein said alkyl is optionally substituted with halogen, CN, $NO_2$, $CO_2H$, $CO_2R_a$, $CF_3$, $OCF_3$, $SF_3$, $C_{6-10}$aryl, or $CONHR_a$; and provided that said 9-membered ring contains at least one nitrogen and is not indole; and provided the compound is not N-(benzo[d]thiazol-2-yl)-5-chloro-2-hydroxybenzamide.

2. The compound of claim 1, wherein said 9-membered ring is benzothiazole optionally substituted with $R_b$.

3. A compound selected from the group consisting of

5-Chloro-N-(4-fluorobenzo[d]thiazol-2-yl)-2-hydroxybenzamide, 5-chloro-N-(6-fluorobenzo[d]thiazol-2-yl)-2-hydroxybenzamide, 4-Chloro-2-((6-fluorobenzo[d]thiazol-2-yl)carbamoyl)phenyl dimethylcarbamate, 5-Chloro-2-hydroxy-N-(4-(trifluoromethyl)benzo[d]thiazol-2-yl)benzamide, 4-chloro-2((4-(trifluoromethyl)benzo[d]thiazol-2-yl)carbamoyl)phenyl, dimethylcarbamate, 5-chloro-2-hydroxy-N-(6-(trifluoromethyl)benzo[d]thiazol-2-yl)benzamide, 4-chloro-2((6-(trifluoromethyl)benzo[d]thiazol-2-yl)carbamoyl)phenyl, dimethylcarbamate, 4-chloro-2-((4-fluorobenzo[d]thiazol-2-yl)carbamoyl)phenyl dimethylcarbamate, 5-chloro-N-(6-cyanobenzo[d]thiazol-2-yl)-2-hydroxybenzamide, and a pharmaceutically acceptable salt thereof.

4. A pharmaceutical composition comprising a therapeutically effective amount of compound according to any of claim 1, 2, or 3, or a pharmaceutically acceptable salt thereof, or a prodrug thereof.

5. A compound of formula (I) having the structure:

(I)

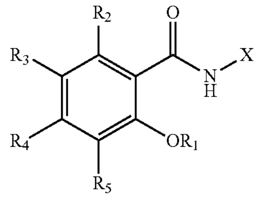

or a pharmaceutically acceptable salt, solvate, or prodrug thereof, wherein:

$R_1$ is selected from the group consisting of H, M, $PO(OH)_2$, $PO_2(OH)M$, $PO_3M_2$, $PO(OH)R_a$, $PO(OM)R_a$, $PO(R_a)_2$, and $C(O)R_a$, wherein M is a metal cation or an organic amine;

$R_2$, $R_4$, and $R_5$ are H;

$R_3$ is chloro;

X is a 9-membered ring having the structure:

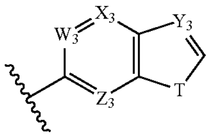

or

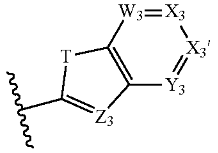

wherein T is O or S; $W_3$, $X_3$, $X_3'$, $Y_3$, and $Z_3$ are each independently $CR_b$ or N;

each $R_a$ is independently selected from the group consisting of H, alkyl, aryl, alkoxy, aryloxy, alkoxyalkyl, amino, alkylamino, and alkyl-carbonyloxy-alkyl;

each $R_b$ is independently selected from the group consisting of H, F, CN, $NO_2$, $CO_2H$, $CO_2R_a$, $CF_3$, $OCF_3$, $SF_3$, $C_{6-10}$aryl, haloalkyl, $CONHR_a$, and $C{=}NR_c(N(R_d)_2)$;

each $R_c$ is independently selected from the group consisting of H, CN, O-alkyl, $NH_2$, mono-alkyl substituted amino, and di-alkyl substituted amino; and each $R_d$ is independently selected from the group consisting of H and alkyl, wherein said alkyl is optionally substituted with halogen, CN, $NO_2$, $CO_2H$, $CO_2R_a$, $CF_3$, $OCF_3$, $SF_3$, $C_{6-10}$aryl, or $CONHR_a$; and provided that said 9-membered ring contains at least one nitrogen and is not indole; and provided the compound is not N-(benzo[d]thiazol-2-yl)-5-chloro-2-hydroxybenzamide.

6. The compound of claim 5, wherein said 9-membered ring is benzothiazole optionally substituted with $R_b$.

7. A pharmaceutical composition comprising a therapeutically effective amount of a compound according to claim 5, or a pharmaceutically acceptable salt thereof, or a prodrug thereof.

* * * * *